United States Patent [19]
Siminszky et al.

[11] Patent Number: 6,121,512
[45] Date of Patent: Sep. 19, 2000

[54] CYTOCHROME P-450 CONSTRUCTS AND METHOD OF PRODUCING HERBICIDE-RESISTANT TRANSGENIC PLANTS

[75] Inventors: Balazs Siminszky; Ralph Dewey; Frederick Corbin, all of Raleigh, N.C.

[73] Assignee: North Carolina State University, Raleigh, N.C.

[21] Appl. No.: 08/948,564

[22] Filed: Oct. 10, 1997

[51] Int. Cl.[7] ............................ C12N 15/29; C12N 15/82; A01H 5/00; A01H 4/00
[52] U.S. Cl. ..................... 800/298; 800/295; 800/298; 800/278; 435/419; 435/468; 435/320.1; 435/69.1; 536/23.6; 536/24.1
[58] Field of Search ....................... 800/295, 278, 800/298; 435/419, 468, 320.1, 69.1; 536/23.6, 24.1

[56] References Cited

U.S. PATENT DOCUMENTS

| | | | |
|---|---|---|---|
| 5,179,013 | 1/1993 | Matsuoka et al. | 435/125 |
| 5,349,127 | 9/1994 | Dean et al. | 800/205 |
| 5,478,723 | 12/1995 | Parkinson et al. | 435/4 |
| 5,516,674 | 5/1996 | Roe et al. | 435/189 |

OTHER PUBLICATIONS

Bolwell, et al., *Phytochemistry* 37:1491–1506 (1994).
Meijer, et al., *Plant Mol.Biol.* 22:379–383 (1993).
O'Keefe, et al., *Plant Physiol.* 105:473–482 (1994).
Pierrel, et al., *Eur. J. Biochem.* 224:835–844 (1994).
Pompon, et al., *Methods Enzymol.* 272:51–64 (1995).
Rubin and Eshel, *Weed Sci.* 19:592–594 (1971).
Schuler, *Critical Review in Plant Sciences*, 15:235–284 (1996).
Shiota, et al., *Plant Physiol*, 106:17–23 (1994).
Shiota, et al., *Pestic. Biochem Physiol.* 54:190–198 (1996).
Suzuki, et al., *J. Agric. Food Chem.* 29:1027–1033 (1981).
Voss and Geissbuhler, *Proc. Brit. Weed Contr. Conf.* 8:266–268 (1966).
B. Siminszky et al.; Glycine max cytochrom P450 monooxygenase CYP71A10 mRNA, complete cds, EMBL Database, AC AF022157 (Jan. 8, 1998).
PCT International Search Report, PCT/US 98/20807 (May 3, 1999).

*Primary Examiner*—Gary Benzion
*Assistant Examiner*—Thomas Haas
*Attorney, Agent, or Firm*—Myers Bigel Sibley & Sajovec

[57] ABSTRACT

DNA sequence encoding novel cytochrome P-450 molecules are provided. The use of DNA constructs containing such molecules to transform plants is described, as are transgenic plants exhibiting increased resistance to phenylurea herbicides. Methods of using such DNA constructs and transformed plants are provided.

47 Claims, 5 Drawing Sheets

(2 of 5 Drawing Sheet(s) Filed in Color)

US 6,121,512

CYTOCHROME P-450 CONSTRUCTS AND METHOD OF PRODUCING HERBICIDE-RESISTANT TRANSGENIC PLANTS

FIELD OF THE INVENTION

The present invention relates to DNA encoding novel cytochrome P-450 molecules, and the transformation of cells with such DNA. These DNA sequences may be used in methods of producing plants with an altered ability to metabolize chemical compounds, such as phenylurea herbicides.

BACKGROUND OF THE INVENTION

Cytochrome P-450 (P-450) monooxygenases are ubiquitous hemoproteins present in microorganisms, plants and animals. Comprised of a large and diverse group of isozymes, P450s mediate a great array of oxidative reactions using a wide range of compounds as substrates, and including biosynthetic processes such as phenylpropanoid, fatty acid, and terpenoid biosynthesis; metabolism of natural products; and detoxification of foreign substances (xenobiotics). See e.g., Schuler, *Crit. Rev. Plant Sci.* 15:235–284 (1996). In a typical P-450 catalyzed reaction, one atom of molecular oxygen ($O_2$) is incorporated into the substrate, and the other atom is reduced to water by NADPH. For most eucaryotic P-450s, NADPH:cytochrome P-450 reductase, a membrane-bound flavoprotein, transfers the necessary two electrons from NADPH to the P-450 (Bolwell et al, *Phytochemistry* 37: 1491–1506 (1994)).

Frear et al. (Phytochemistry 8:2157–2169 (1969)) demonstrated the metabolism of monuron by a mixed-function oxidase located in a microsomal fraction of cotton seedlings. Further evidence has accumulated supporting the involvement of P-450s in the metabolism and detoxification of numerous herbicides representing several distinct classes of compounds (reviewed in Bolwell et al., 1994; Schuler, 1996). Differential herbicide metabolizing P-450 activities are believed to represent one of the mechanisms that enables certain crop species to be more tolerant of a particular herbicide than other crop or weedy species.

SUMMARY OF THE INVENTION

A first aspect of the present invention is an isolated DNA molecule comprising SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17; or DNA sequences which encode an enzyme of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18; or DNA sequences which have at least about 90% sequence identity to the above DNA and which encode a cytochrome P450 enzyme; and DNA sequences which differ from the above DNA due to the degeneracy of the genetic code.

A further aspect of the present invention is a cytochrome p450 enzyme having an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

A further aspect of the present invention is an isolated DNA molecule comprising SEQ ID NO:1; DNA sequences which encode an enzyme of SEQ ID NO:2; DNA sequences which have at least about 90% sequence identity to the above DNA and which encode a cytochrome P450 enzyme; and DNA sequences which differ from the above DNA due to the degeneracy of the genetic code.

A further aspect of the present invention is a cytochrome p450 peptide of SEQ ID NO:2.

A further aspect of the present invention is a DNA construct comprising a promoter operable in a plant cell and a DNA segment encoding a peptide of SEQ ID NO:2 downstream from and operatively associated with the promoter.

A further aspect of the present invention is a method of making a transgenic plant cell having an increased ability to metabolize phenylurea compounds compared to an untransformed plant cell. The plant cell is transformed with an exogenous DNA construct comprising a promoter operable in a plant cell and a DNA sequence encoding a peptide of SEQ ID NO:2. Transformed plants, seed and progeny of such plants are also aspects of the present invention.

A further aspect of the present invention is a transgenic plant having an increased ability to metabolize phenylurea compounds. Such transgenic plants contain exogenous DNA encoding a peptide of SEQ ID NO:2.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
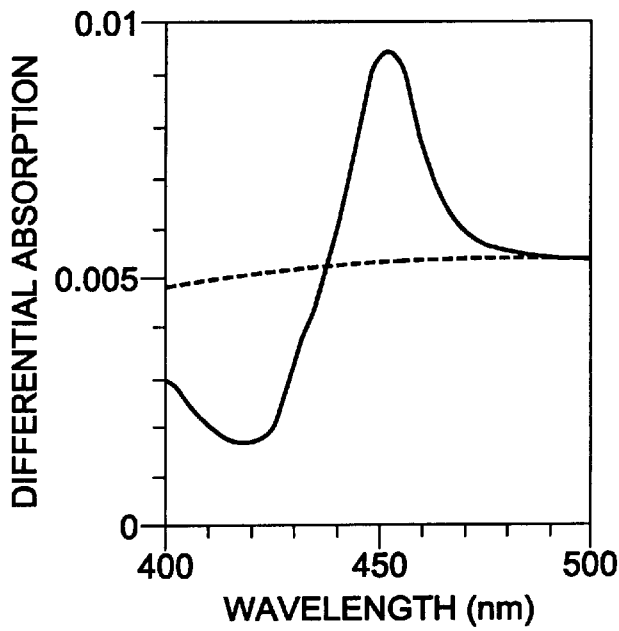
FIG. 1 depicts dithionite-reduced carbon monoxide difference spectra, where the solid line represents microsomes isolated from yeast transformed with CYP71A10, and the dotted line shows the difference spectra from yeast transformed with control vector V-60. Microsomal protein concentration was 1 mg/ml.

1. Overview of the Present Research:

The present inventors utilized a strategy based on the random isolation and screening of soybean cDNAs encoding cytochrome P-450 (P-450) isozymes to identify P-450 isozymes involved in herbicide metabolism. Eight full-length and one near full-length P-450 cDNAs representing eight distinct P-450 families were isolated using polymerase chain reaction (PCR)-based technologies (SEQ ID NOS:1, 3, 5, 7, 9, 11, 13, 15 and 17). Five of these soybean P-450 cDNAs were successfully overexpressed in yeast, and microsomal fractions generated from these strains were tested for their potential to mediate the metabolism of ten herbicides and one insecticide. In vitro enzyme assays showed that the gene product of one heterologously expressed P-450 cDNA (CYP71A10) (SEQ ID NO:1) specifically mediated the metabolism of phenylurea herbicides, converting four herbicides of this class (fluometuron, linuron, chlortoluron, and diuron) into more polar metabolites. Analyses of the metabolites indicate that the CYP71A10 encoded enzyme functions primarily as an N-demethylase with regard to fluometuron, linuron and diuron, and as a ring-methyl hydroxylase when chlortoluron is the substrate. In vivo assays using excised leaves demonstrated that all four herbicides were more readily metabolized in CYP71A10-transformed tobacco in comparison to control plants.

Shiota et al. reported that fused constructs derived from the rat CYP1A1 and yeast NADPH-cytochrome P-450 oxidoreductase cDNAs conferred chlortoluron resistance in tobacco by enhancing herbicide metabolism (Shiota et al., *Plant Physiol.* 106:17–23 (1994)). In another study, a chloroplast-targeted, bacterial CYP105A1 expressed in tobacco catalyzed the toxification of R7402, a sulfonylurea pro-herbicide (O'Keefe et al., *Plant Physiol.* 105:473–482 (1994)). The cloning and heterologous expression of an endogenous plant P450 gene that is potentially involved in herbicide metabolism was reported by Pierrel et al., *Eur. J. Biochem.* 224:835–844 (1994), where a trans-cinnamic acid hydroxylase cDNA (CYP73A1) isolated from artichoke and expressed in yeast catalyzed the ring-methyl hydroxylation of chlortoluron. In vivo experiments with artichoke tubers, however, demonstrated that the ring-methyl hydroxy metabolite represented only a minor portion of the metabolites produced and that the major metabolite was demethylated chlortoluron (Pierrel et al., 1994). This together with the observation that the turnover number of the heterologously expressed enzyme was very low (0.014/min), suggested that CYP73A1 plays a minimal role in chlortoluron metabolism in vivo. U.S. Pat. No. 5,349,127 to Dean et al. discloses the use of DNA encoding certain P450 enzymes, isolated from *Streptomyces griseolus*, to produce transformed plants with increased metabolism of certain compounds. (All U.S. patents referred to herein are intended to be incorporated herein in their entirety.)

Although the role of P-450 enzymes in catalyzing the metabolism of a variety of herbicides has been documented, little progress has been made in the identification of the endogenous plant P-450s that are responsible for degrading these compounds. Protein purification of specific isozymes involved in the metabolism of a specific herbicide has been hindered by the instability of the enzymes, their low concentrations in most plant tissues, and difficulties in the reconstitution of active complexes from solubilized components. Furthermore, any given plant tissue may possess dozens, if not hundreds, of unique P-450 isozymes, complicating the purification to homogeneity of a particular isozyme. Because plants have only been exposed to phenylurea herbicides during the past few decades, it is unlikely that enzymes have evolved solely for the purposed of metabolizing this class of xenobiotics.

2. Use of CYP71A10 to Produce Phenylurea-Resistant Plants:

The present invention provides materials and methods useful in producing transgenic plant cells and plants with increased resistance to phenylurea herbicides. Increased herbicide resistance, as used herein, refers to the ability of a plant to withstand levels of an herbicide that have a negative impact on wild-type (untransformed) plants of the same species and/or variety. Resistance, as used herein, does not necessarily mean that the resistant plant is completely unaffected by exposure to the herbicide; rather, resistant plants suffer less extensive or less severe damage than comparable wild-type plants. Methods of assessing the extent and/or severity of herbicide impact will vary depending on the particular plant and the particular herbicide being tested; such assessment methods will be apparent to those skilled in the art. The negative effects of a herbicide may be evidenced by the complete arrest of plant growth, or by an inhibition in the rate or amount of growth. Additionally, methods of the present invention may be used to decrease herbicide residues in plants, even where the amounts of herbicides present in the plant do not cause an appreciable negative effect on the plant as a whole.

Increased resistance to a herbicide can be due to an increased ability to metabolize a herbicide to less harmful metabolites. Accordingly, plants of the present invention which exhibit increased resistance to a herbicide may also be described as having an increased ability to metabolize the starting herbicidal compound, where the metabolites are less harmful to the plant than the starting compound.

In the examples provided herein, yeast microsomes and transgenic tobacco plants expressing the CYP71A10 peptide (SEQ ID NO:2) and exposed to various phenylurea herbicides produced the same degradation products that have previously been observed when these same compounds have been incubated with metabolically active plant microsomes. These results indicate that the CYP71A10 peptide plays a role in the effective metabolism of phenylurea herbicides.

The present examples demonstrate that the overexpression of a CYP71A10 peptide of SEQ ID NO:2 in tobacco enhanced the plant's capacity to metabolize all four phenylurea herbicides tested, and that appreciable levels of tolerance were conferred to linuron and chlortoluron. Fluometuron was the most actively metabolized compound in both the yeast and transgenic plant systems, yet the enhancement in tolerance to this herbicide at the whole plant level was not as great as for linuron and chlortoluron. While not wishing to be held to a single theory, the present inventors surmise that the lack of correlation between the rate of herbicide metabolism and herbicide tolerance may be explained by the differential toxicities of the various phenylurea derivatives produced in the CYP71A10-transformed tobacco. Consistent with this hypothesis are the previous observations that N-demethyl derivatives of fluometuron, diuron and chlortoluron are only moderately less toxic than their parent compounds (Rubin and Eshel, *Weed Sci.* 19:592–594 (1971); Dalton et al., *Weeds* 14:31–33 (1966); Ryan and Owen, *Proc. Brit. Crop Prot. Conf. Weeds* 1:317–324 (1982)). In contrast, linuron is a 10-fold greater inhibitor of the Hill-reaction than N-demethyl linuron (Suzuki and Casida, *J. Agric. Food Chem.* 29:1027–1033 (1981)), and the hydroxylated and the didemethlayed derivatives of chlortoluron are considered to be nonherbicidal (Ryan and Owen, 1982).

The present inventors found that the relative rates of herbicide metabolism in leaves of CYP71A10-transformed tobacco and in yeast microsomes assayed in vitro were similar (see Tables 4 and 5). With the exception of the transgenic plant leaves showing a somewhat greater metabolic activity against chlortoluron than was apparent in the yeast microsomal assays, both systems followed the general order of metabolism of fluometuron$\geq$linuron>chlortoluron>diuron. These results indicate that expression of a test plant P-450 in yeast and quantification of the metabolism of a test compound using yeast microsomes, is a suitable system for screening plant P-450s for their metabolic function, and for their potential usefulness in the production of transgenic plants with altered metabolism of chemical compounds such as herbicides and insecticides.

The present inventors have shown that the random isolation of P-450 cDNAs with subsequent heterologous expression in yeast is an effective strategy to characterize cDNAs whose product is capable of affecting the metabolism of a test compound. This approach is useful in characterizing the substrates (both natural and artificial) affected by a P-450, in determining the function of P-450 genes whose catalytic activities remain unclear, and in screening P-450s for the ability to increase or decrease the metabolism of a test compound. A particularly useful aspect of this method is the ability to screen isolated P-450s for their effects on the metabolism by plants of herbicides, insecticides, or other chemical compounds. Increased metabolism may result in enhanced resistance to the effects of a compound (where the metabolites are less harmful than the starting compound), or in increased sensitivity to the effects of a compound (where one or more metabolites are more toxic than the starting compound; see O'Keefe et al., 1994).

3. DNA Constructs:

Those familiar with recombinant DNA methods available in the art will recognize that one can employ a cDNA molecule (or a chromosomal gene or genomic sequence) encoding a P-450 peptide, joined in the sense orientation with appropriate operably linked regulatory sequences, to construct transgenic cells and plants. (Those of skill in the art will also recognize that appropriate regulatory sequences for expression of genes in the sense orientation include any one of the known eukaryotic translation start sequences, in addition to the promoter and polyadenylation/transcription termination sequences described herein). Appropriate selection of the encoded P-450 peptide will provide transformed plants characterized by altered (enhanced or retarded) metabolism of phenylurea compounds.

DNA constructs, or "transcription cassettes," of the present invention include, 5' to 3' in the direction of transcription, a promoter as discussed herein, a DNA sequence as discussed herein operatively associated with the promoter, and, optionally, a termination sequence including stop signal for RNA polymerase and a polyadenylation signal for polyadenylase. All of these regulatory regions should be capable of operating in the cells of the tissue to be transformed. Any suitable termination signal may be employed in carrying out the present invention, examples thereof including, but not limited to, the nopaline synthase (nos) terminator, the octapine synthase (ocs) terminator, the CaMV terminator, or native termination signals derived from the same gene as the transcriptional initiation region or derived from a different gene. See, e.g., Rezian et al. (1988) supra, and Rodermel et al. (1988), supra.

The term "operatively associated," as used herein, refers to DNA sequences on a single DNA molecule which are associated so that the function of one is affected by the other. Thus, a promoter is operatively associated with a DNA when it is capable of affecting the transcription of that DNA (i.e., the DNA is under the transcriptional control of the promoter). The promoter is said to be "upstream" from the DNA, which is in turn said to be "downstream" from the promoter.

The transcription cassette may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide, such as antibiotics, toxins, heavy metals, or the like; may provide complementation, by imparting prototrophy to an auxotrophic host; or may provide a visible phenotype through the production of a novel compound in the plant.

The various fragments comprising the various constructs, transcription cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature as exemplified by J. Sambrook et al., Molecular Cloning, A Laboratory Manual (2d Ed. 1989)(Cold Spring Harbor Laboratory).

Vectors which may be used to transform plant tissue with nucleic acid constructs of the present invention include both Agrobacterium vectors and ballistic vectors, as well as vectors suitable for DNA-mediated transformation.

4. Promoters:

The term 'promoter' refers to a region of a DNA sequence that incorporates the necessary signals for the efficient expression of a coding sequence. This may include sequences to which an RNA polymerase binds but is not limited to such sequences and may include regions to which other regulatory proteins bind together with regions involved in the control of protein translation and may include coding sequences.

Promoters employed in carrying out the present invention may be constitutively active promoters. Numerous constitutively active promoters which are operable in plants are available. A preferred example is the Cauliflower Mosaic Virus (CaMV) 35S promoter which is expressed constitutively in most plant tissues. Use of the CaMV promoter for expression of recombinant genes in tobacco roots has been well described (Lam et al., "Site-Specific Mutations Alter In Vitro Factor Binding and Change Promoter Expression Pattern in Transgenic Plants", *Proc. Nat. Acad. Sci. USA* 86, pp. 7890–94 (1989); Poulsen et al. "Dissection of 5' Upstream Sequences for Selective Expression of the Nicotiana plumbaginifolia rbcS-8B Gene", *Mol. Gen. Genet.* 214, pp. 16–23 (1988)). In the alternative, the promoter may be a tissue-specific promoter or a promoter that is expressed temporally or developmentally. See, e.g., U.S. Pat. No. 5,459,252 to Conkling et al.; Yamamoto et al., *The Plant Cell*, 3:371 (1991). In methods of transforming plants to alter the effects of herbicides or to decrease residual amounts of herbicides or pesticides in plants, selection of a suitable promoter will vary depending on the plant species, the specific chemical compound used as a herbicide or pesticide, and the time and method of applying the chemical compound to the plant or plant crop, as will be apparent to those skilled in the art.

5. Selectable Markers:

The recombinant DNA molecules and vectors used to produce the transformed cells and plants of this invention may further comprise a dominant selectable marker gene. Suitable dominant selectable markers include, inter alia, antibiotic resistance genes encoding neomycin phosphotransferase (NPTII), hygromycin phosphotransferase (HPT), and chioramphenicol acetyltransferase (CAT). Another well-known dominant selectable marker suitable is a mutant dihydrofolate reductase gene that encodes methotrexate-resistant dihydrofolate reductase. DNA vectors containing suitable antibiotic resistance genes, and the corresponding antibiotics, are commercially available. Transformed cells are selected out of the surrounding population of non-transformed cells by placing the mixed population of cells into a culture medium containing an appropriate concentration of the antibiotic (or other compound normally toxic to the untransformed cells) against which the chosen dominant selectable marker gene product confers resistance. Thus, only those cells that have been transformed will survive and multiply.

A further aspect of the present invention is use of the identified P-450 coding sequences as a selectable marker gene. A DNA construct comprising a sequence encoding a P-450 known to increase resistance to a compound (such as SEQ ID NO:2) is utilized to transform cells, in accordance with methods known in the art. Those cells that subsequently exhibit resistance to the compound are indicated as transformed. Such constructs may be used to verify the success of a transformation technique or to select transformed cells of interest.

6. Sequence Similarity and Hybridization Conditions:

Nucleic acid sequences employed in carrying out the present invention include those with sequence similarity to SEQ ID NO:1, 3, 5, 7, 9, 11, 13, 15 or 17, and encoding a protein having P-450 enzymatic activity. This definition is intended to encompass natural allelic variants and minor sequence variations in the nucleic acid sequence encoding a P-450 molecule, or minor sequence variations in the amino acid sequence of the encoded product. Thus, DNA sequences that hybridize to DNA of SEQ ID NO:1, 3, 5, 7, 9, 11, 13, 15 or 17 and code for expression of a P-450 enzyme, particularly a plant P-450 enzyme, may also be employed in carrying out aspects of the present invention. The nomenclature for P-450 genes is based on amino acid sequence identity; methods of determining sequence similarity are well-known to those skilled in the art. Typically, sequences sharing >40% identity are placed in the same family, >55% identity defines members of the same subfamily, and sequences that display >97% identity are assumed to represent allelic variants. Conditions which permit other DNA sequences which code for expression of a protein having P-450 enzymatic activity to hybridize to DNA of SEQ ID NO:1, 3, 5, 7, 9, 11, 13, 15 or 17, or to other DNA sequences encoding the protein given as SEQ ID NO:2, 4, 6, 8, 10, 12, 14, 16 or 18 can be determined in a routine manner. For example, hybridization of such sequences may be carried out under conditions of reduced stringency or even stringent conditions (e.g., conditions represented by a wash stringency of 0.3 M NaCl, 0.03 M sodium citrate, 0.1% SDS at 60° C. or even 70° C. to DNA encoding the protein given as SEQ ID NO:2 herein in a standard in situ hybridization assay. See J. Sambrook et al., Molecular Cloning, A Laboratory Manual (2d Ed. 1989) (Cold Spring Harbor Laboratory)). In general, such sequences will be at least 65% similar, 75% similar, 80% similar, 85% similar, 90% similar, 93% similar, 95% similar, or even 97% or 98% similar, or more, with the sequence given herein as SEQ ID NO:1, or DNA sequences encoding proteins of SEQ ID NO:2. (Determinations of sequence similarity are made with the two sequences aligned for maximum matching; gaps in either of the two sequences being matched are allowed in maximizing matching. Gap lengths of 10 or less are preferred, gap lengths of 5 or less are more preferred, and gap lengths of 2 or less still more preferred.)

As used herein, the term 'gene' refers to a DNA sequence that incorporates (1) upstream (5') regulatory signals including a promoter, (2) a coding region specifying the product, protein or RNA of the gene, (3) downstream (3') regions including transcription termination and polyadenylation signals and (4) associated sequences required for efficient and specific expression.

The DNA sequence of the present invention may consist essentially of a sequence provided herein (SEQ ID NO:1, 3, 5, 7, 9, 11, 13, 15 or 17), or equivalent nucleotide sequences representing alleles or polymorphic variants of these genes, or coding regions thereof.

Use of the phrase "substantial sequence similarity" in the present specification and claims means that DNA, RNA or amino acid sequences which have slight and non-consequential sequence variations from the actual sequences disclosed and claimed herein are considered to be equivalent to the sequences of the present invention. In this regard, "slight and non-consequential sequence variations" mean that "similar" sequences (i.e., the sequences that have substantial sequence similarity with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

DNA sequences provided herein can be transformed into a variety of host cells. A variety of suitable host cells, having desirable growth and handling properties, are readily available in the art.

Use of the phrase "isolated" or "substantially pure" in the present specification and claims as a modifier of DNA, RNA, polypeptides or proteins means that the DNA, RNA, polypeptides or proteins so designated have been separated from their in vivo cellular environments through the efforts of human beings.

As used herein, a "native DNA sequence" or "natural DNA sequence" means a DNA sequence which can be isolated from non-transgenic cells or tissue. Native DNA sequences are those which have not been artificially altered, such as by site-directed mutagenesis. Once native DNA sequences are identified, DNA molecules having native DNA sequences may be chemically synthesized or produced using recombinant DNA procedures as are known in the art. As used herein, a native plant DNA sequence is that which can be isolated from non-transgenic plant cells or tissue.

7. Transformed Plants:

Methods of making recombinant plants of the present invention, in general, involve first providing a plant cell capable of regeneration (the plant cell typically residing in a tissue capable of regeneration). The plant cell is then transformed with a DNA construct comprising a transcription cassette of the present invention (as described herein) and a recombinant plant is regenerated from the transformed plant cell. As explained below, the transforming step is carried out by techniques as are known in the art, including but not limited to bombarding the plant cell with microparticles carrying the transcription cassette, infecting the cell with an Agrobacterium tumefaciens containing a Ti plasmid carrying the transcription cassette, or any other technique suitable for the production of a transgenic plant.

Numerous Agrobacterium vector systems useful in carrying out the present invention are known. For example, U.S. Pat. No. 4,459,355 discloses a method for transforming susceptible plants, including dicots, with an Agrobacterium strain containing the Ti plasmid. The transformation of woody plants with an Agrobacterium vector is disclosed in U.S. Pat. No. 4,795,855. Further, U.S. Pat. No. 4,940,838 to Schilperoort et al. discloses a binary Agrobacterium vector (i.e., one in which the Agrobacterium contains one plasmid having the vir region of a Ti plasmid but no T region, and a second plasmid having a T region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell, and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Christou et al., U.S. Pat. No. 5,015,580. When using ballistic transformation procedures, the transcription cassette may be incorporated into a plasmid capable of replicating in or integrating into the cell to be transformed. Examples of microparticles suitable for use in such systems include 1 to 5 $\mu$m gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art. Fusion of tobacco protoplasts with DNA-containing liposomes or via electroporation is known in the art. (Shillito et al., "Direct Gene Transfer to Protoplasts of Dicotyledonous and Monocotyledonous Plants by a Number of Methods, Including Electroporation", Methods in Enzymology 153, pp. 313–36 (1987)).

As used herein, transformation refers to the introduction of exogenous DNA into cells, so as to produce transgenic cells stably trnnsformed with the exogenous DNA. Transformed plant cells are induced to regenerate intact plants through application of cell and tissue culture techniques that are well known in the art. The method of plant regeneration is chosen so as to be compatible with the method of transformation. The stable presence and the orientation of the exogenous DNA in transgenic plants can be verified by Mendelian inheritance of the DNA sequence, as revealed by standard methods of DNA analysis applied to progeny resulting from controlled crosses.

Plants of horticultural or agronomic utility, such as vegetable or other crops, can be transformed according to the present invention using techniques available in the art. A plant suitable for use in the present methods is *Nicotiana tabacum*, or tobacco. Any strain or variety of tobacco may be used. Additional plants (both monocots and dicots) which may be employed in practicing the present invention include, but are not limited to, potato (*Solanum tuberosum*), soybean (*Glycine max*), tomato (*Lycopersicon esculentun*), peanuts (*Arachis hypogaea*), cotton (*Gossypium hirsutum*), green beans (*Phaseolus vulgaris*), lima beans (*Phaseolus limensis*), peas (*Lathyrus spp.*)cassava (*Manihot esculenta*), coffee (*Cofea spp.*), pineapple (*Ananas comosus*), citrus trees (*Citrus spp.*), banana (*Musa spp.*), corn (*Zea mays*), oilseed rape (*Brassica napus*), wheat, oats, barley, rye and rice. Thus, an illustrative category of plants which may be used to practice aspects of the present invention are the dicots, and a more particular category of plants which may be used to practice the present invention are members of the family Solanacae.

The methods of the present invention can further be practiced with turfgrass, including cool season turfgrasses and warm season turfgrasses. Examples of cool season turfgrasses are Bluegrasses (Poa L.), such as Kentucky Bluegrass (*Poa pratensis* L.), rough Bluegrass (*Poa trivialis* L.), Canada Bluegrass (*Poa compressa* L.), Annual Bluegrass (*Poa annua* L.), Upland Bluegrass (*Poa glaucantha* Gaudin), Wood Bluegrass (*Poa nemoralis* L.). and Bulbous Bluegrass (*Poa bulbosa* L.); the Bentgrasses and Redtop (Agrostis L.), such as Creeping Bentgrass (*Agrostis palustris* Huds.), Colonial Bentgrass (*Agrostis tenius* Sibth.), Velvet Bentgrass (*Agrostis canina* L.), South German Mixed Bentgrass (Agrostis L.), and Redtop (*Agrostis alba* L.); the Fescues (Festuca L.), such as Red Fescue (*Festuca rubra* L.), Chewings Fescue (*Festuca rubra* var. *commutata* Gaud.), Sheep Fescue (*Festuca ovina* L.), Hard Fescue (*Festuca ovina* var. *duriuscula* L. Koch), Hair Fescue (*Festuca capillata* Lam.), Tall Fescue (*Festuca arundinacea* Schreb.), Meadow Fescue (*Festuca eaitor* L.); the Rye grasses (Lolium L.), such as Perennial Ryegrass (*Lolium perenne* L.), Italian Ryegrass (*Lolium multiflorum* Lam.); the Wheatgrasses (Agropyron Gaertn.), such as Fairway Wheatgrass (*Agropyron cristatum* L. Gaertn.), Western Wheatgrass (*Agropyron smithii* Rydb.). Examples of warm season turfgrasses are the Bermudagrasses (Cynodon L. C. Rich), the Zoysiagrasses (Zoysia Willd.), St. Augustinegrasses (*Stenotaphrum secundatum* (Walt.) Kuntze), Centipedegrass (*Eremochioa ophiuroides* (Munro.) Hack.), Carpetgrass (Axonopus Beauv.), Bahiagrass (*Paspalum notatum* Flugge.), Kikuyugrass (*Pennisetum clandestinum* Hochst. ex Chiov.), Buffalograss (*Buchloe dactyloides* (Nutt.) Engelm.), Blue Grama (*Bouteloua gracilis* (H.B.K.) Lag. ex Steud.), Sideoats Grama (*Bouteloua curtipendula* (Michx.) Torr.), and Dichondra (Dichondra Forst.).

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the transcription cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to provide homozygous second generation (or T2) transformed plants, and the T2 plants further propagated through classical breeding techniques. A dominant selectable marker (such as nptII) can be associated with the transcription cassette to assist in breeding.

As used herein, a crop comprises a plurality of plants of the same genus or species, planted together in an agricultural field. By "agricultural field" is meant a common plot of soil or a greenhouse. Thus, the present invention provides a method of producing a crop of plants having altered metabolism of chemical compounds (such as a phenylurea herbicide), and thus having altered resistance to the chemical compound, compared to a crop of non-transformed plants of the same genus or species, or variety.

Where a crop comprises a plurality of transgenic plants with increased resistance to phenylurea compounds according to the present invention, such compounds may be used as post-emergent herbicides to control undesirable plant species. Accordingly, a method of using phenylurea compounds as post-emergent herbicides according to the present invention comprises planting a plurality of transformed plant seed (or transformed plants) with enhanced resistance to a phenylurea herbicide, and applying that herbicide to the field after the germination and emergence of at least some of said transformed plant seed (or following the planting of transformed plants). Application of the phenylurea herbicide will selectively impact non-resistant plants.

9. Microbial Decontamination:

Microbial cells useful for degrading phenylurea compounds, which cells contain and express a heterologous DNA molecule encoding a P450 enzyme that enhances the metabolism of the phenylurea compound in the microbial cell (e.g., a peptide of SEQ ID NO:2), are a further aspect of the present invention. Suitable host microbial cells include soil microbes (i.e., those which grow in the soil) transformed to express a P450 enzyme that enhances the metabolism of one or more phenylurea compounds by the host cell. Suitable microbes include bacteria (such as Agrobacterium, Bacillus, Streptomyces, Nocardia, etc.), fungi (including yeasts), and algae. Microbes can be selected, by methods known in the art of soil microbiology, to correspond to those which are typically found in the substrate to be treated. Liquids which are contaminated with phenylurea compounds may be contacted to transformed microorganisms by passing the contaminated liquid through a bioreactor which contains the microorganism. Numerous suitable bioreactor designs are known in the art. A microbial host particularly suitable for bioreactors is yeast.

Combination treatments utilizing aspects of the present invention involve the application of a phenylurea compound in a location such as an agricultural field (e.g., as a herbicide), and subsequent application of a transformed microbe as described above in an amount effective to degrade residual applied herbicide. Application of the herbicide may be carried out in accordance with known techniques.

The examples which follow are set forth to illustrate the present invention, and are not to be construed as limiting thereof.

EXAMPLE 1

Materials and Methods a. Substrates

Phenyl-U-[$^{14}$C] fluometuron, phenyl-U-[$^{14}$C] chlortoluron, phenyl-U-[$^{14}$C] metolachlor, phenyl-U-[14C] prosulfuron, pyrimidinyl-2- diazinon, and phenyl-U-[$^{14}$C] alachlor were provided by Novartis (Greensboro, N.C.); phenyl-U-[$^{14}$C] bentazon was donated by BASF (Research Triangle Park, North Carolina); phenyl-U-[$^{14}$C] linuron, phenyl-U-[$^{14}$C] diuron, and carbonyl-[$^{14}$C] metribuzin were a gift from DuPont de Nemours (Wilmington, Del.); carboxyl-[$^{14}$C] imazaquin was provided by American Cyanamid (Princeton, N.J.).

b. Isolation of P-450 cDNAs

Random amplification of partial cDNAs encoding P-450 enzymes was conducted essentially as described by Meijer et al., *Plant Mol. Biol.* 22:379–383 (1993), using a soybean (*Glycine max* cv Dare) leaf cDNA library as the template (Dewey et al., *Plant Cell* 6:1495–1507 (1994)). Briefly, degenerate inosine-containing primers were synthesized based on the highly conserved heme-binding region. The precise sequences of these primers are described in Meijer et al. (1993). An oligo-dT primer complementary to the poly (A) tail of the cDNA clones was used in conjunction with the degenerate primers in PCR amplification assays. Amplification products were cloned into the T-tailed pCRII plasmid (Invitrogen, San Diego, Calif.) and DNA sequence analysis of the first 300–400 base pairs downstream of the conserved region was used to establish whether a given amplification product represented a true P-450 cDNA.

To recover full-length versions of the partial cDNAs, a primer (5'-TGTCTAACTCCTTCCTTTTC-3') (SEQ ID NO:19) complementary to the pYES2 vector (the vector into which the soybean cDNA library was cloned) and a downstream primer corresponding to a segment of the 3' untranslated region for each of the unique P-450 cDNAs were used in PCR reactions using the same soybean cDNA library as the template. PCR products were again cloned into the pCRII plasmid and the entire DNA sequence was determined for the largest cDNA amplified for each unique soybean P-450.

To isolate full-length versions of the respective P-450 ORFs without including any of the 5' untranslated region (which has been shown to potentially impede gene expression in yeast (Pompon, *Eur. J. Biochem.* 177:285–293 (1988)), an additional PCR reaction was performed with two gene-specific primers. The forward primers contained a BamHI restriction site immediately followed by the ATG start codon, and the next 14–15 bases of the reading frame; the downstream primer was again specific for the 3' untranslated regions of the respective genes and included sequences specifying either EcoRI, KpnI, and SacI to facilitate subcloning of the P450 cDNAs into the yeast expression vector, pYeDP60 (V-60; Urban et al., *Biochimie* 72:463472 (1990)).

All PCR reactions, with the exception of the initial amplification of the partial P-450 cDNAs (see Meijer et al. (1993)), contained 0.2 ng/μl template, 2 μM of each primer, 200 μM of each dNTP, and 1.5 mM $MgCl_2$ in a final reaction volume of 50 μl. Amplification was initiated by the addition of 1.5 U EXPAND# High Fidelity enzyme mix using conditions described by the manufacturer (Boeringer Mannheim). DNA sequence was determined by the chain termination method (Sanger et al., *Proc. Natl. Acad. Sci. USA* 74:5463–5467 (1977)) using fluorescent dyes (Applied Biosystems, Foster City, Calif.). DNA and predicted amino acid sequences were analyzed using the BLAST algorithm and the GAP program (University of Wisconsin, Madison, Genetics Computing Group software package).

c. P-450 cDNA Expression in Yeast

Yeast transformation was performed as described by Geitz et al., *Nucleic Acids Research* 20:1425 (1992). Media composition, culturing conditions, galactose induction, and microsomal preparations were conducted according to Pompon et al., *Methods Enzymol.* 272:51–64 (1995), using a culture volume of 250 ml. Microsomal protein was quantified spectrophotometrically using the method of Waddell, *J. Lab. Clin. Med.* 48:311–314 (1956), using bovine albumin as a standard. Dithionite-reduced, carbon monoxide difference spectra was obtained as previously outlined (Estabrook and Werringloer, *Methods Ennzmol.* 52:212–220 (1978)) using a Shimadzu Recording Spectrophotometer UV-240 (Shimadzu, Kyoto, Japan). P-450 protein concentrations of yeast microsomes were calculated using a millimolar extinction coefficient of 91 (Omura and Sato, *J. Biol. Chem.*, 239:2370–2378 (1964)).

d. In vitro Herbicide Metabolism Assays

Yeast microsomes enriched for a discrete soybean P-450 isozyme were assayed for their capacity to metabolize the ten herbicides and one insecticide listed in Table 3. The reaction mixtures contained 10,000 DPM (100–200 ng) radiolabeled substrate, 0.75 mM NAPDH, 2.5 mg/ml microsomal protein. Total reaction volumes were adjusted to 150 μl with 50 mM phosphate buffer (pH 7.1). The mixtures were incubated under light for 45 minutes at 27° C., arrested with 50 μl acetone and centrifitiged at 14 000×g for 2 minutes. Fifty microliters of the supernatants containing radiolabeled alachlor, metolachlor, metribuzin, prosulfuron, chlortoluron, diuron, fluometuron, linuron, or diazinon were spotted onto 250 micron Whatman K6F silica plates. Radiolabeled bentazon and imazaquin-containing samples were spotted onto 200 micron Whatman LKC18F silica gel reversed-phase plates. All plates were developed in a benzene/acetone 2:1 (v/v) solvent system with the exception of prosulfaron, developed in toluene/acetone/acetic acid, 75:20:5 (v/v/v), and bentazon and imazaquin, developed in methanol/75 mM sodium acetate 40:60 (v/v). The developed plates were scanned with a Bioscan System 400 imaging scanner (Bioscan, Washington, D.C.), and the production of metabolites was determined based on the chromatographic profiles. For microsomes containing the expressed CYP71A10 enzyme, control experiments were also conducted to measure the NADPH-dependency, and the inhibitory effects of CO. CO treatment of the sample was achieved by gentle bubbling of the gas through the reaction mixture for 2 minutes immediately before the assay was initiated by the addition of NADPH.

e. Enzyme Kinetics

Substrate conversion was quantified by a combination of TLC analysis and scintillation spectrometry. The location of the metabolic products on the TLC plates was identified using an imaging scanner, the bands were scraped and analyzed by scintillation spectrometry. The amount of metabolite produced was calculated based on specific activity and scintillation counts. Each assay was repeated at least twice. $K_m$ and $V_{max}$ values were estimated using nonlinear regression analysis.

f. Mass Spectral Analysis

The reaction components used in the in vitro fluometuron and linuron metabolism assays were scaled up 50-fold, and the reactions were allowed to proceed for 3 hours. The substrates and the metabolites were extracted 3 times with 20 ml ethyl acetate. The extracts were combined, evaporated to dryness, and the resulting pellet was resuspended in 1 ml acetone. The samples were purified twice using preparative TLC and imaging scanning as described above. Finally, the respective bands were scraped, the compounds were eluted with acetone and flash evaporated.

Fractions of interest were analyzed by liquid chromatography/mass spectrometry (LC/MS). Mass spectral measurements were made with a Finnigan TSQ 7000 triple quadruple mass spectrometer (QQQ) equipped with an Atmospheric Pressure Ionization (API) interface fitted with a pneumatically assisted electrospray head (Finnigan MAT, Brennan, Germany). The spray nozzle was operated at 5 kV in the positive ion mode and 4 kV in the negative ion mode. For sample introduction, the TSQ 7000 was equipped with a HPLC solvent delivery system (Perkin-Elmer 410 LC pump), a UV detector (Perkin-Elmer), a stream splitter set at 6:1 with the majority of the effluent flowing to a radioisotope flow monitor (IN/US β-RAM) and the other stream attached to the API interface. Samples were chromatographed on a reverse phase HPLC column (Inertsil 5 ODS2, 150×2 mm i.d.). The column was eluted at 0.4 ml/min with 95:5 of 0.1 % trifluoroacetic acid in water and 0.1% trifluoroacetic acid in methanol, respectively. Collision induced dissociation experiments (MS/MS) were conducted using argon gas with collision energy in the range of 17.5–30 eV at cell pressures of approximately 0.28 Pa. Signals were captured using a Finnigan 7000 data system.

g. NMR Analysis

Proton NMR measurements were made on a Bruker AMX-400 NMR spectrometer equipped with either a QNP or inverse probe set at 400.13 MHZ. Spectra were acquired at ambient temperature in acetonitrile-$d_3$. Chemical shifts were expressed as parts per million, relative to the resonance of residual acetonitrile protons at 1.93 ppm (δ).

h. Tobacco Transformation

A plant expression vector capable of mediating the constitutive expression of CYP71A10 was produced. The GUS open reading frame of the binary expression vector pBI121 (Clontech, Polo Alto, Calif.) was excised and replaced with the full length CYP71A10 reading frame. This placed the soybean gene under the transcriptional control of the strong constitutive CAMV 35S promoter. The resulting construct was used to transform Agrobacterium tumefaciens strain LBA 4404 (Holsters et al., *Mol. Gen. Genetics*, 163:181–187 (1988)). Excised leaf discs of Nicotiana tabacum cv SR1 were transformed using the Agrobacterium, and kanamycin-resistant plants were selected as described by Horsch et al. *Science*, 227:1229–1231 (1985). Primary transfornants were potted in a standard soil mixture, transferred to a greenhouse and their seed harvested upon maturation.

i. In vivo Herbicide Metabolism Assays

Seeds from primary transgenic tobacco plants transformed with CYP71A10 and control plants transformed with the pBI121 vector were grown in Petri dishes containing MS salts and 100 µg/ml kanamycin. At five weeks post-seeding, kanamycin-resistant plantlets were transplanted into pots containing soil and grown an additional two weeks. Single leaves of approximately 10 cm$^2$ in size were excised and their petioles inserted into 100 µl of H$_2$O containing radiolabeled herbicide. The leaves were placed in a growth chamber maintaining a temperature of 27° C. and incubated until the entire volume of the herbicide solution was drawn up by the transpirational stream of the leaves (about 3 hrs). The leaves were subsequently transferred into an Eppendorf tube containing distilled water and further incubated for a total of 14 hours.

[$^{14}$C]-labeled herbicide was extracted from the leaves by grinding for 5 minutes in 250 µl methanol with a plastic pellet pestle driven by an electric drill. After centrifugation for 3 minutes at 14,000 g, 75µl of the supernatant was spotted on a Whatman K6F silica plate and developed in a solvent system containing chloroforn/ethanol/acetic acid 135:10:15 (v/v/v). The separated herbicide derivatives were visualized using an imaging scanner. Substrate conversion was quantified based on the amount of herbicide absorbed, and the ratios of the parent compound and the produced metabolites determined from the TLC profiles.

j. Herbicide Tolerance

T$_1$ generation seeds from CYP71A10-transformed tobacco and pBI121-transformed control plants were placed onto Petri dishes containing MS salts and linuron (using its commercial formulation LOROX 50 DF) at active ingredient concentrations ranging from 0.25 to 3.0 µM. Chlortoluron was added at 0, 1.0, 5.0 and 10.0 µM concentrations using a 99.5% pure analytical standard. The Petri dishes were incubated in a growth chamber maintaining a constant temperature of 27° C. and a 16/8 hour light/dark cycle. The phytotoxic effects of the treatments were determined visually by comparison to control plants and plants grown in the absence of the herbicide. All treatments were repeated at least twice.

EXAMPLE 2

Isolation of P-450 cDNAs

To isolate cDNAs encoding P450s from soybean, the PCR strategy described by Meijer et al. (1993) was adapted, using a soybean leaf cDNA library as the template. Degenerate, inosine-containing PCR primers were constructed corresponding to the first nine codons encoding the conserved sequence FLPFGxGxRxCxG (x=any amino acid) (SEQ II NO:20), which represents an extension of the highly conserved FxxGxxxCxG motif (Bozak et al., Proc. Natl. Acad. Sci. USA 87:3904–3908 (1990)) (SEQ ID NO:21). Located near the C-terminal end of the protein, this motif defines the heme-binding region of the protein and may be regarded as a "signature" for P450 proteins. A second nonspecific primer complementary to the poly(A) tail of the cDNA clones was used in conjunction with these degenerate primers in a PCR amplification assay. PCR amplification products were cloned into a plasmid vector and analyzed by DNA sequencing. Of 86 randomly selected individuals that were sequenced, 15 clones representing 10 unique cDNAs were identified that possessed the conserved cysteine and glycine residues of the signature consensus (xCxG) (SEQ ID NO:22) immediately following the sequence defined by the degenerate PCR primers. Furthermore, homology searches of the major DNA and protein data bases revealed additional sequence identities to previously reported P-450 sequences for each of the ten unique soybean sequences (data not shown). Because this strategy only allows the recovery of sequence corresponding to the C-terminal portion of the proteins, additional PCR-based techniques were utilized to obtain cDNAs possessing the entire reading frames for each clone. Full length cDNAs were isolated for eight of the 10 individual clones and a near full length cDNA was isolated for an additional clone.

The eight full length and one near full length soybean P-450 cDNAs isolated are described in Table 1. The nomenclature for P-450 genes is based on amino acid sequence identity. Typically, sequences sharing >40% identity are placed in the same family, >55 % identity defines members of the same subfamily, and sequences that display >97% identity are assumed to represent allelic variants, although exceptions to these designations have been noted (Nelson et al., Pharmacogenetics, 6:141 (1996)). According to this system of nomenclature, all of the nine soybean cDNAs were able to be placed within existing P-450 gene families; however, three of the sequences (CYP82C1, CYP83D1 and CYP93C1) defined new subfamilies. Although an increasing number of P-450 gene products have been assigned specific enzymatic functions (reviewed in Schuler, 1996), none of the soybean cDNAs listed in Table 1 could be placed into families for which an in vivo function had been determined for any of its members.

In addition to the conserved heme-binding domain described previously, all of the predicted soybean polypeptides possess slight variations of the conserved sequence PEEFxPERF (SEQ ID NO:23) located approximately 30 amino acids forward of the heme-binding motif (Hallahan et al., Biochem. Soc. Trans. 21:1068–1073 (1993)). Also characteristic of microsomal P-450s is the presence of an N-terminal noncleavable signal sequence that serves as the membrane anchor. Immediately following this signal-anchor segment in most microsomal P-450s is a proline-rich region that is believed to form a hinge between the catalytic cytoplasmic domain and the hydrophobic membrane anchor (Halkier, Phytochemistry 43:1–21 (1996)). All of the present clones (except CYP97B2) encode proteins possessing predicted signal sequences; all individuals (except CYP97B2 and CYP82C1) contain readily identifiable proline-rich domains following the signal sequence (Table 1). It is the identification of both of these N-terminal motifs in the CYP83D1 encoded protein (but no Met codon) that indicates that this clone is nearly full length. Interestingly, instead of possessing a predicted signal sequence and proline-rich region, the N-terminus of the polypeptide encoded by clone CYP97B2 contains a motif characteristic of a chloroplast transit peptide (data not shown).

TABLE 1

Soybean P-450s Isolated Using Degenerate PCR Primers

| Name | GenBank Accession # | Length (amino acids) | Closest Match | Identity* % | Membrane Anchor | Proline-rich Region |
|---|---|---|---|---|---|---|
| CYP71A10 (SEQ ID NO: 1) | AF022157 | 513 | CYP71A1 | 51.7 | + | + |
| CYP71D10 (SEQ ID NO: 3) | AF022459 | 510 | CYP71D9 | 50.9 | + | + |
| CYP77A3 (SEQ ID NO: 5) | AF022464 | 513 | CYP77A1 | 69.8 | + | + |

TABLE 1-continued

Soybean P-450s Isolated Using Degenerate PCR Primers

| Name | GenBank Accession # | Length (amino acids) | Closest Match | Identity* % | Membrane Anchor | Proline-rich Region |
|---|---|---|---|---|---|---|
| CYP78A3 (SEQ ID NO: 7) | AF022463 | 523 | CYP78A2 | 53.1 | + | + |
| CYP82C1 (SEQ ID NO: 9) | AF022461 | 532 | CYP82A3 | 51.1 | + | − |
| CYP83D1** (SEQ ID NO: 11) | AF022460 | 516 | CYP71A1** | 45.7 | + | + |
| CYP93C1 (SEQ ID NO: 13) | AF022462 | 521 | CYP93B1 | 44.5 | + | + |
| CYP97B2 (SEQ ID NO: 15) | AF022457 | 576 | CYP97B1 | 80.8 | − | − |
| CYP98A2 (SEQ ID NO: 17) | AF022458 | 509 | CYP98A1 | 69.7 | + | + |

*Percent identity between the predicted amino acids sequences of the given soybean P-450 cDNA and the closest match identified from a BLAST search against the major gene and protein databases.
**Although this sequence shows a best match to CYP71A1, it matches poorly to some sequences of the CYP71B subfamily. As a result, the tree cluster program places it into the CYP83 family.

EXAMPLE 3

Expression of Soybean P-450 cDNAs in Yeast

Because superfluous 5' untranslated sequences from foreign genes have been shown to be capable of impeding gene expression in yeast (Pompon, 1988), an additional PCR reaction was performed on each clone that enabled the cloning of full length P-450 open reading frames (ORFs) into the yeast expression vector pYeDP60 (V-60) without including any of the endogenous 5' nontranslated flanking sequence (see Methods). For the near full length clone CYP83D1, the 5' primer was also designed to generate an "artificial" Met start codon and a Val second codon at the 5' end of the ORF. Expression in yeast of genes cloned into the V-60 vector is mediated by the strong, galactose-inducible GAL10-CYC1 promoter (Pompon et al., 1995).

Previous studies have revealed that the heterologous expression of P-450 cDNAs in yeast can be greatly enhanced in strains that have been engineered to overexpress endogenous NADPH-dependent cytochrome P-450 reductase (Pompon et al., 1995). In strain W(R), this was accomplished by exchanging the relatively weak endogenous cytochrome P-450 reductase promoter with the same GAL10-CYC1 promoter used in vector V-60 (Truan et al., Gene 125:49–55 (1993)). To maximize the heterologous expression of the soybean P-450 cDNAs in yeast, each of the constructs cloned into the V-60 vector was transformed into strain W(R) and microsomes were isolated from cultures that had been induced by galactose.

Reduced-CO difference spectroscopy provides a method to measure the effectiveness of expression of heterologous P-450s in yeast. Microsomal preparations corresponding to five of the soybean constructs (CYP71A10, CYP71D10, CYP77A3, CYP83D1 and CYP98A2) showed characteristic P-450 CO difference spectra with Soret peaks at 450 nm; the profile corresponding to CYP71A10 is shown in FIG. 1. No such peaks were observed for the remaining four clones. The specific P-450 content of the five positive microsomal preparations varied significantly, ranging from 11 pmol P-450/mg protein for construct CYP83D1 to 252 pmol P-450/mg for clone CYP77A3 as shown in Table 2.

TABLE 2

P-450 Content of Microsomes Isolated from Yeast Overexpressing Various Soybean CYPs

| Clone | CYP content (pmol mg$^{-1}$ protein) |
|---|---|
| CYP71A10 | 44 |
| CYP71D10 | 15 |
| CYP77A3 | 252 |
| CYP83D1 | 11 |
| CYP98A2 | 13 |

EXAMPLE 4

In vitro Herbicide Assays

To determine whether any of the present soybean P-450 proteins synthesized in yeast displayed significant herbicide metabolic activity, microsomal preparations possessing each of the five soybean P-450s that were effectively expressed in yeast (as judged by their reduced CO difference spectra, see above) were incubated individually with NADPH and radio-isotopes of the compounds listed in Table 3. These substrates represent six different classes of herbicides and one organophosphate insecticide (diazinon). Upon termination of the reaction, each sample was analyzed by thin layer chromatography (TLC) to reveal potential metabolic breakdown products.

Figure 3:
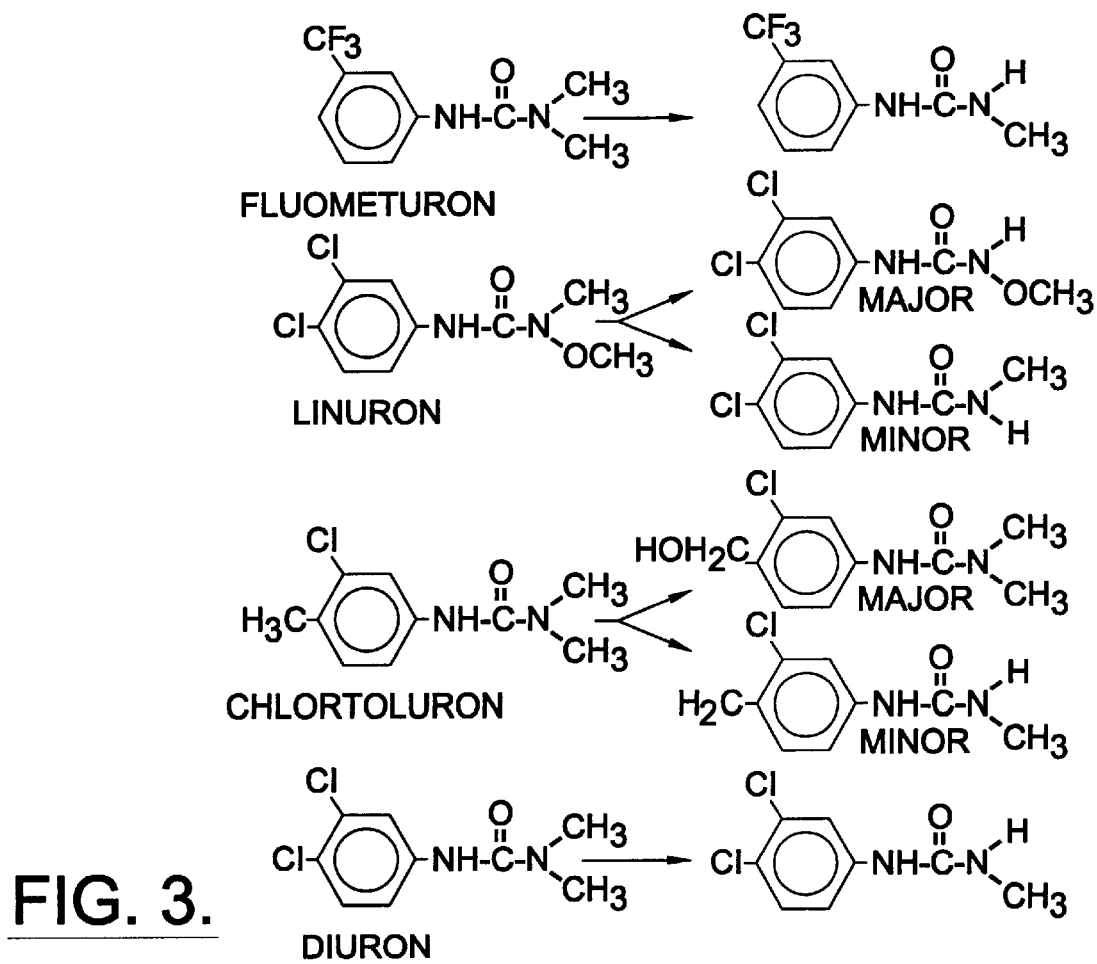
FIG. 3 shows the chemical structures of fluometuron, linuron, chlortoluron and diuron, and their previously characterized metabolites. The linuron and chlortoluron metabolites are designated major or minor depending on their predicted relative abundance in assays using yeast microsomes containing the soybean CYP71A10 protein.
Figure 2:
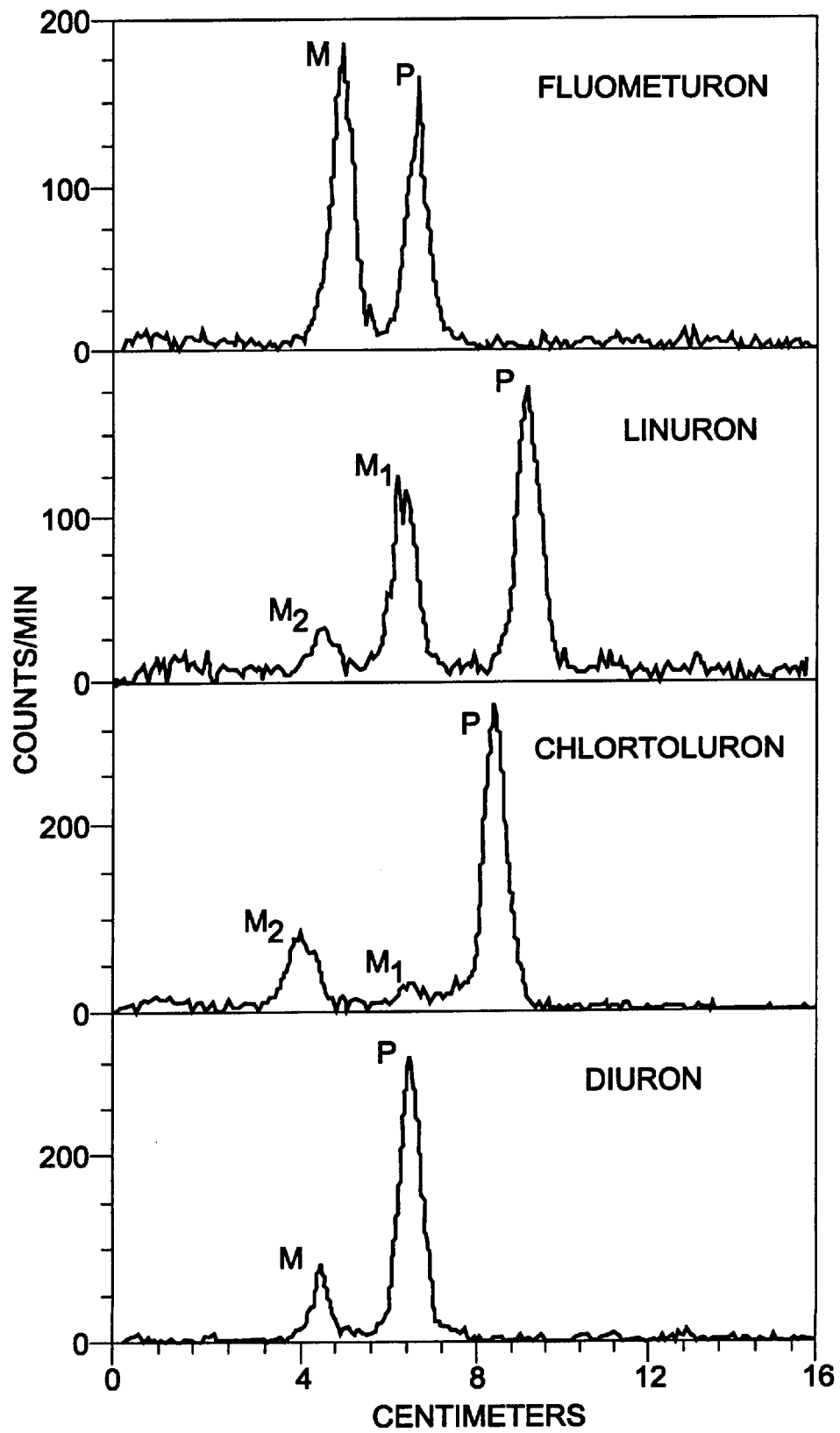
FIG. 2 shows thin-layer chromatograms of [$^{14}$C]-radiolabeled fluometuron, linuron, chlortoluron, and diuron and their respective metabolites after incubation of the radiolabeled herbicides with yeast microsomes containing the CYP71A10 protein. Initial substrate concentrations for fluometuron, linuron, chlortoluron and diuron were 5.2, 6.5, 4.0, and 3.7 µM, respectively. P=parent compound; M=metabolite.

The P-450 proteins expressed from clones CYP71D10, CYP77A3, CYP83D1, and CYP98A2 displayed no apparent in vitro metabolic activity against any of the 11 compounds tested (data not shown). In contrast, the P-450 enzyme produced from construct CYP71A10 demonstrated considerable activity against the phenylurea class of herbicides, but no activity against the remaining compounds. As shown in FIG. 2, fluometuron and diuron were converted to a single metabolite; linuron and chlortoluron were transformed into two (a major and a minor) metabolites. FIG. 3 shows the chemical structures of the four phenylurea herbicides tested in this study, and the derivatives that have previously been characterized as the first metabolites produced during the detoxification of the respective herbicides in plants known to metabolize these compounds (Voss and Geissbtihler, Proc. Brit. Weed Contr. Conf. 8:266–268 (1966); Suzuki and Casida, J. Agric. Food Chem. 29:1027 (1981); Ryan et al., Pestic. Biochem. Physiol. 16:213–221 (1981)).

Figure 4:
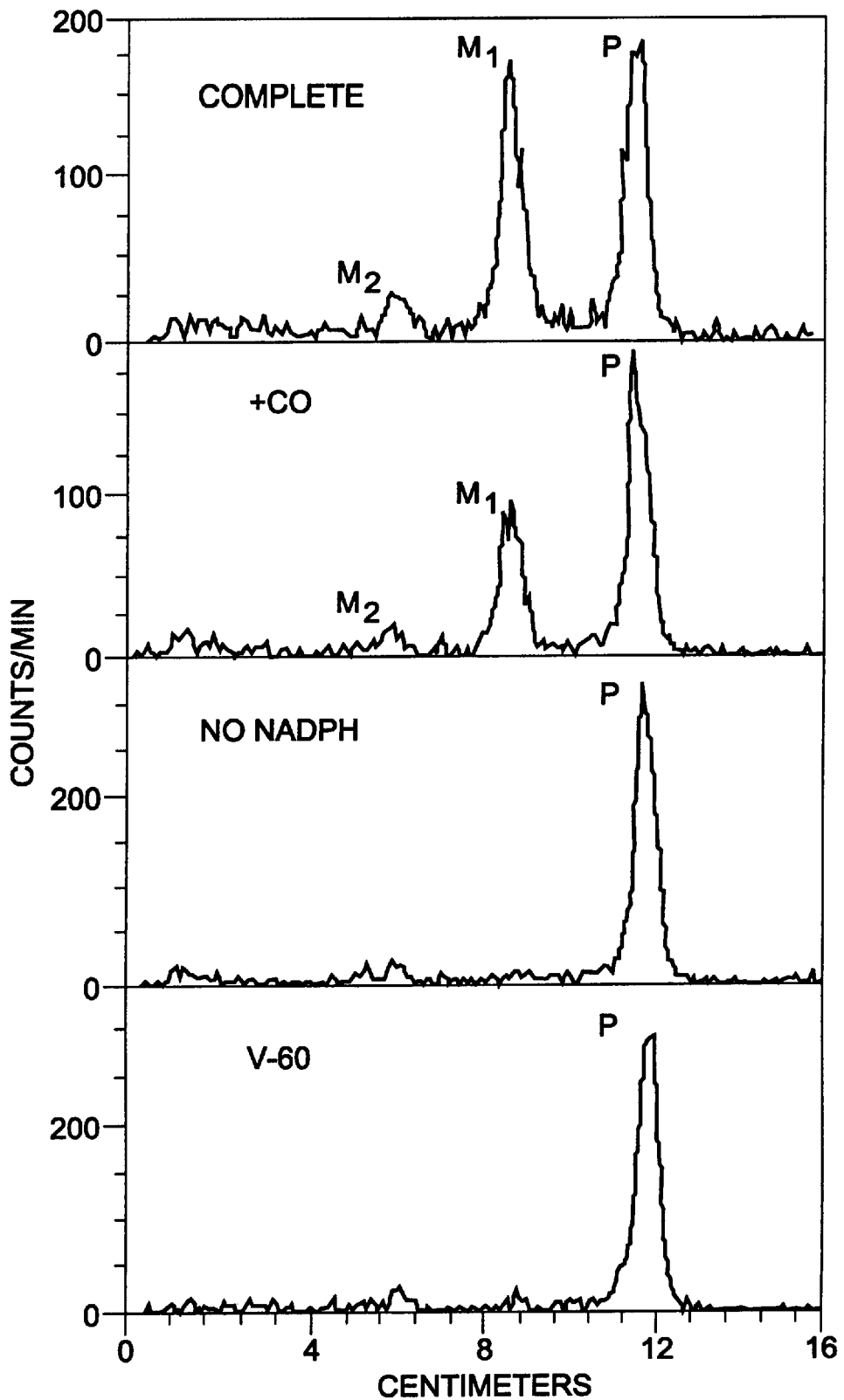
FIG. 4 shows thin-layer chromatograms using [$^{14}$C]-radiolabeled linuron in various control reactions. The complete reaction mixture (COMPLETE) contained 3.2 µM linuron, 0.75 mM NADPH and 2.5 mg/ml microsomal protein isolated from CYP71A10-transformed yeast in 50 mM phosphate buffer (pH 7.1). Other reactions varied from COMPLETE by the addition of carbon monoxide (+CO), the omission of NADPH (NO NADPH), or the use of yeast microsomes isolated from cells expressing the control vector (V-60). P=parent compound; M=metabolite.

To further confirm that the herbicide metabolism measured from microsomes of yeast expressing CYP71A10 was attributable to a P-450 activity, additional assays utilizing linuron as the substrate were conducted. As shown in FIG. 4, linuron metabolizing activity is reduced approximately 37% in the presence of CO, and no metabolites are observed when NADPH is omitted from the reaction. Activity is also completely abolished upon addition of tetcyclasis, a potent P-450 inhibitor (data not shown). Furthermore, no activity is detected when microsomal preparations are used from yeast cells expressing only the V60 control plasmid. These results verify that the observed herbicide metabolizing activity is derived from the soybean CYP71A10 cDNA.

The kinetic properties and catalytic activities of the soybean CYP71A10 protein enzyme differed significantly among the four phenylurea-type herbicide substrates. As shown in Table 4, turnover rates for fluometuron and linuron were considerably greater than those observed for chlortoluron and diuron. The observed reduced activity for the later two substrates is apparently not the result of decreased binding affinities since the apparent $K_m$ s for chlortoluron and diuron are lower than those measured for fluometuron and linuron.

TABLE 3

Compounds Used in Metabolism Assays

| Common Name | Chemical Family |
| --- | --- |
| Alachlor | Acetanilide |
| Metolachlor | Acetanilide |
| Bentazon | Benzothiadiazole |
| Imazaquin | Imidazolinone |
| Chlortoluron | Phenylurea |
| Diuron | Phenylurea |
| Fluometuron | Phenylurea |
| Linuron | Phenylurea |
| Prosulfuron | Sulfonylurea |
| Metribuzin | as-Triazine |
| Diazinon | Organophosphate |

TABLE 4

In Vitro Kinetic Parameters of the CYP71A10 Enzyme for Four Phenylurea Substrates

| Substrate | $K_{m,\ app}$ ($\mu$M) | $V_{max}$ (pmol min$^{-1}$ mg$^{-1}$ protein) | Turnover (min$^{-1}$) |
| --- | --- | --- | --- |
| Fluometuron | 14.9 (1.0)* | 303.6 (10.8) | 6.8 (0.24) |
| Linuron | 9.8 (2.1) | 125.6 (12.0) | 2.8 (0.27) |
| Chlortoluron | 1.0 (0.2) | 29.4 (2.2) | 0.7 (0.05) |
| Diuron | 1.5 (0.3) | 16.8 (1.6) | 0.4 (0.04) |

*Values in parentheses represent standard error.
Assays were repeated three times for linuron and twice for all other substrates.
Concentration ranges ($\mu$M) used were 3.2–27.7 for fluometuron, 3.8–28.3 for linuron, 0.7–4.0 for chlortoluron, and 0.7–3.7 for diuron.

EXAMPLE 5

Analysis of Metabolites

As shown in FIG. 2, CYP71A10-mediated degradation of phenylurea herbicides resulted in the accumulation of either one or two metabolites, depending on the particular substrate used. To determine the structure of the metabolites, the single metabolite observed in the fluometuron assay and both the major and minor metabolites generated in the linuron assay were analyzed by liquid chromatography/mass spectroscopy (LC/MS) analysis (results not shown). Analysis of the fluometuron metabolite by LC/MS in positive ion mode resulted in pseudomolecular ions at m/z 219 [(M+H)$^+$, $C_9H_9F_3N_2O$] and m/z 241 (M+Na)$^+$ that corresponds to a sodium adduct. Daughter ion spectra of m/z 219 produced a prominent m/z 162 fragment ion due to formation of the protonated trifluoromethylaniline $(C_7H_6F_3N+H)^+$. Analysis of the fluometuron metabolite by proton NMR showed a singlet at δ2.71 which integrated for 3 protons (data not shown). The NMR spectra aromatic resonances were similar to aromatic resonances observed in the parent molecule. Spectra of the fluometuron metabolite were consistent for loss of a methyl group from the parent compound.

The major linuron metabolite analyzed by LC/MS in the negative ion mode showed a pseudomolecular ion at m/z 233 (M-H)$^-$ and m/z 235 [(M+2)-H]$^-$ consistent for a molecule containing two chlorine atoms. Daughter ion spectrum at m/z 233 showed a prominent fragment ion at m/z 160 $(C_6H_4Cl_2N-H)^-$. The major linuron metabolite was 15 mass units less than parent compound which is consistent with loss of a methyl group. The position of methyl loss could not be determined based on mass spectral data alone.

The minor linuron metabolite analyzed by LC/MS gave a pseudomolecular ion at m/z 217 (M-H)$^-$ and m/z 219 [(M+2)-H]$^-$ which is consistent for a molecule containing two chlorine atoms. The daughter ion spectrum at m/z 217 showed a prominent fragment ion at m/z 160 which corresponds to formation of the dichloroaniline. The mass spectral data is consistent for the minor linuron metabolite representing N-demethoxy linuron.

These results suggest that the CYP71A10 enzyme expressed in yeast produces the same fluometuron and linuron metabolites as depicted in FIG. 3, which shows the first metabolites produced during the detoxification of the respective herbicides in plants that are known to degrade these compounds. The metabolites of chlortoluron and diuron have not been analyzed directly, but the $R_f$ values of the peaks observed during TLC separation are consistent with these species also representing the compounds shown in FIG. 3 (ring-hydroxymethyl chlortoluron, N-demethyl chlortoluron and N-demethyl diuron). These results indicate that the CYP71A10 enzyme functions primarily as an Ndemethylase with respect to fluometuron, linuron and diuron, with some N-demethoxylase activity also observed with linuron. Using chlortoluron as a substrate, the enzyme apparently functions primarily as a methyl-ring hydroxylase and to a lesser extent as an N-demethylase.

EXAMPLE 6

Herbicide Metabolism in Transgenic Tobacco

To determine whether overexpression of the soybean CYP71A10 cDNA in a higher plant system enhances metabolism of phenylurea herbicides, the GUS gene in the binary vector pBI121 was excised and replaced with the CYP71A10 reading frame. This construct placed the CYP71A10 cDNA under the transcriptional control of the constitutive 35S promoter of Cauliflower Mosaic Virus; kanamycin selection was facilitated via the nptII selectable marker. Agrobacterium-mediated transformation of Nicotiana tabacum cv SR1 leaf discs resulted in the recovery of several dozen independent kanamycin-resistant transformants. The plants were subsequently grown to maturity in a greenhouse and allowed to set seed.

For the herbicide metabolism assays, seeds from one randomly selected transgenic line, designated 25/2, were germinated on kanamycin-containing media to eliminate potential nontransgenic segregants. Of 17 germinated seedlings grown, only one individual was inhibited by kanamycin (data not shown). This result suggests that line 25/2 possesses more than one independently segregating transgene. Individual leaves from the 25/2 progeny were excised and incubated with radiolabeled phenylurea herbicides. As shown in Table 5, leaves of the kanamycin-resistant individuals of line 25/2 metabolized all of the four herbicides tested to a much greater extent than the pBI121-transformed control plants.

The relative migrations of the metabolic products revealed by TLC suggest that the products observed in the in vivo excised leaf assay are primarily the same as were generated from the in vitro assays using yeast microsomes for fluometuron, linuron and diuron (data not shown). For chlortoluron, additional metabolites were also observed. These likely represent combinations of ring-methyl hydroxylated and mono- and di-demethylated species as had been observed by Shiota et al. *Pestic. Biochem. Physiol.* 54:190–198 (1996), in their analysis of chlortoluron-resistant transgenic tobacco that overexpressed the rat CYP1A1 gene. Differences in the ratios of the observed chlortoluron metabolites were also observed between the CYP71A10-transformed and the control plants. Sixty three percent of the metabolites produced in the control leaves was N-demethyl chlortoluron; in contrast, ring-methyl hydroxy chlortoluron was the most abundant metabolite generated in the CYP71A10-transformed leaves (47%) and only 8% of the metabolites represented N-demethyl chlortoluron.

TABLE 5

Phenylurea Metabolism after 14 Hours by Excised Leaves of Transgenic Tobacco Plant 25/2 Progeny

| | % of herbicide metabolized | |
|---|---|---|
| Herbicide[a] | CYP71A10-transformed | Control[b] |
| Fluometuron | 91 (4.5)[c] | 15 (0.6) |
| Linuron | 87 (2.0) | 12 (2.6) |
| Chlortoluron | 85 (8.1)[d] | 39 (7.5)[d] |
| Diuron | 49 (7.0) | 20 (2.0) |

[a]Equal amounts of herbicide (1.2 nmol) were added for each experiment.
[b]Plants transformed with the pBI121 construct were used as controls.
[c]Values in parentheses represent standard error. A single leaf was assayed from four independent 25/2 plants and three independent control plants.
[d]The major chlortoluron metabolite in the control plants represented N-demethyl chlortoluron (63%). The metabolites recovered from the CYP71A10-transformed leaves were ring-methyl hydroxy chlortoluron (47%), N-demethylchlortoluron (8%) and other derivatives (45%).

EXAMPLE 7

Herbicide Tolerance

Figure 5A:
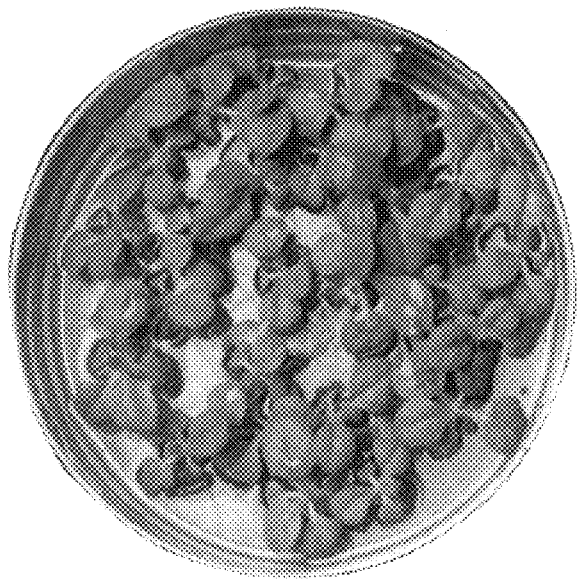
FIG. 5A shows tobacco line 25/2 plants (transformed with soybean CYP71A10) grown on media containing no herbicide.
Figure 5B:
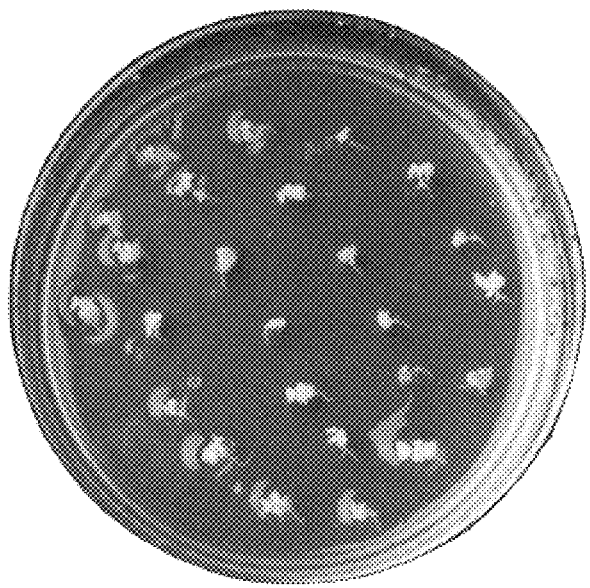
FIG. 5B shows control tobacco plants (transformed with vector pBI121) grown on media containing 0.5 µM linuron.
Figure 5C:
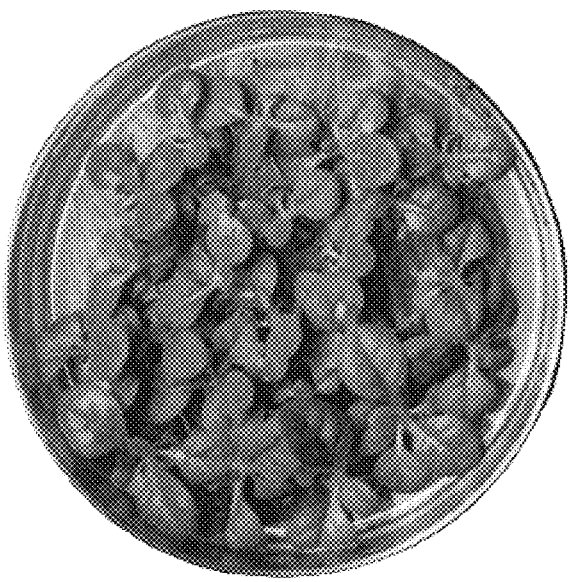
FIG. 5C shows tobacco line 25/2 (transformed with soybean CYP71A10) individuals grown on media containing 0.5 µM linuron.
Figure 5D:
FIG. 5D shows tobacco line 25/2 (transformed with soybean CYP71A10) individuals grown on media containing 2.5 µM linuron.

To establish whether enhanced herbicide metabolism leads to an increase in tolerance at the whole plant level, seeds from transgenic plant 25/2 were germinated on an agarose-base medium containing MS salts and varying concentrations of linuron. Growth of wild-type SR1 plants and transgenic control plants expressing the GUS gene (from vector pBI121) was severely inhibited when exposed to 0.25 $\mu$M linuron and completely arrested at concentrations of 0.5 $\mu$M and higher (data not shown). As shown in FIG. 5, progeny of plant 25/2 grown on media containing no herbicide (FIG. 5A) appeared indistinguishable from the same seed grown in the presence of 0.5 $\mu$M linuron (FIG. 5C), where only one of 23 germinated seedlings appeared to be inhibited by the herbicide. This ratio appears to be consistent with that observed when seeds from the same parent were grown on selective media containing kanamycin; only one of 17 seedlings failed to grow in the presence of kanamycin. FIG. 5B shows control tobacco plants (transformed with vector pBI121), grown on media containing 0.5 $\mu$M linuron. 25/2 plants tolerant to linuron levels as high as 2.5 $\mu$M linuron were observed, although an increasing percentage of the plants showed growth inhibition as the herbicide concentration was increased (FIG. 5D). Segregation of the transgene(s) may be leading to variability in expression levels among the progeny of 25/2.

To examine whether the acquisition of herbicide tolerance is unique to line 25/2, seeds from 20 other independent CYP71A10-expressing transgenic plants were similarly germinated and grown on media containing 0.5 $\mu$M linuron. Of these, 19 lines gave rise to progeny that were linuron tolerant. The percentage of tolerant individuals for each line varied from approximately 20% to 100% (data not shown). This variation likely represents differences in the copy number, expression levels and segregation of the transgene among the independent lines.

Figure 5E:
FIG. 5E shows control tobacco plants (transformed with vector pBI121) grown on media containing 1.0 μM chlortoluron.
Figure 5F:
FIG. 5F shows tobacco line 25/2 (transformed with soybean CYP71A10) individuals grown on media containing 1.0 μM chlortoluron.

Chlortoluron-tolerance of line 25/2 was also evident. At 1.0 $\mu$M herbicide concentration chlortoluron completely arrested the growth of the control plants (FIG. 5E). Although growth of the 25/2 plants was modestly inhibited at this herbicide concentration, with the exception of two presumably nontransgenic segregants, the CYP71A10-transformed plants appeared healthy (FIG. 5F). In contrast to linuron and chlortoluron, little tolerance of line 25/2 to fluometuron or diuron was observed. Herbicide concentrations that were injurious to the control plants also inhibited the growth of line 25/2 individuals. Enhanced fluometuron or diuron tolerance was only observed at the very lowest herbicide concentrations necessary to impose growth inhibition in the control plants (data not shown).

That which is claimed is:

1. An isolated DNA molecule comprising a sequence selected from the group consisting of:
    a) SEQ ID NO:1, SEQ ID NO:3, SEQ ID NO:5, SEQ ID NO:7, SEQ ID NO:9, SEQ ID NO:11, SEQ ID NO:13, SEQ ID NO:15, and SEQ ID NO:17;
    b) DNA sequences which encode an enzyme having a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, and SEQ ID NO:18;
    c) DNA sequences which have at least about 90% sequence identity to the DNA of (a) or (b) above and which encode a cytochrome P450 enzyme; and
    d) DNA sequences which differ from the DNA of (a) or (c) above due to the degeneracy of the genetic code.

2. A peptide encoded by a DNA sequence of claim 1.

3. A cytochrome p450 enzyme having an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, and SEQ ID NO:18.

4. An isolated DNA molecule comprising a sequence selected from the group consisting of:
    a) SEQ ID NO:1;
    b) DNA sequences which encode an enzyme having SEQ ID NO:2;
    c) DNA sequences which have at least about 90% sequence identity to the DNA of (a) or (b) above and which encode a cytchrome P450 enzyme; and
    d) DNA sequences which differ from the DNA of (a) or (c) above due to the degeneracy of the genetic code.

5. A peptide encoded by a DNA sequence of claim 4.

6. A cytochrome p450 peptide having SEQ ID NO:2.

7. A DNA construct comprising an expression cassette, which construct comprising in the 5' to 3' direction, a promoter operable in a plant cell and a DNA segment according to claim 1 positioned downstream from said promoter and operatively associated therewith.

8. A DNA construct according to claim 7, wherein said promoter is constitutively active in plant cells.

9. A DNA construct according to claim 7, wherein said promoter is the 35S promoter from Cauliflower Mosaic virus.

10. A DNA construct according to claim 7, said construct further comprising a plasmid.

11. A DNA construct according to claim 7 carried by a plant transformation vector.

12. A DNA construct according to claim 7 carried by an *Agrobacterium tumefaciens* plant transformation vector.

13. A plant cell containing a DNA construct according to claim 7.

14. A transgenic plant comprising plant cells according to claim 13.

15. A transgenic plant according to claim 14, wherein said plant is a monocot.

16. A transgenic plant according to claim 14, wherein said plant is a dicot.

17. A DNA construct comprising an expression cassette, which construct comprising in the 5' to 3' direction, a promoter operable in a plant cell, and a DNA segment encoding a peptide of SEQ ID NO:2 positioned downstream from said promoter and operatively associated therewith.

18. A DNA construct according to claim 17, wherein said promoter is constitutively active in plant cells.

19. A DNA construct according to claim 17, wherein said promoter is the 35S promoter from Cauliflower Mosaic virus.

20. A DNA construct according to claim 17, said construct further comprising a plasmid.

21. A DNA construct according to claim 17 carried by a plant transformation vector.

22. A DNA construct according to claim 17 carried by an *Agrobacterium tumefaciens* plant transformation vector.

23. A plant cell containing a DNA construct according to claim 17.

24. A transgenic plant comprising plant cells according to claim 23.

25. A transgenic plant according to claim 24, wherein said plant is a monocot.

26. A transgenic plant according to claim 24, wherein said plant is a dicot.

27. A method of making a transgenic plant cell having an increased ability to metabolize phenylurea compounds compared to an untransformed plant cell, said method comprising:

a) providing a plant cell;

b) transforming said plant cell with an exogenous DNA construct comprising, in the 5' to 3' direction, a promoter operable in a plant cell and a DNA sequence encoding a peptide of SEQ ID NO:2, said DNA sequence operably linked to said promoter.

28. A method according to claim 27, wherein said plant cell is from a member of the Solanacae family.

29. A method according to claim 27, wherein said promoter is the 35S promoter from Cauliflower Mosaic virus.

30. A method according to claim 27, wherein said transforming step is carried out by bombarding said plant cell with microparticles carrying said DNA construct.

31. A method according to claim 27 wherein said transforming step is carried out by infecting said plant cell with an *Agrobacterium tumefaciens* containing a Ti plasmid carrying said DNA construct.

32. A method according to claim 27, further comprising regenerating a plant from said transformed plant cell.

33. A transformed plant produced by the method of claim 32.

34. Seed or progeny of a plant according to claim 33, which seed or progeny has inherited said DNA sequence encoding a peptide of SEQ ID NO:2.

35. A transformed plant produced by the method of claim 32, which plant has increased resistance to phenylurea herbicides compared to wild-type plants of the same species.

36. A transgenic plant having an increased ability to metabolize phenylurea compounds compared to an untransformed plant cell, said transgenic plant comprising transgenic plant cells containing an exogenous DNA construct comprising, in the 5' to 3' direction, a promoter operable in said plant cell, said promoter operably linked to a DNA sequence encoding a peptide of SEQ ID NO:2.

37. A transgenic plant according to claim 36, wherein said promoter is the 35S promoter from Cauliflower Mosaic virus.

38. A transgenic plant according to claim 36, wherein said plant is a dicot.

39. A transgenic plant according to claim 36, wherein said plant is a monocot.

40. A transgenic plant according to claim 36, wherein said plant is a member of the family Solanacae.

41. A transgenic plant according to claim 36, which plant is selected from the group consisting of tobacco, potato, tomato, corn, rice, cotton, soybean, rape, wheat, oats, barley, rye and rice.

42. Progeny or seed of a plant according to claim 36, wherein said seed or progeny has inherited said DNA sequence encoding a peptide of SEQ ID NO:2.

43. A transformed plant according to claim 36, which plant has increased resistance to phenylurea herbicides compared to wild-type plants of the same species.

44. A crop comprising a plurality of plants according to claim 36 planted in an agricultural field.

45. A method of using a phenylurea herbicide as a post-emergence herbicide, comprising:

a) planting a crop according to claim 44;

b) applying to said crop a phenylurea herbicide.

46. A method according to claim 45, wherein said crop is selected from the group consisting of turfgrass, tobacco, potato, tomato, corn, rice, cotton, soybean, rape, wheat, oats, barley, rye and rice.

47. A method according to claim 45, wherein said herbicide is selected from the group consisting of fluometuron, linuron, chlortoluron and diuron.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 1838 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: CDS
        (B) LOCATION: 4..1542

(xi) SEQUENCE DESCRIPTION: SEQ ID NO:1:

| | | | | | | | | | | | | | | | | |
|---|---|---|---|---|---|---|---|---|---|---|---|---|---|---|---|---|
| AAA | ATG | GCT | CTA | CTA | TCA | TCA | GTC | CTA | AAG | CAA | TTG | CCG | CAT | GAG | CTA | 48 |
| | Met | Ala | Leu | Leu | Ser | Ser | Val | Leu | Lys | Gln | Leu | Pro | His | Glu | Leu | |
| | 1 | | | | 5 | | | | | 10 | | | | | 15 | |

| AGT | TCA | ACC | CAT | TAC | CTA | ACA | GTT | TTC | TTC | TGC | ATC | TTC | CTT | ATA | CTT | 96 |
|---|---|---|---|---|---|---|---|---|---|---|---|---|---|---|---|---|
| Ser | Ser | Thr | His | Tyr | Leu | Thr | Val | Phe | Phe | Cys | Ile | Phe | Leu | Ile | Leu | |
| | | | | 20 | | | | | 25 | | | | | 30 | | |

| CTT | CAG | CTA | ATA | AGA | AGA | AAC | AAA | TAC | AAT | CTG | CCA | CCA | TCC | CCA | CCA | 144 |
|---|---|---|---|---|---|---|---|---|---|---|---|---|---|---|---|---|
| Leu | Gln | Leu | Ile | Arg | Arg | Asn | Lys | Tyr | Asn | Leu | Pro | Pro | Ser | Pro | Pro | |
| | | | 35 | | | | | 40 | | | | | 45 | | | |

| AAG | ATA | CCC | ATA | ATC | GGC | AAT | CTT | CAC | CAG | CTA | GGC | ACA | CTG | CCA | CAC | 192 |
|---|---|---|---|---|---|---|---|---|---|---|---|---|---|---|---|---|
| Lys | Ile | Pro | Ile | Ile | Gly | Asn | Leu | His | Gln | Leu | Gly | Thr | Leu | Pro | His | |
| | | 50 | | | | | 55 | | | | | 60 | | | | |

| CGC | TCC | TTT | CAT | GCA | CTC | TCA | CAC | AAA | TAT | GGC | CCT | CTC | ATG | ATG | TTG | 240 |
|---|---|---|---|---|---|---|---|---|---|---|---|---|---|---|---|---|
| Arg | Ser | Phe | His | Ala | Leu | Ser | His | Lys | Tyr | Gly | Pro | Leu | Met | Met | Leu | |
| | 65 | | | | | 70 | | | | | 75 | | | | | |

| CAA | TTG | GGT | CAA | ATT | CCA | ACC | CTA | GTG | GTC | TCA | TCA | GCT | GAC | GTG | GCC | 288 |
|---|---|---|---|---|---|---|---|---|---|---|---|---|---|---|---|---|
| Gln | Leu | Gly | Gln | Ile | Pro | Thr | Leu | Val | Val | Ser | Ser | Ala | Asp | Val | Ala | |
| 80 | | | | | 85 | | | | | 90 | | | | | 95 | |

| AGA | GAA | ATA | ATC | AAA | ACG | CAT | GAT | GTT | GTT | TTC | TCC | AAC | CGC | CGA | CAA | 336 |
|---|---|---|---|---|---|---|---|---|---|---|---|---|---|---|---|---|
| Arg | Glu | Ile | Ile | Lys | Thr | His | Asp | Val | Val | Phe | Ser | Asn | Arg | Arg | Gln | |
| | | | | 100 | | | | | 105 | | | | | 110 | | |

| CCT | ACA | GCT | GCT | AAA | ATC | TTT | GGT | TAT | GGA | TGC | AAA | GAT | GTG | GCT | TTC | 384 |
|---|---|---|---|---|---|---|---|---|---|---|---|---|---|---|---|---|
| Pro | Thr | Ala | Ala | Lys | Ile | Phe | Gly | Tyr | Gly | Cys | Lys | Asp | Val | Ala | Phe | |
| | | | 115 | | | | | 120 | | | | | 125 | | | |

| GTG | TAC | TAC | CGC | GAA | GAG | TGG | AGA | CAA | AAG | ATA | AAG | ACA | TGT | AAG | GTT | 432 |
|---|---|---|---|---|---|---|---|---|---|---|---|---|---|---|---|---|
| Val | Tyr | Tyr | Arg | Glu | Glu | Trp | Arg | Gln | Lys | Ile | Lys | Thr | Cys | Lys | Val | |
| | | 130 | | | | | 135 | | | | | 140 | | | | |

| GAG | CTT | ATG | AGT | CTG | AAG | AAG | GTG | CGG | TTG | TTT | CAT | TCC | ATT | AGA | CAA | 480 |
|---|---|---|---|---|---|---|---|---|---|---|---|---|---|---|---|---|
| Glu | Leu | Met | Ser | Leu | Lys | Lys | Val | Arg | Leu | Phe | His | Ser | Ile | Arg | Gln | |
| | 145 | | | | | 150 | | | | | 155 | | | | | |

| GAA | GTT | GTT | ACA | GAG | TTG | GTT | GAA | GCT | ATA | GGT | GAA | GCG | TGT | GGT | AGT | 528 |
|---|---|---|---|---|---|---|---|---|---|---|---|---|---|---|---|---|
| Glu | Val | Val | Thr | Glu | Leu | Val | Glu | Ala | Ile | Gly | Glu | Ala | Cys | Gly | Ser | |
| 160 | | | | | 165 | | | | | 170 | | | | | 175 | |

| GAA | AGA | CCA | TGT | GTG | AAT | CTG | ACT | GAG | ATG | CTG | ATG | GCA | GCA | TCG | AAC | 576 |
|---|---|---|---|---|---|---|---|---|---|---|---|---|---|---|---|---|
| Glu | Arg | Pro | Cys | Val | Asn | Leu | Thr | Glu | Met | Leu | Met | Ala | Ala | Ser | Asn | |
| | | | | 180 | | | | | 185 | | | | | 190 | | |

| GAC | ATT | GTG | TCT | AGA | TGT | GTT | CTT | GGA | CGG | AAG | TGT | GAT | GAT | GCA | TGT | 624 |
|---|---|---|---|---|---|---|---|---|---|---|---|---|---|---|---|---|
| Asp | Ile | Val | Ser | Arg | Cys | Val | Leu | Gly | Arg | Lys | Cys | Asp | Asp | Ala | Cys | |
| | | | 195 | | | | | 200 | | | | | 205 | | | |

| GGT | GGT | AGT | GGC | AGT | AGC | AGC | TTT | GCA | GCG | TTG | GGA | AGA | AAG | ATT | ATG | 672 |
|---|---|---|---|---|---|---|---|---|---|---|---|---|---|---|---|---|
| Gly | Gly | Ser | Gly | Ser | Ser | Ser | Phe | Ala | Ala | Leu | Gly | Arg | Lys | Ile | Met | |
| | | 210 | | | | | 215 | | | | | 220 | | | | |

| AGA | CTA | TTA | TCG | GCT | TTC | AGC | GTG | GGT | GAT | TTC | TTC | CCT | TCG | TTG | GGT | 720 |
|---|---|---|---|---|---|---|---|---|---|---|---|---|---|---|---|---|
| Arg | Leu | Leu | Ser | Ala | Phe | Ser | Val | Gly | Asp | Phe | Phe | Pro | Ser | Leu | Gly | |
| | 225 | | | | | 230 | | | | | 235 | | | | | |

| TGG | GTT | GAC | TAT | CTG | ACT | GGC | TTA | ATT | CCA | GAG | ATG | AAA | ACC | ACG | TTT | 768 |
|---|---|---|---|---|---|---|---|---|---|---|---|---|---|---|---|---|
| Trp | Val | Asp | Tyr | Leu | Thr | Gly | Leu | Ile | Pro | Glu | Met | Lys | Thr | Thr | Phe | |
| 240 | | | | | 245 | | | | | 250 | | | | | 255 | |

| CTC | GCA | GTA | GAT | GCT | TTC | CTT | GAT | GAG | GTA | ATT | GCA | GAA | CAC | GAG | AGC | 816 |
|---|---|---|---|---|---|---|---|---|---|---|---|---|---|---|---|---|
| Leu | Ala | Val | Asp | Ala | Phe | Leu | Asp | Glu | Val | Ile | Ala | Glu | His | Glu | Ser | |
| | | | | 260 | | | | | 265 | | | | | 270 | | |

| AGT | AAC | AAG | AAG | AAT | GAT | GAC | TTC | TTG | GGG | ATA | CTT | CTT | CAA | CTT | CAA | 864 |
|---|---|---|---|---|---|---|---|---|---|---|---|---|---|---|---|---|
| Ser | Asn | Lys | Lys | Asn | Asp | Asp | Phe | Leu | Gly | Ile | Leu | Leu | Gln | Leu | Gln | |
| | | | 275 | | | | | 280 | | | | | 285 | | | |

```
GAA TGT GGG AGG CTT GAC TTT CAG CTC GAC CGA GAT AAC CTC AAA GCA        912
Glu Cys Gly Arg Leu Asp Phe Gln Leu Asp Arg Asp Asn Leu Lys Ala
            290                 295                 300

ATC CTA GTG GAC ATG ATA ATA GGT GGG AGT GAC ACT ACT TCA ACA ACT        960
Ile Leu Val Asp Met Ile Ile Gly Gly Ser Asp Thr Thr Ser Thr Thr
305                 310                 315

CTA GAA TGG ACT TTT GCG GAG TTC CTT AGA AAT CCA AAT ACC ATG AAG       1008
Leu Glu Trp Thr Phe Ala Glu Phe Leu Arg Asn Pro Asn Thr Met Lys
320                 325                 330                 335

AAA GCT CAA GAA GAG GTA AGA AGA GTG GTG GGA ATC AAT TCC AAA GCA       1056
Lys Ala Gln Glu Glu Val Arg Arg Val Val Gly Ile Asn Ser Lys Ala
                340                 345                 350

GTA CTG GAT GAA AAT TGT GTG AAT CAA ATG AAC TAC TTG AAA TGT GTA       1104
Val Leu Asp Glu Asn Cys Val Asn Gln Met Asn Tyr Leu Lys Cys Val
            355                 360                 365

GTC AAA GAA ACT TTG AGA TTA CAT CCA CCC CTT CCT CTT TTG ATT GCT       1152
Val Lys Glu Thr Leu Arg Leu His Pro Pro Leu Pro Leu Leu Ile Ala
        370                 375                 380

CGA GAG ACA TCA TCA AGT GTA AAA CTA AGA GGG TAC GAT ATT CCC GCA       1200
Arg Glu Thr Ser Ser Ser Val Lys Leu Arg Gly Tyr Asp Ile Pro Ala
385                 390                 395

AAA ACA ATG GTA TTT ATC AAT GCA TGG GCG ATC CAG AGG GAT CCT GAA       1248
Lys Thr Met Val Phe Ile Asn Ala Trp Ala Ile Gln Arg Asp Pro Glu
400                 405                 410                 415

TTA TGG GAT GAT CCT GAA GAA TTT ATT CCC GAA AGA TTT GAA ACT AGC       1296
Leu Trp Asp Asp Pro Glu Glu Phe Ile Pro Glu Arg Phe Glu Thr Ser
                420                 425                 430

CAA GTT GAT CTT AAT GGA CAA GAT TTT CAA TTA ATT CCG TTC GGT ATT       1344
Gln Val Asp Leu Asn Gly Gln Asp Phe Gln Leu Ile Pro Phe Gly Ile
            435                 440                 445

GGG AGA AGG GGA TGC CCT GCA ATG TCA TTT GGA CTT GCT TCA ACT GAG       1392
Gly Arg Arg Gly Cys Pro Ala Met Ser Phe Gly Leu Ala Ser Thr Glu
        450                 455                 460

TAT GTT CTT GCT AAT CTT TTG TAT TGG TTC AAT TGG AAT ATG TCC GAG       1440
Tyr Val Leu Ala Asn Leu Leu Tyr Trp Phe Asn Trp Asn Met Ser Glu
465                 470                 475

TCT GGA CGT ATA TTG ATG CAC AAC ATT GAC ATG AGT GAG ACA AAT GGA       1488
Ser Gly Arg Ile Leu Met His Asn Ile Asp Met Ser Glu Thr Asn Gly
480                 485                 490                 495

CTC ACT GTC AGT AAG AAA GTA CCA CTT CAT CTT GAA CCA GAA CCA TAT       1536
Leu Thr Val Ser Lys Lys Val Pro Leu His Leu Glu Pro Glu Pro Tyr
                500                 505                 510

AAA ACA TGATCATTTC ACATTATGCA TGTTTGGCAA CACCTATAAA GAGTATAGAT       1592
Lys Thr

CTGGAAGTAC TTCAATTTAG TAATGGATGT AAAAGCTATA CAATAAGAAG TGCTAACAAG   1652

CTAGGATATG AGCATTTATG GAGTAACGAG TGAGGTTCCA AAGAGTCTAA TTACTCGTCT   1712

CTTGAACATT GTTATATTTG TTTTCTTGCA GTTTGTTAAT CTTTTGAATA GTTGTTTCAC   1772

ATTTATTTTT GTATGGTTTG TTGGTATGTT GTGGAAGGCG TTAGTAAAAA TTTGTGGTGT   1832

GTTCTT                                                              1838

(2) INFORMATION FOR SEQ ID NO:2:

(i) SEQUENCE CHARACTERISTICS:
        (A) LENGTH: 513 amino acids
        (B) TYPE: amino acid
        (D) TOPOLOGY: linear
```

(ii) MOLECULE TYPE: protein (xi) SEQUENCE DESCRIPTION: SEQ ID NO:2:

```
Met Ala Leu Leu Ser Ser Val Leu Lys Gln Leu Pro His Glu Leu Ser
 1               5                  10                  15

Ser Thr His Tyr Leu Thr Val Phe Phe Cys Ile Phe Leu Ile Leu Leu
            20                  25                  30

Gln Leu Ile Arg Arg Asn Lys Tyr Asn Leu Pro Pro Ser Pro Pro Lys
        35                  40                  45

Ile Pro Ile Ile Gly Asn Leu His Gln Leu Gly Thr Leu Pro His Arg
 50                  55                  60

Ser Phe His Ala Leu Ser His Lys Tyr Gly Pro Leu Met Met Leu Gln
 65                  70                  75                  80

Leu Gly Gln Ile Pro Thr Leu Val Val Ser Ser Ala Asp Val Ala Arg
                85                  90                  95

Glu Ile Ile Lys Thr His Asp Val Val Phe Ser Asn Arg Arg Gln Pro
                100                 105                 110

Thr Ala Ala Lys Ile Phe Gly Tyr Gly Cys Lys Asp Val Ala Phe Val
            115                 120                 125

Tyr Tyr Arg Glu Glu Trp Arg Gln Lys Ile Lys Thr Cys Lys Val Glu
130                 135                 140

Leu Met Ser Leu Lys Lys Val Arg Leu Phe His Ser Ile Arg Gln Glu
145                 150                 155                 160

Val Val Thr Glu Leu Val Glu Ala Ile Gly Glu Ala Cys Gly Ser Glu
                165                 170                 175

Arg Pro Cys Val Asn Leu Thr Glu Met Leu Met Ala Ala Ser Asn Asp
            180                 185                 190

Ile Val Ser Arg Cys Val Leu Gly Arg Lys Cys Asp Asp Ala Cys Gly
            195                 200                 205

Gly Ser Gly Ser Ser Ser Phe Ala Ala Leu Gly Arg Lys Ile Met Arg
        210                 215                 220

Leu Leu Ser Ala Phe Ser Val Gly Asp Phe Phe Pro Ser Leu Gly Trp
225                 230                 235                 240

Val Asp Tyr Leu Thr Gly Leu Ile Pro Glu Met Lys Thr Thr Phe Leu
                245                 250                 255

Ala Val Asp Ala Phe Leu Asp Glu Val Ile Ala Glu His Glu Ser Ser
            260                 265                 270

Asn Lys Lys Asn Asp Asp Phe Leu Gly Ile Leu Leu Gln Leu Gln Glu
        275                 280                 285

Cys Gly Arg Leu Asp Phe Gln Leu Asp Arg Asp Asn Leu Lys Ala Ile
290                 295                 300

Leu Val Asp Met Ile Ile Gly Gly Ser Asp Thr Thr Ser Thr Thr Leu
305                 310                 315                 320

Glu Trp Thr Phe Ala Glu Phe Leu Arg Asn Pro Asn Thr Met Lys Lys
                325                 330                 335

Ala Gln Glu Glu Val Arg Arg Val Val Gly Ile Asn Ser Lys Ala Val
            340                 345                 350

Leu Asp Glu Asn Cys Val Asn Gln Met Asn Tyr Leu Lys Cys Val Val
            355                 360                 365

Lys Glu Thr Leu Arg Leu His Pro Pro Leu Pro Leu Leu Ile Ala Arg
        370                 375                 380

Glu Thr Ser Ser Ser Val Lys Leu Arg Gly Tyr Asp Ile Pro Ala Lys
385                 390                 395                 400
```

```
Thr Met Val Phe Ile Asn Ala Trp Ala Ile Gln Arg Asp Pro Glu Leu
            405                 410                 415

Trp Asp Pro Glu Glu Phe Ile Pro Glu Arg Phe Glu Thr Ser Gln
        420                 425                 430

Val Asp Leu Asn Gly Gln Asp Phe Gln Leu Ile Pro Phe Gly Ile Gly
            435                 440                 445

Arg Arg Gly Cys Pro Ala Met Ser Phe Gly Leu Ala Ser Thr Glu Tyr
    450                 455                 460

Val Leu Ala Asn Leu Leu Tyr Trp Phe Asn Trp Asn Met Ser Glu Ser
465                 470                 475                 480

Gly Arg Ile Leu Met His Asn Ile Asp Met Ser Glu Thr Asn Gly Leu
                485                 490                 495

Thr Val Ser Lys Lys Val Pro Leu His Leu Glu Pro Glu Pro Tyr Lys
            500                 505                 510

Thr (2) INFORMATION FOR SEQ ID NO:3:

(i) SEQUENCE CHARACTERISTICS:
        (A) LENGTH: 1691 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 16..1545

(xi) SEQUENCE DESCRIPTION: SEQ ID NO:3:

CCTAGATCTA TCATC ATG GTC ATG GAG CTT CAC AAC CAC ACC CCT TTC TCT       51
                Met Val Met Glu Leu His Asn His Thr Pro Phe Ser
                  1               5                  10

ATT TAC TTC ATT ACC TCC ATT CTC TTT ATT TTC TTC GTG TTC TTC AAA       99
Ile Tyr Phe Ile Thr Ser Ile Leu Phe Ile Phe Phe Val Phe Phe Lys
             15                  20                  25

TTA GTT CAA AGA TCG GAT TCC AAA ACC TCC TCT ACC TGC AAA TTG CCC       147
Leu Val Gln Arg Ser Asp Ser Lys Thr Ser Ser Thr Cys Lys Leu Pro
         30                  35                  40

CCA GGA CCA AGG ACA CTA CCT CTC ATA GGG AAC ATA CAC CAG ATT GTT       195
Pro Gly Pro Arg Thr Leu Pro Leu Ile Gly Asn Ile His Gln Ile Val
 45                  50                  55                  60

GGC TCA CTG CCG GTT CAT TAC TAC TTA AAA AAT TTG GCA GAT AAG TAT       243
Gly Ser Leu Pro Val His Tyr Tyr Leu Lys Asn Leu Ala Asp Lys Tyr
                 65                  70                  75

GGT CCA TTA ATG CAT CTA AAA CTA GGA GAG GTG TCC AAC ATC ATA GTC       291
Gly Pro Leu Met His Leu Lys Leu Gly Glu Val Ser Asn Ile Ile Val
             80                  85                  90

ACT TCC CCA GAA ATG GCC CAA GAG ATT ATG AAG ACA CAT GAT CTC AAC       339
Thr Ser Pro Glu Met Ala Gln Glu Ile Met Lys Thr His Asp Leu Asn
         95                 100                 105

TTC TCT GAT AGG CCA GAC TTT GTA TTG TCT AGA ATA GTT TCT TAC AAC       387
Phe Ser Asp Arg Pro Asp Phe Val Leu Ser Arg Ile Val Ser Tyr Asn
     110                 115                 120

GGT TCT GGC ATT GTC TTC AGT CAA CAT GGA GAC TAT TGG AGG CAA CTA       435
Gly Ser Gly Ile Val Phe Ser Gln His Gly Asp Tyr Trp Arg Gln Leu
125                 130                 135                 140

AGA AAG ATA TGC ACA GTA GAG TTA CTA ACA GCA AAG CGC GTG CAG TCT       483
Arg Lys Ile Cys Thr Val Glu Leu Leu Thr Ala Lys Arg Val Gln Ser
                145                 150                 155
```

-continued

| | |
|---|---|
| TTT CGG TCC ATA AGA GAA GAG GAG GTG GCA GAA CTA GTT AAA AAA ATA<br>Phe Arg Ser Ile Arg Glu Glu Glu Val Ala Glu Leu Val Lys Lys Ile<br>           160                        165                170 | 531 |
| GCT GCA ACT GCA AGT GAA GAA GGG GGG TCC ATT TTT AAT CTC ACC CAG<br>Ala Ala Thr Ala Ser Glu Glu Gly Gly Ser Ile Phe Asn Leu Thr Gln<br>           175                        180                185 | 579 |
| AGC ATT TAC TCA ATG ACT TTT GGG ATA GCG GCA CGA GCG GCT TTT GGT<br>Ser Ile Tyr Ser Met Thr Phe Gly Ile Ala Ala Arg Ala Ala Phe Gly<br>           190                        195                200 | 627 |
| AAA AAG AGC AGA TAC CAA CAA GTG TTC ATA TCA AAC ATG CAT AAA CAA<br>Lys Lys Ser Arg Tyr Gln Gln Val Phe Ile Ser Asn Met His Lys Gln<br>205                        210                        215                220 | 675 |
| TTG ATG CTT CTG GGA GGG TTT TCT GTT GCT GAT CTC TAT CCT TCT AGT<br>Leu Met Leu Leu Gly Gly Phe Ser Val Ala Asp Leu Tyr Pro Ser Ser<br>                        225                        230                235 | 723 |
| AGA GTG TTT CAA ATG ATG GGG GCG ACG GGG AAA CTT GAA AAA GTG CAT<br>Arg Val Phe Gln Met Met Gly Ala Thr Gly Lys Leu Glu Lys Val His<br>           240                        245                250 | 771 |
| AGA GTG ACA GAT AGG GTG TTG CAA GAC ATC ATC GAC GAG CAC AAA AAT<br>Arg Val Thr Asp Arg Val Leu Gln Asp Ile Ile Asp Glu His Lys Asn<br>           255                        260                265 | 819 |
| AGA AAC AGA AGC AGC GAG GAG CGT GAA GCA GTG GAA GAT CTA GTT GAT<br>Arg Asn Arg Ser Ser Glu Glu Arg Glu Ala Val Glu Asp Leu Val Asp<br>           270                        275                280 | 867 |
| GTT CTT CTC AAG TTT CAA AAG GAA TCG GAA TTT CGC TTG ACT GAT GAC<br>Val Leu Leu Lys Phe Gln Lys Glu Ser Glu Phe Arg Leu Thr Asp Asp<br>285                        290                        295                300 | 915 |
| AAC ATT AAA GCC GTC ATC CAG GAC ATA TTC ATT GGT GGA GGC GAA ACA<br>Asn Ile Lys Ala Val Ile Gln Asp Ile Phe Ile Gly Gly Gly Glu Thr<br>                        305                        310                315 | 963 |
| TCA TCT TCT GTT GTG GAA TGG GGG ATG TCA GAA TTG ATA AGA AAC CCG<br>Ser Ser Ser Val Val Glu Trp Gly Met Ser Glu Leu Ile Arg Asn Pro<br>                    320                        325                330 | 1011 |
| AGG GTG ATG GAA GAA GCA CAA GCA GAG GTG AGA AGA GTG TAT GAT AGC<br>Arg Val Met Glu Glu Ala Gln Ala Glu Val Arg Arg Val Tyr Asp Ser<br>           335                        340                345 | 1059 |
| AAG GGA TAT GTG GAT GAG ACA GAA TTG CAC CAA TTG ATA TAC TTA AAG<br>Lys Gly Tyr Val Asp Glu Thr Glu Leu His Gln Leu Ile Tyr Leu Lys<br>           350                        355                360 | 1107 |
| TCC ATC ATC AAA GAA ACC ATG AGG TTA CAT CCA CCT GTG CCA TTG TTA<br>Ser Ile Ile Lys Glu Thr Met Arg Leu His Pro Pro Val Pro Leu Leu<br>365                        370                        375                380 | 1155 |
| GTT CCT AGA GTA AGT AGA GAA AGG TGC CAA ATC AAT GGA TAT GAG ATA<br>Val Pro Arg Val Ser Arg Glu Arg Cys Gln Ile Asn Gly Tyr Glu Ile<br>                        385                        390                395 | 1203 |
| CCC TCT AAG ACT AGG ATC ATT ATC AAT GCT TGG GCA ATT GGA AGG AAT<br>Pro Ser Lys Thr Arg Ile Ile Ile Asn Ala Trp Ala Ile Gly Arg Asn<br>                    400                        405                410 | 1251 |
| CCT AAG TAT TGG GGT GAA ACT GAG AGT TTT AAA CCT GAG AGG TTT CTT<br>Pro Lys Tyr Trp Gly Glu Thr Glu Ser Phe Lys Pro Glu Arg Phe Leu<br>                    415                        420                425 | 1299 |
| AAT AGC TCC ATT GAT TTT AGG GGC ACA GAC TTT GAA TTT ATC CCA TTT<br>Asn Ser Ser Ile Asp Phe Arg Gly Thr Asp Phe Glu Phe Ile Pro Phe<br>           430                        435                440 | 1347 |
| GGT GCT GGA AGG AGG ATC TGC CCC GGC ATT ACA TTT GCC ATA CCC AAC<br>Gly Ala Gly Arg Arg Ile Cys Pro Gly Ile Thr Phe Ala Ile Pro Asn<br>445                        450                        455                460 | 1395 |

-continued

```
ATT GAG TTG CCA CTT GCT CAG TTA CTT TAC CAC TTT GAT TGG AAG CTT       1443
Ile Glu Leu Pro Leu Ala Gln Leu Leu Tyr His Phe Asp Trp Lys Leu
                465                 470                 475

CCC AAT AAA ATG AAG AAT GAA GAA CTT GAC ATG ACG GAG TCA AAT GGA       1491
Pro Asn Lys Met Lys Asn Glu Glu Leu Asp Met Thr Glu Ser Asn Gly
            480                 485                 490

ATT ACT TTA CGA AGA CAA AAT GAC CTC TGC TTG ATT CCC ATT ACT CGT       1539
Ile Thr Leu Arg Arg Gln Asn Asp Leu Cys Leu Ile Pro Ile Thr Arg
        495                 500                 505

CTA CCT TAAAATGTAT GAACAATTAA TGTCATAAAC TATTTAAGTT TTATCTTTTA        1595
Leu Pro
    510

CTACTTCCAG CATTTCGTAA TTGGACAATG ACTATGATTA ACTTAAGTTA CTTCCTTATG     1655

ATTAACTTGA CATATGAATG AACATTTCTA AGATAA                               1691
```

(2) INFORMATION FOR SEQ ID NO:4:

(i) SEQUENCE CHARACTERISTICS:
        (A) LENGTH: 510 amino acids
        (B) TYPE: amino acid
        (D) TOPOLOGY: linear (ii) MOLECULE TYPE: protein (xi) SEQUENCE DESCRIPTION: SEQ ID NO:4:

```
Met Val Met Glu Leu His Asn His Thr Pro Phe Ser Ile Tyr Phe Ile
 1               5                  10                  15

Thr Ser Ile Leu Phe Ile Phe Phe Val Phe Phe Lys Leu Val Gln Arg
                20                  25                  30

Ser Asp Ser Lys Thr Ser Ser Thr Cys Lys Leu Pro Pro Gly Pro Arg
            35                  40                  45

Thr Leu Pro Leu Ile Gly Asn Ile His Gln Ile Val Gly Ser Leu Pro
        50                  55                  60

Val His Tyr Tyr Leu Lys Asn Leu Ala Asp Lys Tyr Gly Pro Leu Met
65                  70                  75                  80

His Leu Lys Leu Gly Glu Val Ser Asn Ile Ile Val Thr Ser Pro Glu
                85                  90                  95

Met Ala Gln Glu Ile Met Lys Thr His Asp Leu Asn Phe Ser Asp Arg
            100                 105                 110

Pro Asp Phe Val Leu Ser Arg Ile Val Ser Tyr Asn Gly Ser Gly Ile
        115                 120                 125

Val Phe Ser Gln His Gly Asp Tyr Trp Arg Gln Leu Arg Lys Ile Cys
    130                 135                 140

Thr Val Glu Leu Leu Thr Ala Lys Arg Val Gln Ser Phe Arg Ser Ile
145                 150                 155                 160

Arg Glu Glu Glu Val Ala Glu Leu Val Lys Lys Ile Ala Ala Thr Ala
                165                 170                 175

Ser Glu Glu Gly Gly Ser Ile Phe Asn Leu Thr Gln Ser Ile Tyr Ser
            180                 185                 190

Met Thr Phe Gly Ile Ala Ala Arg Ala Ala Phe Gly Lys Lys Ser Arg
        195                 200                 205

Tyr Gln Gln Val Phe Ile Ser Asn Met His Lys Gln Leu Met Leu Leu
    210                 215                 220

Gly Gly Phe Ser Val Ala Asp Leu Tyr Pro Ser Ser Arg Val Phe Gln
225                 230                 235                 240

Met Met Gly Ala Thr Gly Lys Leu Glu Lys Val His Arg Val Thr Asp
                245                 250                 255
```

```
Arg Val Leu Gln Asp Ile Ile Asp Glu His Lys Asn Arg Asn Arg Ser
                260                 265                 270

Ser Glu Glu Arg Glu Ala Val Glu Asp Leu Val Asp Val Leu Leu Lys
            275                 280                 285

Phe Gln Lys Glu Ser Glu Phe Arg Leu Thr Asp Asp Asn Ile Lys Ala
        290                 295                 300

Val Ile Gln Asp Ile Phe Ile Gly Gly Glu Thr Ser Ser Ser Val
305                 310                 315                 320

Val Glu Trp Gly Met Ser Glu Leu Ile Arg Asn Pro Arg Val Met Glu
                325                 330                 335

Glu Ala Gln Ala Glu Val Arg Arg Val Tyr Asp Ser Lys Gly Tyr Val
            340                 345                 350

Asp Glu Thr Glu Leu His Gln Leu Ile Tyr Leu Lys Ser Ile Ile Lys
        355                 360                 365

Glu Thr Met Arg Leu His Pro Pro Val Pro Leu Leu Val Pro Arg Val
    370                 375                 380

Ser Arg Glu Arg Cys Gln Ile Asn Gly Tyr Glu Ile Pro Ser Lys Thr
385                 390                 395                 400

Arg Ile Ile Ile Asn Ala Trp Ala Ile Gly Arg Asn Pro Lys Tyr Trp
                405                 410                 415

Gly Glu Thr Glu Ser Phe Lys Pro Glu Arg Phe Leu Asn Ser Ser Ile
            420                 425                 430

Asp Phe Arg Gly Thr Asp Phe Glu Phe Ile Pro Phe Gly Ala Gly Arg
        435                 440                 445

Arg Ile Cys Pro Gly Ile Thr Phe Ala Ile Pro Asn Ile Glu Leu Pro
    450                 455                 460

Leu Ala Gln Leu Leu Tyr His Phe Asp Trp Lys Leu Pro Asn Lys Met
465                 470                 475                 480

Lys Asn Glu Glu Leu Asp Met Thr Glu Ser Asn Gly Ile Thr Leu Arg
                485                 490                 495

Arg Gln Asn Asp Leu Cys Leu Ile Pro Ile Thr Arg Leu Pro
            500                 505                 510

(2) INFORMATION FOR SEQ ID NO:5:

(i) SEQUENCE CHARACTERISTICS:
        (A) LENGTH: 1644 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 4..1542

(xi) SEQUENCE DESCRIPTION: SEQ ID NO:5:

AAA ATG GCC ACT CTT TCC TCC TAC GAC CAC TTC ATC TTC ACT GCC TTA        48
    Met Ala Thr Leu Ser Ser Tyr Asp His Phe Ile Phe Thr Ala Leu
    1               5                   10                  15

GCT TTC TTC ATA TCT GGC CTA ATT TTC TTC CTC AAA CAG AAA TCC AAA        96
Ala Phe Phe Ile Ser Gly Leu Ile Phe Phe Leu Lys Gln Lys Ser Lys
                20                  25                  30

TCC AAA AAG TTC AAC CTC CCT CCA GGA CCC CCC GGG TGG CCT ATT GTT      144
Ser Lys Lys Phe Asn Leu Pro Pro Gly Pro Pro Gly Trp Pro Ile Val
            35                  40                  45
```

-continued

| | |
|---|---|
| GGG AAC CTC TTC CAA GTT GCT CGT TCT GGG AAA CCT TTC TTT GAG TAT<br>Gly Asn Leu Phe Gln Val Ala Arg Ser Gly Lys Pro Phe Phe Glu Tyr<br>50                        55                   60 | 192 |
| GTG AAC GAT GTG AGA CTC AAA TAT GGC TCA ATC TTC ACC CTC AAG ATG<br>Val Asn Asp Val Arg Leu Lys Tyr Gly Ser Ile Phe Thr Leu Lys Met<br>65                        70                   75 | 240 |
| GGA ACA AGG ACC ATG ATC ATC CTC ACC GAC GCA AAA CTG GTC CAC GAG<br>Gly Thr Arg Thr Met Ile Ile Leu Thr Asp Ala Lys Leu Val His Glu<br>80                        85                   90                   95 | 288 |
| GCC ATG ATC CAA AAG GGT GCA ACC TAC GCC ACC AGG CCC CCC GAG AAC<br>Ala Met Ile Gln Lys Gly Ala Thr Tyr Ala Thr Arg Pro Pro Glu Asn<br>100                     105                  110 | 336 |
| CCC ACC AGA ACC ATC TTC AGT GAA AAC AAG TTC ACC GTG AAT GCA GCG<br>Pro Thr Arg Thr Ile Phe Ser Glu Asn Lys Phe Thr Val Asn Ala Ala<br>115                     120                  125 | 384 |
| ACC TAT GGC CCC GTG TGG AAG TCG CTG AGG AGG AAC ATG GTG CAG AAC<br>Thr Tyr Gly Pro Val Trp Lys Ser Leu Arg Arg Asn Met Val Gln Asn<br>130                     135                  140 | 432 |
| ATG CTC AGC TCA ACA AGA CTT AAG GAG TTT CGC AGT GTT CGG GAC AAT<br>Met Leu Ser Ser Thr Arg Leu Lys Glu Phe Arg Ser Val Arg Asp Asn<br>145                     150                  155 | 480 |
| GCG ATG GAC AAG CTC ATC AAC AGA CTC AAG GAC GAG GCC GAG AAG AAT<br>Ala Met Asp Lys Leu Ile Asn Arg Leu Lys Asp Glu Ala Glu Lys Asn<br>160                     165                  170                  175 | 528 |
| AAC GGC GTG GTT TGG GTG CTC AAG GAT GCC AGG TTT GCT GTT TTT TGC<br>Asn Gly Val Val Trp Val Leu Lys Asp Ala Arg Phe Ala Val Phe Cys<br>180                     185                  190 | 576 |
| ATA CTT GTG GCT ATG TGT TTT GGT CTT GAG ATG GAT GAG GAG ACA GTG<br>Ile Leu Val Ala Met Cys Phe Gly Leu Glu Met Asp Glu Glu Thr Val<br>195                     200                  205 | 624 |
| GAG AGA ATA GAT CAG GTT ATG AAG AGT GTT CTC ATC ACT TTG GAC CCG<br>Glu Arg Ile Asp Gln Val Met Lys Ser Val Leu Ile Thr Leu Asp Pro<br>210                     215                  220 | 672 |
| AGA ATT GAT GAC TAT CTT CCA ATT CTA AGC CCC TTT TTC TCA AAG CAA<br>Arg Ile Asp Asp Tyr Leu Pro Ile Leu Ser Pro Phe Phe Ser Lys Gln<br>225                     230                  235 | 720 |
| AGA AAG AAA GCC TTG GAG GTT CGC AGA GAA CAG GTT GAG TTC TTA GTT<br>Arg Lys Lys Ala Leu Glu Val Arg Arg Glu Gln Val Glu Phe Leu Val<br>240                     245                  250                  255 | 768 |
| CCA ATT ATA GAA CAA AGA AGA AGA GCA ATT CAA AAC CCT GGG TCA GAT<br>Pro Ile Ile Glu Gln Arg Arg Arg Ala Ile Gln Asn Pro Gly Ser Asp<br>260                     265                  270 | 816 |
| CAC ACC GCC ACA ACG TTT TCC TAC CTA GAC ACA CTT TTT GAC CTC AAA<br>His Thr Ala Thr Thr Phe Ser Tyr Leu Asp Thr Leu Phe Asp Leu Lys<br>275                     280                  285 | 864 |
| GTT GAA GGG AAG AAA TCA GCA CCC TCT GAT GCA GAA TTG GTG TCT TTA<br>Val Glu Gly Lys Lys Ser Ala Pro Ser Asp Ala Glu Leu Val Ser Leu<br>290                     295                  300 | 912 |
| TGC TCA GAG TTT CTT AAC GGT GGC ACA GAC ACA ACA GCA ACA GCG GTT<br>Cys Ser Glu Phe Leu Asn Gly Gly Thr Asp Thr Thr Ala Thr Ala Val<br>305                     310                  315 | 960 |
| GAG TGG GGC ATA GCA CAG CTC ATA GCG AAC CCT AAC GTT CAG ACA AAG<br>Glu Trp Gly Ile Ala Gln Leu Ile Ala Asn Pro Asn Val Gln Thr Lys<br>320                     325                  330                  335 | 1008 |
| CTG TAC GAG GAA ATA AAG AGA ACG GTG GGA GAG AAG AAG GTG GAT GAA<br>Leu Tyr Glu Glu Ile Lys Arg Thr Val Gly Glu Lys Lys Val Asp Glu<br>340                     345                  350 | 1056 |
| AAG GAC GTT GAG AAA ATG CCA TAC CTA CAC GCT GTG GTG AAG GAG CTT<br>Lys Asp Val Glu Lys Met Pro Tyr Leu His Ala Val Val Lys Glu Leu<br>355                     360                  365 | 1104 |

```
CTA AGA AAG CAC CCT CCA ACA CAC TTT GTG CTA ACA CAT GCT GTG ACT      1152
Leu Arg Lys His Pro Pro Thr His Phe Val Leu Thr His Ala Val Thr
            370                 375                 380

GAG CCC ACC ACT TTG GGA GGG TAT GAC ATA CCA ATT GAT GCA AAT GTT      1200
Glu Pro Thr Thr Leu Gly Gly Tyr Asp Ile Pro Ile Asp Ala Asn Val
385                 390                 395

GAG GTG TAC ACA CCA GCC ATT GCT GAG GAC CCC AAA AAT TGG TTA AAC      1248
Glu Val Tyr Thr Pro Ala Ile Ala Glu Asp Pro Lys Asn Trp Leu Asn
400                 405                 410                 415

CCT GAG AAG TTT GAC CCT GAG AGA TTC ATC TCT GGG GGT GAG GAA GCA      1296
Pro Glu Lys Phe Asp Pro Glu Arg Phe Ile Ser Gly Gly Glu Glu Ala
                420                 425                 430

GAC ATA ACT GGG GTC ACA GGG GTG AAG ATG ATG CCA TTT GGG GTT GGG      1344
Asp Ile Thr Gly Val Thr Gly Val Lys Met Met Pro Phe Gly Val Gly
            435                 440                 445

AGA AGG ATT TGC CCT GGC TTG GCT ATG GCC ACA GTG CAT ATT CAC CTC      1392
Arg Arg Ile Cys Pro Gly Leu Ala Met Ala Thr Val His Ile His Leu
            450                 455                 460

ATG ATG GCA AGG ATG GTG CAG GAG TTT GAG TGG GGT GCA TAC CCT CCA      1440
Met Met Ala Arg Met Val Gln Glu Phe Glu Trp Gly Ala Tyr Pro Pro
465                 470                 475

GAG AAG AAG ATG GAT TTC ACT GGC AAG TGG GAG TTC ACT GTG GTC ATG      1488
Glu Lys Lys Met Asp Phe Thr Gly Lys Trp Glu Phe Thr Val Val Met
480                 485                 490                 495

AAG GAG TCT CTA AGA GCA ACC ATC AAA CCA AGA GGA GGA GAA AAA GTG      1536
Lys Glu Ser Leu Arg Ala Thr Ile Lys Pro Arg Gly Gly Glu Lys Val
                500                 505                 510

AAG TTG TAAAATTTTC CTGCTTCTAT TCTTCTGGGT TTTAAATTTC ACAGACAACA       1592
Lys Leu

TAAATATTAT TGCTATTATC ATCATCATAT ATGTATACAT CATCATGGTT AC            1644

(2) INFORMATION FOR SEQ ID NO:6:

(i) SEQUENCE CHARACTERISTICS:
        (A) LENGTH: 513 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Thr Leu Ser Ser Tyr Asp His Phe Ile Phe Thr Ala Leu Ala
  1               5                  10                  15

Phe Phe Ile Ser Gly Leu Ile Phe Phe Leu Lys Gln Lys Ser Lys Ser
                 20                  25                  30

Lys Lys Phe Asn Leu Pro Pro Gly Pro Pro Gly Trp Pro Ile Val Gly
             35                  40                  45

Asn Leu Phe Gln Val Ala Arg Ser Gly Lys Pro Phe Phe Glu Tyr Val
         50                  55                  60

Asn Asp Val Arg Leu Lys Tyr Gly Ser Ile Phe Thr Leu Lys Met Gly
 65                  70                  75                  80

Thr Arg Thr Met Ile Ile Leu Thr Asp Ala Lys Leu Val His Glu Ala
                 85                  90                  95

Met Ile Gln Lys Gly Ala Thr Tyr Ala Thr Arg Pro Pro Glu Asn Pro
            100                 105                 110

Thr Arg Thr Ile Phe Ser Glu Asn Lys Phe Thr Val Asn Ala Ala Thr
        115                 120                 125
```

```
Tyr Gly Pro Val Trp Lys Ser Leu Arg Arg Asn Met Val Gln Asn Met
    130                 135                 140

Leu Ser Ser Thr Arg Leu Lys Glu Phe Arg Ser Val Arg Asp Asn Ala
145                 150                 155                 160

Met Asp Lys Leu Ile Asn Arg Leu Lys Asp Glu Ala Glu Lys Asn Asn
                165                 170                 175

Gly Val Val Trp Val Leu Lys Asp Ala Arg Phe Ala Val Phe Cys Ile
                180                 185                 190

Leu Val Ala Met Cys Phe Gly Leu Glu Met Asp Glu Glu Thr Val Glu
            195                 200                 205

Arg Ile Asp Gln Val Met Lys Ser Val Leu Ile Thr Leu Asp Pro Arg
    210                 215                 220

Ile Asp Asp Tyr Leu Pro Ile Leu Ser Pro Phe Ser Lys Gln Arg
225                 230                 235                 240

Lys Lys Ala Leu Glu Val Arg Arg Glu Gln Val Glu Phe Leu Val Pro
                245                 250                 255

Ile Ile Glu Gln Arg Arg Ala Ile Gln Asn Pro Gly Ser Asp His
                260                 265                 270

Thr Ala Thr Thr Phe Ser Tyr Leu Asp Thr Leu Phe Asp Leu Lys Val
            275                 280                 285

Glu Gly Lys Lys Ser Ala Pro Ser Asp Ala Glu Leu Val Ser Leu Cys
    290                 295                 300

Ser Glu Phe Leu Asn Gly Gly Thr Asp Thr Thr Ala Thr Ala Val Glu
305                 310                 315                 320

Trp Gly Ile Ala Gln Leu Ile Ala Asn Pro Asn Val Gln Thr Lys Leu
                325                 330                 335

Tyr Glu Glu Ile Lys Arg Thr Val Gly Glu Lys Lys Val Asp Glu Lys
                340                 345                 350

Asp Val Glu Lys Met Pro Tyr Leu His Ala Val Val Lys Glu Leu Leu
            355                 360                 365

Arg Lys His Pro Pro Thr His Phe Val Leu Thr His Ala Val Thr Glu
    370                 375                 380

Pro Thr Thr Leu Gly Gly Tyr Asp Ile Pro Ile Asp Ala Asn Val Glu
385                 390                 395                 400

Val Tyr Thr Pro Ala Ile Ala Glu Asp Pro Lys Asn Trp Leu Asn Pro
                405                 410                 415

Glu Lys Phe Asp Pro Glu Arg Phe Ile Ser Gly Gly Glu Glu Ala Asp
                420                 425                 430

Ile Thr Gly Val Thr Gly Val Lys Met Met Pro Phe Gly Val Gly Arg
            435                 440                 445

Arg Ile Cys Pro Gly Leu Ala Met Ala Thr Val His Ile His Leu Met
    450                 455                 460

Met Ala Arg Met Val Gln Glu Phe Glu Trp Gly Ala Tyr Pro Pro Glu
465                 470                 475                 480

Lys Lys Met Asp Phe Thr Gly Lys Trp Glu Phe Thr Val Val Met Lys
                485                 490                 495

Glu Ser Leu Arg Ala Thr Ile Lys Pro Arg Gly Gly Glu Lys Val Lys
            500                 505                 510

Leu (2) INFORMATION FOR SEQ ID NO:7:
```

(i) SEQUENCE CHARACTERISTICS:
    (A) LENGTH: 1611 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 20..1588

(xi) SEQUENCE DESCRIPTION: SEQ ID NO:7:

```
AAGCACTATC CCTCCCACC ATG ACA AGC CAC ATT GAC GAC AAC CTC TGG ATA        52
                    Met Thr Ser His Ile Asp Asp Asn Leu Trp Ile
                     1               5                  10

ATA GCC CTG ACC TCG AAA TGC ACC CAA GAA AAC CTT GCA TGG GTC CTT        100
Ile Ala Leu Thr Ser Lys Cys Thr Gln Glu Asn Leu Ala Trp Val Leu
             15                  20                  25

TTG ATC ATG GGC TCA CTC TGG TTA ACC ATG ACT TTC TAT TAC TGG TCA        148
Leu Ile Met Gly Ser Leu Trp Leu Thr Met Thr Phe Tyr Tyr Trp Ser
         30                  35                  40

CAC CCC GGT GGT CCT GCC TGG GGC AAG TAC TAC ACC TAC TCT CCC CCC        196
His Pro Gly Gly Pro Ala Trp Gly Lys Tyr Tyr Thr Tyr Ser Pro Pro
     45                  50                  55

CTT TCA ATC ATT CCC GGT CCC AAA GGC TTC CCT CTT ATT GGA AGC ATG        244
Leu Ser Ile Ile Pro Gly Pro Lys Gly Phe Pro Leu Ile Gly Ser Met
 60                  65                  70                  75

GGC CTC ATG ACT TCC CTG GCC CAT CAC CGT ATC GCA GCC GCG GCC GCC        292
Gly Leu Met Thr Ser Leu Ala His His Arg Ile Ala Ala Ala Ala Ala
                 80                  85                  90

ACA TGC AGA GCC AAG CGC CTC ATG GCC TTT AGT CTC GGC GAC ACA CGT        340
Thr Cys Arg Ala Lys Arg Leu Met Ala Phe Ser Leu Gly Asp Thr Arg
             95                 100                 105

GTC ATC GTC ACG TGC CAC CCC GAC GTG GCC AAG GAG ATT CTC AAC AGC        388
Val Ile Val Thr Cys His Pro Asp Val Ala Lys Glu Ile Leu Asn Ser
         110                 115                 120

TCC GTC TTC GCC GAT CGT CCC GTC AAA GAA TCC GCA TAC AGC CTC ATG        436
Ser Val Phe Ala Asp Arg Pro Val Lys Glu Ser Ala Tyr Ser Leu Met
     125                 130                 135

TTT AAC CGC GCC ATC GGC TTC GCC TCT TAC GGA GTT TAC TGG CGA AGC        484
Phe Asn Arg Ala Ile Gly Phe Ala Ser Tyr Gly Val Tyr Trp Arg Ser
140                 145                 150                 155

CTC AGG AGA ATC GCC TCT AAT CAC CTC TTC TGC CCC CGC CAG ATA AAA        532
Leu Arg Arg Ile Ala Ser Asn His Leu Phe Cys Pro Arg Gln Ile Lys
                 160                 165                 170

GCC TCT GAG CTC CAA CGC TCT CAA ATC GCC GCC CAA ATG GTT CAC ATC        580
Ala Ser Glu Leu Gln Arg Ser Gln Ile Ala Ala Gln Met Val His Ile
             175                 180                 185

CTA AAT AAC AAG CGC CAC CGC AGC TTA CGT GTT CGC CAA GTG CTG AAA        628
Leu Asn Asn Lys Arg His Arg Ser Leu Arg Val Arg Gln Val Leu Lys
         190                 195                 200

AAG GCT TCG CTC AGT AAC ATG ATG TGC TCC GTG TTT GGA CAA GAG TAT        676
Lys Ala Ser Leu Ser Asn Met Met Cys Ser Val Phe Gly Gln Glu Tyr
     205                 210                 215

AAG CTG CAC GAC CCA AAC AGC GGA ATG GAA GAC CTT GGA ATA TTA GTG        724
Lys Leu His Asp Pro Asn Ser Gly Met Glu Asp Leu Gly Ile Leu Val
220                 225                 230                 235

GAC CAA GGT TAT GAC CTG TTG GGC CTG TTT AAT TGG GCC GAC CAC CTT        772
Asp Gln Gly Tyr Asp Leu Leu Gly Leu Phe Asn Trp Ala Asp His Leu
                 240                 245                 250
```

```
CCT TTT CTT GCA CAT TTC GAC GCC CAA AAT ATC CGG TTC AGG TGC TCC      820
Pro Phe Leu Ala His Phe Asp Ala Gln Asn Ile Arg Phe Arg Cys Ser
            255                 260                 265

AAC CTC GTC CCC ATG GTG AAC CGT TTC GTC GGC ACA ATC ATC GCT GAA      868
Asn Leu Val Pro Met Val Asn Arg Phe Val Gly Thr Ile Ile Ala Glu
                270                 275                 280

CAC CGA GCT AGT AAA ACC GAA ACC AAT CGT GAT TTT GTT GAC GTC TTG      916
His Arg Ala Ser Lys Thr Glu Thr Asn Arg Asp Phe Val Asp Val Leu
285                 290                 295

CTC TCT CTC CCG GAA CCT GAT CAA TTA TCA GAC TCC GAC ATG ATC GCT      964
Leu Ser Leu Pro Glu Pro Asp Gln Leu Ser Asp Ser Asp Met Ile Ala
300                 305                 310                 315

GTA CTT TGG GAA ATG ATA TTC AGA GGA ACG GAC ACG GTA GCG GTT TTG     1012
Val Leu Trp Glu Met Ile Phe Arg Gly Thr Asp Thr Val Ala Val Leu
                320                 325                 330

ATA GAG TGG ATA CTC GCG AGG ATG GCG CTT CAT CCT CAT GTG CAG TCC     1060
Ile Glu Trp Ile Leu Ala Arg Met Ala Leu His Pro His Val Gln Ser
            335                 340                 345

AAA GTT CAA GAG GAG CTA GAT GCA GTT GTC GGA AAA GCA CGC GCC GTC     1108
Lys Val Gln Glu Glu Leu Asp Ala Val Val Gly Lys Ala Arg Ala Val
        350                 355                 360

GCA GAG GAT GAC GTG GCA GTG ATG ACG TAC CTA CCA GCG GTG GTG AAG     1156
Ala Glu Asp Asp Val Ala Val Met Thr Tyr Leu Pro Ala Val Val Lys
365                 370                 375

GAG GTG CTG CGG CTG CAC CCG CCG GGC CCA CTT CTA TCA TGG GCC CGC     1204
Glu Val Leu Arg Leu His Pro Pro Gly Pro Leu Leu Ser Trp Ala Arg
380                 385                 390                 395

TTG TCC ATC AAT GAT ACG ACC ATT GAT GGG TAT CAC GTA CCT GCG GGG     1252
Leu Ser Ile Asn Asp Thr Thr Ile Asp Gly Tyr His Val Pro Ala Gly
                400                 405                 410

ACC ACT GCT ATG GTC AAC ACG TGG GCT ATT TGC AGG GAC CCA CAC GTG     1300
Thr Thr Ala Met Val Asn Thr Trp Ala Ile Cys Arg Asp Pro His Val
            415                 420                 425

TGG AAG GAC CCA CTC GAA TTT ATG CCC GAG AGG TTT GTC ACT GCG GGT     1348
Trp Lys Asp Pro Leu Glu Phe Met Pro Glu Arg Phe Val Thr Ala Gly
        430                 435                 440

GGA GAT GCC GAA TTT TCG ATA CTC GGG TCG GAT CCA AGA CTT GCT CCA     1396
Gly Asp Ala Glu Phe Ser Ile Leu Gly Ser Asp Pro Arg Leu Ala Pro
445                 450                 455

TTT GGG TCG GGT AGG AGA GCG TGC CCA GGG AAG ACT CTT GGA TGG GCT     1444
Phe Gly Ser Gly Arg Arg Ala Cys Pro Gly Lys Thr Leu Gly Trp Ala
460                 465                 470                 475

ACG GTG AAC TTT TGG GTG GCG TCG CTC TTG CAT GAG TTC GAA TGG GTA     1492
Thr Val Asn Phe Trp Val Ala Ser Leu Leu His Glu Phe Glu Trp Val
                480                 485                 490

CCG TCT GAT GAG AAG GGT GTT GAT CTG ACG GAG GTG CTG AAG CTC TCT     1540
Pro Ser Asp Glu Lys Gly Val Asp Leu Thr Glu Val Leu Lys Leu Ser
            495                 500                 505

AGT GAA ATG GCT AAC CCT CTC ACC GTC AAA GTG CGC CCC AGG CGT GGA     1588
Ser Glu Met Ala Asn Pro Leu Thr Val Lys Val Arg Pro Arg Arg Gly
        510                 515                 520

TAAGAGAGAG TTGAAGCTTT TAT                                           1611
```

(2) INFORMATION FOR SEQ ID NO:8:

(i) SEQUENCE CHARACTERISTICS:
        (A) LENGTH: 523 amino acids
        (B) TYPE: amino acid
        (D) TOPOLOGY: linear (ii) MOLECULE TYPE: protein (xi) SEQUENCE DESCRIPTION: SEQ ID NO:8:

```
Met Thr Ser His Ile Asp Asp Asn Leu Trp Ile Ile Ala Leu Thr Ser
 1               5                  10                  15

Lys Cys Thr Gln Glu Asn Leu Ala Trp Val Leu Leu Ile Met Gly Ser
                 20                  25                  30

Leu Trp Leu Thr Met Thr Phe Tyr Tyr Trp Ser His Pro Gly Gly Pro
             35                  40                  45

Ala Trp Gly Lys Tyr Tyr Thr Tyr Ser Pro Pro Leu Ser Ile Ile Pro
 50                  55                  60

Gly Pro Lys Gly Phe Pro Leu Ile Gly Ser Met Gly Leu Met Thr Ser
 65                  70                  75                  80

Leu Ala His His Arg Ile Ala Ala Ala Ala Thr Cys Arg Ala Lys
                 85                  90                  95

Arg Leu Met Ala Phe Ser Leu Gly Asp Thr Arg Val Ile Val Thr Cys
                100                 105                 110

His Pro Asp Val Ala Lys Glu Ile Leu Asn Ser Ser Val Phe Ala Asp
            115                 120                 125

Arg Pro Val Lys Glu Ser Ala Tyr Ser Leu Met Phe Asn Arg Ala Ile
        130                 135                 140

Gly Phe Ala Ser Tyr Gly Val Tyr Trp Arg Ser Leu Arg Arg Ile Ala
145                 150                 155                 160

Ser Asn His Leu Phe Cys Pro Arg Gln Ile Lys Ala Ser Glu Leu Gln
                165                 170                 175

Arg Ser Gln Ile Ala Ala Gln Met Val His Ile Leu Asn Asn Lys Arg
            180                 185                 190

His Arg Ser Leu Arg Val Arg Gln Val Leu Lys Lys Ala Ser Leu Ser
        195                 200                 205

Asn Met Met Cys Ser Val Phe Gly Gln Glu Tyr Lys Leu His Asp Pro
    210                 215                 220

Asn Ser Gly Met Glu Asp Leu Gly Ile Leu Val Asp Gln Gly Tyr Asp
225                 230                 235                 240

Leu Leu Gly Leu Phe Asn Trp Ala Asp His Leu Pro Phe Leu Ala His
                245                 250                 255

Phe Asp Ala Gln Asn Ile Arg Phe Arg Cys Ser Asn Leu Val Pro Met
            260                 265                 270

Val Asn Arg Phe Val Gly Thr Ile Ile Ala Glu His Arg Ala Ser Lys
        275                 280                 285

Thr Glu Thr Asn Arg Asp Phe Val Asp Val Leu Leu Ser Leu Pro Glu
    290                 295                 300

Pro Asp Gln Leu Ser Asp Ser Asp Met Ile Ala Val Leu Trp Glu Met
305                 310                 315                 320

Ile Phe Arg Gly Thr Asp Thr Val Ala Val Leu Ile Glu Trp Ile Leu
                325                 330                 335

Ala Arg Met Ala Leu His Pro His Val Gln Ser Lys Val Gln Glu Glu
            340                 345                 350

Leu Asp Ala Val Val Gly Lys Ala Arg Ala Val Ala Glu Asp Asp Val
        355                 360                 365

Ala Val Met Thr Tyr Leu Pro Ala Val Val Lys Glu Val Leu Arg Leu
    370                 375                 380

His Pro Pro Gly Pro Leu Leu Ser Trp Ala Arg Leu Ser Ile Asn Asp
385                 390                 395                 400
```

```
Thr Thr Ile Asp Gly Tyr His Val Pro Ala Gly Thr Thr Ala Met Val
            405                 410                 415

Asn Thr Trp Ala Ile Cys Arg Asp Pro His Val Trp Lys Asp Pro Leu
            420                 425                 430

Glu Phe Met Pro Glu Arg Phe Val Thr Ala Gly Gly Asp Ala Glu Phe
            435                 440                 445

Ser Ile Leu Gly Ser Asp Pro Arg Leu Ala Pro Phe Gly Ser Gly Arg
    450                 455                 460

Arg Ala Cys Pro Gly Lys Thr Leu Gly Trp Ala Thr Val Asn Phe Trp
465                 470                 475                 480

Val Ala Ser Leu Leu His Glu Phe Glu Trp Val Pro Ser Asp Glu Lys
            485                 490                 495

Gly Val Asp Leu Thr Glu Val Leu Lys Leu Ser Ser Glu Met Ala Asn
            500                 505                 510

Pro Leu Thr Val Lys Val Arg Pro Arg Arg Gly
            515                 520
```

(2) INFORMATION FOR SEQ ID NO:9:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 6..1601

(xi) SEQUENCE DESCRIPTION: SEQ ID NO:9:

```
GGGTC ATG GGC ATG GCC ATG GAT GCT TTC CAG CAC CAA ACT CTC ATT        47
      Met Gly Met Ala Met Asp Ala Phe Gln His Gln Thr Leu Ile
       1               5                  10

TCC ATC ATT CTG GCC ATG TTA GTA GGC GTG TTG ATT TAT GGC TTA AAG      95
Ser Ile Ile Leu Ala Met Leu Val Gly Val Leu Ile Tyr Gly Leu Lys
 15                  20                  25                  30

AGA ACA CAT AGT GGC CAT GGC AAG ATC TGT AGT GCA CCT CAA GCA GGA     143
Arg Thr His Ser Gly His Gly Lys Ile Cys Ser Ala Pro Gln Ala Gly
             35                  40                  45

GGA GCA TGG CCA ATT ATT GGC CAT TTA CAC CTC TTT GGG GGT CAT CAA     191
Gly Ala Trp Pro Ile Ile Gly His Leu His Leu Phe Gly Gly His Gln
         50                  55                  60

CAT ACT CAC AAA ACA CTT GGG ATA ATG GCA GAG AAA CAT GGA CCA ATT     239
His Thr His Lys Thr Leu Gly Ile Met Ala Glu Lys His Gly Pro Ile
 65                  70                  75

TTC ACA ATA AAG CTT GGT TCA TAC AAA GTT CTT GTA TTG AGT AGC TGG     287
Phe Thr Ile Lys Leu Gly Ser Tyr Lys Val Leu Val Leu Ser Ser Trp
         80                  85                  90

GAG ATG GCC AAG GAG TGT TTC ACT GTC CAT GAC AAA GCA TTT TCT ACC     335
Glu Met Ala Lys Glu Cys Phe Thr Val His Asp Lys Ala Phe Ser Thr
 95                 100                 105                 110

AGA CCC TGT GTT GCA GCC TCA AAG CTA ATG GGC TAC AAC TAT GCC ATG     383
Arg Pro Cys Val Ala Ala Ser Lys Leu Met Gly Tyr Asn Tyr Ala Met
             115                 120                 125

TTT GGC TTC ACT CCT TAT GGT CCT TAT TGG CGT GAG ATA AGG AAA TTA     431
Phe Gly Phe Thr Pro Tyr Gly Pro Tyr Trp Arg Glu Ile Arg Lys Leu
         130                 135                 140
```

```
ACT ACT ATT CAG CTT CTA TCT AAC CAC CGG CTT GAA CTG CTG AAG AAC         479
Thr Thr Ile Gln Leu Leu Ser Asn His Arg Leu Glu Leu Leu Lys Asn
        145                 150                 155

ACA AGA ACA TCT GAG TCA GAA GTT GCA ATA AGA GAG CTT TAT AAG TTG         527
Thr Arg Thr Ser Glu Ser Glu Val Ala Ile Arg Glu Leu Tyr Lys Leu
    160                 165                 170

TGG TCT AGA GAA GGT TGT CCA AAG GGA GGG GTT TTG GTA GAT ATG AAG         575
Trp Ser Arg Glu Gly Cys Pro Lys Gly Gly Val Leu Val Asp Met Lys
175                 180                 185                 190

CAG TGG TTT GGG GAT TTA ACT CAT AAT ATT GTT CTG AGA ATG GTG AGA         623
Gln Trp Phe Gly Asp Leu Thr His Asn Ile Val Leu Arg Met Val Arg
                195                 200                 205

GGG AAG CCA TAC TAT GAT GGT GCT AGT GAT GAT TAT GCA GAA GGT GAA         671
Gly Lys Pro Tyr Tyr Asp Gly Ala Ser Asp Asp Tyr Ala Glu Gly Glu
        210                 215                 220

GCA AGA AGG TAC AAG AAA GTT ATG GGA GAG TGT GTG AGT TTG TTT GGG         719
Ala Arg Arg Tyr Lys Lys Val Met Gly Glu Cys Val Ser Leu Phe Gly
    225                 230                 235

GTG TTT GTG TTA TCT GAT GCT ATT CCA TTT CTG GGG TGG TTG GAC ATC         767
Val Phe Val Leu Ser Asp Ala Ile Pro Phe Leu Gly Trp Leu Asp Ile
240                 245                 250

AAC GGA TAT GAA AAG GCC ATG AAG AGA ACT GCA AGT GAA TTG GAT CCT         815
Asn Gly Tyr Glu Lys Ala Met Lys Arg Thr Ala Ser Glu Leu Asp Pro
255                 260                 265                 270

CTG GTT GAA GGG TGG TTA GAG GAA CAC AAA AGG AAA AGA GCT TTC AAT         863
Leu Val Glu Gly Trp Leu Glu Glu His Lys Arg Lys Arg Ala Phe Asn
                275                 280                 285

ATG GAT GCA AAA GAA GAA CAG GAT AAT TTC ATG GAT GTC ATG CTG AAT         911
Met Asp Ala Lys Glu Glu Gln Asp Asn Phe Met Asp Val Met Leu Asn
            290                 295                 300

GTT CTG AAA GAT GCA GAG ATT TCT GGT TAT GAT TCA GAT ACC ATC ATC         959
Val Leu Lys Asp Ala Glu Ile Ser Gly Tyr Asp Ser Asp Thr Ile Ile
        305                 310                 315

AAG GCT ACT TGT CTG AAT CTG ATT TTA GCA GGA AGC GAC ACC ACC ATG        1007
Lys Ala Thr Cys Leu Asn Leu Ile Leu Ala Gly Ser Asp Thr Thr Met
    320                 325                 330

ATT TCA CTA ACA TGG GTG CTA TCT CTG CTA CTT AAC CAT CAA ATG GAA        1055
Ile Ser Leu Thr Trp Val Leu Ser Leu Leu Leu Asn His Gln Met Glu
335                 340                 345                 350

CTA AAA AAA GTC CAA GAT GAA TTG GAC ACT TAT ATT GGG AAG GAC AGG        1103
Leu Lys Lys Val Gln Asp Glu Leu Asp Thr Tyr Ile Gly Lys Asp Arg
                355                 360                 365

AAG GTG GAA GAA TCT GAC ATA ACC AAG TTG GTG TAC CTC CAA GCC ATT        1151
Lys Val Glu Glu Ser Asp Ile Thr Lys Leu Val Tyr Leu Gln Ala Ile
            370                 375                 380

GTG AAG GAA ACA ATG CGG CTG TAT CCA CCA AGT CCT CTT ATC ACC CTT        1199
Val Lys Glu Thr Met Arg Leu Tyr Pro Pro Ser Pro Leu Ile Thr Leu
        385                 390                 395

CGT GCA GCC ATG GAA GAC TGC ACC TTC TCA GGT GGC TAT CAC ATT CCT        1247
Arg Ala Ala Met Glu Asp Cys Thr Phe Ser Gly Gly Tyr His Ile Pro
    400                 405                 410

GCT GGG ACA CGT TTA ATG GTG AAT GCT TGG AAG ATC CAC CGG GAT GGT        1295
Ala Gly Thr Arg Leu Met Val Asn Ala Trp Lys Ile His Arg Asp Gly
415                 420                 425                 430

CGT GTT TGG AGT GAT CCT CAT GAT TTC AAG CCT GGA AGG TTC TTG ACA        1343
Arg Val Trp Ser Asp Pro His Asp Phe Lys Pro Gly Arg Phe Leu Thr
                435                 440                 445

AGC CAC AAA GAT GTT GAT GTG AAG GGT CAG AAC TAT GAG CTC GTC CCT        1391
Ser His Lys Asp Val Asp Val Lys Gly Gln Asn Tyr Glu Leu Val Pro
            450                 455                 460
```

-continued

```
TTT GGT TCT GGA AGG AGA GCA TGC CCT GGA GCC TCG CTG GCT CTG CGT        1439
Phe Gly Ser Gly Arg Arg Ala Cys Pro Gly Ala Ser Leu Ala Leu Arg
            465                 470                 475

GTG GTG CAC TTG ACC ATG GCT AGA CTG TTA CAT TCT TTC AAT GTT GCT        1487
Val Val His Leu Thr Met Ala Arg Leu Leu His Ser Phe Asn Val Ala
        480                 485                 490

TCT CCT TCA AAT CAA GTT GTG GAC ATG ACA GAG AGC ATT GGA CTC ACA        1535
Ser Pro Ser Asn Gln Val Val Asp Met Thr Glu Ser Ile Gly Leu Thr
495                 500                 505                 510

AAT TTA AAA GCA ACC CCG CTT GAA ATT CTC CTA ACT CCA CGT CTA GAC        1583
Asn Leu Lys Ala Thr Pro Leu Glu Ile Leu Leu Thr Pro Arg Leu Asp
                515                 520                 525

ACC AAA CTT TAT GAG AAC TAGATTAAAT TAAGCTAGTT TTCTCCCAAA               1631
Thr Lys Leu Tyr Glu Asn
            530

TAAGGGGAGG GGTCCTCTAG GTCCTGAAAT CGGGTAATAA CAATAACATG GTTAATGCAG      1691

CTTCCATGTA GGATAATGAT TATTCACTCA TGGGTCACCT TTTAATGGAG CCTCAGTGTA      1751

TTATAATAAC TCCAAACTTG TGGGTCACAA TCCCCCC                               1788
```

(2) INFORMATION FOR SEQ ID NO:10:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO:10:

```
Met Gly Met Ala Met Asp Ala Phe Gln His Gln Thr Leu Ile Ser Ile
 1               5                  10                  15

Ile Leu Ala Met Leu Val Gly Val Leu Ile Tyr Gly Leu Lys Arg Thr
            20                  25                  30

His Ser Gly His Gly Lys Ile Cys Ser Ala Pro Gln Ala Gly Gly Ala
        35                  40                  45

Trp Pro Ile Ile Gly His Leu His Leu Phe Gly Gly His Gln His Thr
    50                  55                  60

His Lys Thr Leu Gly Ile Met Ala Glu Lys His Gly Pro Ile Phe Thr
65                  70                  75                  80

Ile Lys Leu Gly Ser Tyr Lys Val Leu Val Leu Ser Ser Trp Glu Met
                85                  90                  95

Ala Lys Glu Cys Phe Thr Val His Asp Lys Ala Phe Ser Thr Arg Pro
            100                 105                 110

Cys Val Ala Ala Ser Lys Leu Met Gly Tyr Asn Tyr Ala Met Phe Gly
        115                 120                 125

Phe Thr Pro Tyr Gly Pro Tyr Trp Arg Glu Ile Arg Lys Leu Thr Thr
    130                 135                 140

Ile Gln Leu Leu Ser Asn His Arg Leu Glu Leu Leu Lys Asn Thr Arg
145                 150                 155                 160

Thr Ser Glu Ser Glu Val Ala Ile Arg Glu Leu Tyr Lys Leu Trp Ser
                165                 170                 175

Arg Glu Gly Cys Pro Lys Gly Val Leu Val Asp Met Lys Gln Trp
            180                 185                 190

Phe Gly Asp Leu Thr His Asn Ile Val Leu Arg Met Val Arg Gly Lys
    195                 200                 205
```

```
Pro Tyr Tyr Asp Gly Ala Ser Asp Asp Tyr Ala Glu Gly Glu Ala Arg
    210                 215                 220

Arg Tyr Lys Lys Val Met Gly Glu Cys Val Ser Leu Phe Gly Val Phe
225                 230                 235                 240

Val Leu Ser Asp Ala Ile Pro Phe Leu Gly Trp Leu Asp Ile Asn Gly
                245                 250                 255

Tyr Glu Lys Ala Met Lys Arg Thr Ala Ser Glu Leu Asp Pro Leu Val
            260                 265                 270

Glu Gly Trp Leu Glu Glu His Lys Arg Lys Ala Phe Asn Met Asp
        275                 280                 285

Ala Lys Glu Glu Gln Asp Asn Phe Met Asp Val Met Leu Asn Val Leu
290                 295                 300

Lys Asp Ala Glu Ile Ser Gly Tyr Asp Ser Asp Thr Ile Ile Lys Ala
305                 310                 315                 320

Thr Cys Leu Asn Leu Ile Leu Ala Gly Ser Asp Thr Thr Met Ile Ser
                325                 330                 335

Leu Thr Trp Val Leu Ser Leu Leu Asn His Gln Met Glu Leu Lys
        340                 345                 350

Lys Val Gln Asp Glu Leu Asp Thr Tyr Ile Gly Lys Asp Arg Lys Val
    355                 360                 365

Glu Glu Ser Asp Ile Thr Lys Leu Val Tyr Leu Gln Ala Ile Val Lys
370                 375                 380

Glu Thr Met Arg Leu Tyr Pro Pro Ser Pro Leu Ile Thr Leu Arg Ala
385                 390                 395                 400

Ala Met Glu Asp Cys Thr Phe Ser Gly Gly Tyr His Ile Pro Ala Gly
                405                 410                 415

Thr Arg Leu Met Val Asn Ala Trp Lys Ile His Arg Asp Gly Arg Val
            420                 425                 430

Trp Ser Asp Pro His Asp Phe Lys Pro Gly Arg Phe Leu Thr Ser His
        435                 440                 445

Lys Asp Val Asp Val Lys Gly Gln Asn Tyr Glu Leu Val Pro Phe Gly
450                 455                 460

Ser Gly Arg Arg Ala Cys Pro Gly Ala Ser Leu Ala Leu Arg Val Val
465                 470                 475                 480

His Leu Thr Met Ala Arg Leu Leu His Ser Phe Asn Val Ala Ser Pro
                485                 490                 495

Ser Asn Gln Val Val Asp Met Thr Glu Ser Ile Gly Leu Thr Asn Leu
            500                 505                 510

Lys Ala Thr Pro Leu Glu Ile Leu Leu Thr Pro Arg Leu Asp Thr Lys
        515                 520                 525

Leu Tyr Glu Asn
    530

(2) INFORMATION FOR SEQ ID NO:11:

(i) SEQUENCE CHARACTERISTICS:
        (A) LENGTH: 1657 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1548

(xi) SEQUENCE DESCRIPTION: SEQ ID NO:11:
```

-continued

| | | | | | | | | | | | | | | | | |
|---|---|---|---|---|---|---|---|---|---|---|---|---|---|---|---|---|
| CTT | GTT | CTT | CTT | TCT | CTA | TTG | TCT | ATA | GTC | ATC | TCC | ATT | GTT | CTC | TTC | 48 |
| Leu | Val | Leu | Leu | Ser | Leu | Leu | Ser | Ile | Val | Ile | Ser | Ile | Val | Leu | Phe | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ATT | ACC | CAC | ACA | CAC | AAA | AGA | AAC | AAC | ACT | CCA | AGA | GGA | CCA | CCA | GGT | 96 |
| Ile | Thr | His | Thr | His | Lys | Arg | Asn | Asn | Thr | Pro | Arg | Gly | Pro | Pro | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| CCT | CCA | CCT | CTT | CCT | CTC | ATC | GGC | AAC | CTT | CAC | CAA | CTC | CAC | AAC | TCA | 144 |
| Pro | Pro | Pro | Leu | Pro | Leu | Ile | Gly | Asn | Leu | His | Gln | Leu | His | Asn | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| TCC | CCA | CAT | CTC | TGC | CTA | TGG | CAA | CTC | GCC | AAA | CTC | CAC | GGT | CCT | CTC | 192 |
| Ser | Pro | His | Leu | Cys | Leu | Trp | Gln | Leu | Ala | Lys | Leu | His | Gly | Pro | Leu | |
| 50 | | | | | 55 | | | | | 60 | | | | | | |

| | | | | | | | | | | | | | | | | |
|---|---|---|---|---|---|---|---|---|---|---|---|---|---|---|---|---|
| ATG | TCG | TTT | CGC | CTC | GGC | GCC | GTG | CAA | ACC | GTC | GTG | GTT | TCA | TCG | GCC | 240 |
| Met | Ser | Phe | Arg | Leu | Gly | Ala | Val | Gln | Thr | Val | Val | Val | Ser | Ser | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| AGA | ATC | GCC | GAA | CAA | ATC | TTG | AAA | ACC | CAC | GAC | CTC | AAC | TTC | GCT | TCC | 288 |
| Arg | Ile | Ala | Glu | Gln | Ile | Leu | Lys | Thr | His | Asp | Leu | Asn | Phe | Ala | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| AGG | CCT | CTC | TTC | GTG | GGC | CCG | AGA | AAG | CTC | TCT | TAC | GAC | GGG | TTG | GAC | 336 |
| Arg | Pro | Leu | Phe | Val | Gly | Pro | Arg | Lys | Leu | Ser | Tyr | Asp | Gly | Leu | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| ATG | GGC | TTC | GCA | CCG | TAC | GGC | CCG | TAC | TGG | AGA | GAA | ATG | AAG | AAA | CTC | 384 |
| Met | Gly | Phe | Ala | Pro | Tyr | Gly | Pro | Tyr | Trp | Arg | Glu | Met | Lys | Lys | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| TGC | ATC | GTT | CAC | CTC | TTC | AGC | GCG | CAA | CGC | GTT | CGG | TCC | TTT | CGA | CCA | 432 |
| Cys | Ile | Val | His | Leu | Phe | Ser | Ala | Gln | Arg | Val | Arg | Ser | Phe | Arg | Pro | |
| | 130 | | | | | 135 | | | | | 140 | | | | | |

| | | | | | | | | | | | | | | | | |
|---|---|---|---|---|---|---|---|---|---|---|---|---|---|---|---|---|
| ATT | CGA | GAG | AAC | GAG | GTT | GCA | AAA | ATG | GTT | CGG | AAA | CTG | TCG | GAA | CAC | 480 |
| Ile | Arg | Glu | Asn | Glu | Val | Ala | Lys | Met | Val | Arg | Lys | Leu | Ser | Glu | His | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| GAA | GCT | TCG | GGT | ACT | GTC | GTG | AAC | TTG | ACC | GAA | ACT | TTG | ATG | TCT | TTC | 528 |
| Glu | Ala | Ser | Gly | Thr | Val | Val | Asn | Leu | Thr | Glu | Thr | Leu | Met | Ser | Phe | |
| | | | | 165 | | | | | 170 | | | | | 175 | | |

| | | | | | | | | | | | | | | | | |
|---|---|---|---|---|---|---|---|---|---|---|---|---|---|---|---|---|
| ACG | AAC | TCT | TTG | ATA | TGC | AGA | ATC | GCG | TTG | GGG | AAA | AGT | TAC | GGT | TGT | 576 |
| Thr | Asn | Ser | Leu | Ile | Cys | Arg | Ile | Ala | Leu | Gly | Lys | Ser | Tyr | Gly | Cys | |
| | | | 180 | | | | | 185 | | | | | 190 | | | |

| | | | | | | | | | | | | | | | | |
|---|---|---|---|---|---|---|---|---|---|---|---|---|---|---|---|---|
| GAG | TAC | GAG | GAA | GTA | GTT | GTT | GAT | GAG | GTA | CTG | GGA | AAC | CGG | AGG | AGC | 624 |
| Glu | Tyr | Glu | Glu | Val | Val | Val | Asp | Glu | Val | Leu | Gly | Asn | Arg | Arg | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| AGG | TTG | CAG | GTT | CTG | CTC | AAC | GAG | GCT | CAA | GCG | TTG | CTT | TCG | GAG | TTT | 672 |
| Arg | Leu | Gln | Val | Leu | Leu | Asn | Glu | Ala | Gln | Ala | Leu | Leu | Ser | Glu | Phe | |
| | 210 | | | | | 215 | | | | | 220 | | | | | |

| | | | | | | | | | | | | | | | | |
|---|---|---|---|---|---|---|---|---|---|---|---|---|---|---|---|---|
| TTC | TTT | TCG | GAT | TAT | TTT | CCG | CCT | ATA | GGA | AAG | TGG | GTT | GAT | AGA | GTG | 720 |
| Phe | Phe | Ser | Asp | Tyr | Phe | Pro | Pro | Ile | Gly | Lys | Trp | Val | Asp | Arg | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ACG | GGA | ATT | CTA | TCG | CGG | CTT | GAT | AAA | ACG | TTC | AAG | GAG | TTG | GAC | GCG | 768 |
| Thr | Gly | Ile | Leu | Ser | Arg | Leu | Asp | Lys | Thr | Phe | Lys | Glu | Leu | Asp | Ala | |
| | | | | 245 | | | | | 250 | | | | | 255 | | |

| | | | | | | | | | | | | | | | | |
|---|---|---|---|---|---|---|---|---|---|---|---|---|---|---|---|---|
| TGC | TAC | GAA | CGA | TCA | TCC | TAT | GAT | CAC | ATG | GAT | TCG | GCA | AAG | AGT | GGT | 816 |
| Cys | Tyr | Glu | Arg | Ser | Ser | Tyr | Asp | His | Met | Asp | Ser | Ala | Lys | Ser | Gly | |
| | | | 260 | | | | | 265 | | | | | 270 | | | |

| | | | | | | | | | | | | | | | | |
|---|---|---|---|---|---|---|---|---|---|---|---|---|---|---|---|---|
| AAA | AAA | GAT | AAT | GAC | AAC | AAA | GAA | GTC | AAA | GAT | ATT | ATT | GAT | ATT | CTT | 864 |
| Lys | Lys | Asp | Asn | Asp | Asn | Lys | Glu | Val | Lys | Asp | Ile | Ile | Asp | Ile | Leu | |
| | | 275 | | | | | 280 | | | | | 285 | | | | |

| | | | | | | | | | | | | | | | | |
|---|---|---|---|---|---|---|---|---|---|---|---|---|---|---|---|---|
| CTC | CAG | CTA | CTT | GAT | GAT | CGT | TCC | TTC | ACC | TTT | GAT | CTC | ACT | CTC | GAC | 912 |
| Leu | Gln | Leu | Leu | Asp | Asp | Arg | Ser | Phe | Thr | Phe | Asp | Leu | Thr | Leu | Asp | |
| | 290 | | | | | 295 | | | | | 300 | | | | | |

```
CAC ATA AAA GCC GTG CTC ATG AAC ATC TTT ATA GCA GGA ACA GAC CCG          960
His Ile Lys Ala Val Leu Met Asn Ile Phe Ile Ala Gly Thr Asp Pro
305                 310                 315                 320

AGT TCC GCG ACA ATA GTT TGG GCA ATG AAT GCA CTG TTG AAG AAT CCC         1008
Ser Ser Ala Thr Ile Val Trp Ala Met Asn Ala Leu Leu Lys Asn Pro
            325                 330                 335

AAT GTG ATG AGC AAG GTT CAA GGA GAA GTG AGA AAT CTA TTC GGT GAC         1056
Asn Val Met Ser Lys Val Gln Gly Glu Val Arg Asn Leu Phe Gly Asp
                340                 345                 350

AAA GAT TTC ATA AAC GAA GAT GAT GTC GAA AGC CTT CCT TAT CTC AAA         1104
Lys Asp Phe Ile Asn Glu Asp Asp Val Glu Ser Leu Pro Tyr Leu Lys
        355                 360                 365

GCA GTG GTG AAG GAG ACA TTA AGA TTA TTC CCA CCT TCA CCA CTA CTT         1152
Ala Val Val Lys Glu Thr Leu Arg Leu Phe Pro Pro Ser Pro Leu Leu
370                 375                 380

TTG CCA AGG GTA ACA ATG GAA ACA TGC AAC ATA GAA GGG TAC GAA ATT         1200
Leu Pro Arg Val Thr Met Glu Thr Cys Asn Ile Glu Gly Tyr Glu Ile
385                 390                 395                 400

CAA GCC AAA ACT ATA GTG CAT GTT AAT GCA TGG GCC ATA GCA AGG GAC         1248
Gln Ala Lys Thr Ile Val His Val Asn Ala Trp Ala Ile Ala Arg Asp
            405                 410                 415

CCT GAG AAT TGG GAA GAG CCT GAG AAA TTT TTC CCC GAA AGG TTC CTT         1296
Pro Glu Asn Trp Glu Glu Pro Glu Lys Phe Phe Pro Glu Arg Phe Leu
                420                 425                 430

GAG AGT TCG ATG GAG TTA AAG GGG AAT GAT GAG TTT AAG GTG ATC CCG         1344
Glu Ser Ser Met Glu Leu Lys Gly Asn Asp Glu Phe Lys Val Ile Pro
        435                 440                 445

TTT GGT TCT GGA AGG AGA ATG TGT CCT GCG AAG CAC ATG GGA ATT ATG         1392
Phe Gly Ser Gly Arg Arg Met Cys Pro Ala Lys His Met Gly Ile Met
450                 455                 460

AAT GTT GAG CTT TCT CTT GCT AAT CTC ATT CAC ACG TTT GAT TGG GAA         1440
Asn Val Glu Leu Ser Leu Ala Asn Leu Ile His Thr Phe Asp Trp Glu
465                 470                 475                 480

GTG GCT AAA GGG TTC GAC AAG GAA GAA ATG TTG GAC ACG CAA ATG AAA         1488
Val Ala Lys Gly Phe Asp Lys Glu Glu Met Leu Asp Thr Gln Met Lys
            485                 490                 495

CCA GGA ATA ACG ATG CAC AAG AAA AGT GAT CTT TAC CTA GTG GCA AAG         1536
Pro Gly Ile Thr Met His Lys Lys Ser Asp Leu Tyr Leu Val Ala Lys
                500                 505                 510

AAA CCG ACA ACG TAGCACACGT TGGTACATTC ACTATAACAC ACAAGAAAGT             1588
Lys Pro Thr Thr
        515

TGATAATGAC TTGTGTATGC AACTATGCTC TATGCACTAT GCACTATGTT TATTGACCAT      1648

TAATTACTG                                                               1657

(2) INFORMATION FOR SEQ ID NO:12:

(i) SEQUENCE CHARACTERISTICS:
        (A) LENGTH: 516 amino acids
        (B) TYPE: amino acid
        (D) TOPOLOGY: linear (ii) MOLECULE TYPE: protein (xi) SEQUENCE DESCRIPTION: SEQ ID NO:12:

Leu Val Leu Leu Ser Leu Leu Ser Ile Val Ile Ser Ile Val Leu Phe
1               5                   10                  15

Ile Thr His Thr His Lys Arg Asn Asn Thr Pro Arg Gly Pro Pro Gly
            20                  25                  30
```

```
Pro Pro Pro Leu Pro Leu Ile Gly Asn Leu His Gln Leu His Asn Ser
         35              40              45

Ser Pro His Leu Cys Leu Trp Gln Leu Ala Lys Leu His Gly Pro Leu
     50              55              60

Met Ser Phe Arg Leu Gly Ala Val Gln Thr Val Val Ser Ser Ala
 65              70              75              80

Arg Ile Ala Glu Gln Ile Leu Lys Thr His Asp Leu Asn Phe Ala Ser
             85              90              95

Arg Pro Leu Phe Val Gly Pro Arg Lys Leu Ser Tyr Asp Gly Leu Asp
             100             105             110

Met Gly Phe Ala Pro Tyr Gly Pro Tyr Trp Arg Glu Met Lys Lys Leu
         115             120             125

Cys Ile Val His Leu Phe Ser Ala Gln Arg Val Arg Ser Phe Arg Pro
         130             135             140

Ile Arg Glu Asn Glu Val Ala Lys Met Val Arg Lys Leu Ser Glu His
145             150             155             160

Glu Ala Ser Gly Thr Val Val Asn Leu Thr Glu Thr Leu Met Ser Phe
                 165             170             175

Thr Asn Ser Leu Ile Cys Arg Ile Ala Leu Gly Lys Ser Tyr Gly Cys
             180             185             190

Glu Tyr Glu Glu Val Val Val Asp Glu Val Leu Gly Asn Arg Arg Ser
     195             200             205

Arg Leu Gln Val Leu Leu Asn Glu Ala Gln Ala Leu Leu Ser Glu Phe
     210             215             220

Phe Phe Ser Asp Tyr Phe Pro Pro Ile Gly Lys Trp Val Asp Arg Val
225             230             235             240

Thr Gly Ile Leu Ser Arg Leu Asp Lys Thr Phe Lys Glu Leu Asp Ala
                 245             250             255

Cys Tyr Glu Arg Ser Ser Tyr Asp His Met Asp Ser Ala Lys Ser Gly
                 260             265             270

Lys Lys Asp Asn Asp Asn Lys Glu Val Lys Asp Ile Ile Asp Ile Leu
         275             280             285

Leu Gln Leu Leu Asp Asp Arg Ser Phe Thr Phe Asp Leu Thr Leu Asp
     290             295             300

His Ile Lys Ala Val Leu Met Asn Ile Phe Ile Ala Gly Thr Asp Pro
305             310             315             320

Ser Ser Ala Thr Ile Val Trp Ala Met Asn Ala Leu Leu Lys Asn Pro
                 325             330             335

Asn Val Met Ser Lys Val Gln Gly Glu Val Arg Asn Leu Phe Gly Asp
                 340             345             350

Lys Asp Phe Ile Asn Glu Asp Val Glu Ser Leu Pro Tyr Leu Lys
         355             360             365

Ala Val Val Lys Glu Thr Leu Arg Leu Phe Pro Pro Ser Pro Leu Leu
370             375             380

Leu Pro Arg Val Thr Met Glu Thr Cys Asn Ile Glu Gly Tyr Glu Ile
385             390             395             400

Gln Ala Lys Thr Ile Val His Val Asn Ala Trp Ala Ile Ala Arg Asp
                 405             410             415

Pro Glu Asn Trp Glu Glu Pro Glu Lys Phe Pro Glu Arg Phe Leu
             420             425             430

Glu Ser Ser Met Glu Leu Lys Gly Asn Asp Glu Phe Lys Val Ile Pro
             435             440             445
```

```
Phe Gly Ser Gly Arg Arg Met Cys Pro Ala Lys His Met Gly Ile Met
    450                 455                 460
Asn Val Glu Leu Ser Leu Ala Asn Leu Ile His Thr Phe Asp Trp Glu
465                 470                 475                 480
Val Ala Lys Gly Phe Asp Lys Glu Met Leu Asp Thr Gln Met Lys
                485                 490                 495
Pro Gly Ile Thr Met His Lys Lys Ser Asp Leu Tyr Leu Val Ala Lys
            500                 505                 510
Lys Pro Thr Thr
        515

(2) INFORMATION FOR SEQ ID NO:13:

(i) SEQUENCE CHARACTERISTICS:
        (A) LENGTH: 1824 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 54..1616

(xi) SEQUENCE DESCRIPTION: SEQ ID NO:13:

GGAAAATTAG CCTCACAAAA GCAAAGATCA AACAAACCAA GGACGAGAAC ACG ATG         56
                                                            Met
                                                              1

TTG CTT GAA CTT GCA CTT GGT TTA TTG GTT TTG GCT CTG TTT CTG CAC       104
Leu Leu Glu Leu Ala Leu Gly Leu Leu Val Leu Ala Leu Phe Leu His
          5                  10                  15

TTG CGT CCC ACA CCC ACT GCA AAA TCA AAA GCA CTT CGC CAT CTC CCA       152
Leu Arg Pro Thr Pro Thr Ala Lys Ser Lys Ala Leu Arg His Leu Pro
     20                  25                  30

AAC CCA CCA AGC CCA AAG CCT CGT CTT CCC TTC ATA GGA CAC CTT CAT       200
Asn Pro Pro Ser Pro Lys Pro Arg Leu Pro Phe Ile Gly His Leu His
 35                  40                  45

CTC TTA AAA GAC AAA CTT CTC CAC TAC GCA CTC ATC GAC CTC TCC AAA       248
Leu Leu Lys Asp Lys Leu Leu His Tyr Ala Leu Ile Asp Leu Ser Lys
50                  55                  60                  65

AAA CAT GGT CCC TTA TTC TCT CTC TAC TTT GGC TCC ATG CCA ACC GTT       296
Lys His Gly Pro Leu Phe Ser Leu Tyr Phe Gly Ser Met Pro Thr Val
                 70                  75                  80

GTT GCC TCC ACA CCA GAA TTG TTC AAG CTC TTC CTC CAA ACG CAC GAG       344
Val Ala Ser Thr Pro Glu Leu Phe Lys Leu Phe Leu Gln Thr His Glu
             85                  90                  95

GCA ACT TCC TTC AAC ACA AGG TTC CAA ACC TCA GCC ATA AGA CGC CTC       392
Ala Thr Ser Phe Asn Thr Arg Phe Gln Thr Ser Ala Ile Arg Arg Leu
        100                 105                 110

ACC TAT GAT AGC TCA GTG GCC ATG GTT CCC TTC GGA CCT TAC TGG AAG       440
Thr Tyr Asp Ser Ser Val Ala Met Val Pro Phe Gly Pro Tyr Trp Lys
    115                 120                 125

TTC GTG AGG AAG CTC ATC ATG AAC GAC CTT CCC AAC GCC ACC ACT GTA       488
Phe Val Arg Lys Leu Ile Met Asn Asp Leu Pro Asn Ala Thr Thr Val
130                 135                 140                 145

AAC AAG TTG AGG CCT TTG AGG ACC CAA CAG ACC CGC AAG TTC CTT AGG       536
Asn Lys Leu Arg Pro Leu Arg Thr Gln Gln Thr Arg Lys Phe Leu Arg
                150                 155                 160

GTT ATG GCC CAA GGC GCA GAG GCA CAG AAG CCC CTT GAC TTG ACC GAG       584
Val Met Ala Gln Gly Ala Glu Ala Gln Lys Pro Leu Asp Leu Thr Glu
            165                 170                 175
```

```
GAG CTT CTG AAA TGG ACC AAC AGC ACC ATC TCC ATG ATG ATG CTC GGC       632
Glu Leu Leu Lys Trp Thr Asn Ser Thr Ile Ser Met Met Met Leu Gly
            180                 185                 190

GAG GCT GAG GAG ATC AGA GAC ATC GCT CGC GAG GTT CTT AAG ATC TTT       680
Glu Ala Glu Glu Ile Arg Asp Ile Ala Arg Glu Val Leu Lys Ile Phe
            195                 200                 205

GGC GAA TAC AGC CTC ACT GAC TTC ATC TGG CCA TTG AAG CAT CTC AAG       728
Gly Glu Tyr Ser Leu Thr Asp Phe Ile Trp Pro Leu Lys His Leu Lys
210             215                 220                 225

GTT GGA AAG TAT GAG AAG AGG ATC GAC GAC ATC TTG AAC AAG TTC GAC       776
Val Gly Lys Tyr Glu Lys Arg Ile Asp Asp Ile Leu Asn Lys Phe Asp
                230                 235                 240

CCT GTC GTT GAA AGG GTC ATC AAG AAG CGC CGT GAG ATC GTG AGG AGG       824
Pro Val Val Glu Arg Val Ile Lys Lys Arg Arg Glu Ile Val Arg Arg
                245                 250                 255

AGA AAG AAC GGA GAG GTT GTT GAG GGT GAG GTC AGC GGG GTT TTC CTT       872
Arg Lys Asn Gly Glu Val Val Glu Gly Glu Val Ser Gly Val Phe Leu
            260                 265                 270

GAC ACT TTG CTT GAA TTC GCT GAG GAT GAG ACC ATG GAG ATC AAA ATC       920
Asp Thr Leu Leu Glu Phe Ala Glu Asp Glu Thr Met Glu Ile Lys Ile
            275                 280                 285

ACC AAG GAC CAC ATC GAG GGT CTT GTT GTC GAC TTT TTC TCG GCA GGA       968
Thr Lys Asp His Ile Glu Gly Leu Val Val Asp Phe Phe Ser Ala Gly
290             295                 300                 305

ACA GAC TCC ACA GCG GTG GCA ACA GAG TGG GCA TTG GCA GAA CTC ATC      1016
Thr Asp Ser Thr Ala Val Ala Thr Glu Trp Ala Leu Ala Glu Leu Ile
                310                 315                 320

AAC AAT CCT AAG GTG TTG GAA AAG GCT CGT GAG GAG GTC TAC AGT GTT      1064
Asn Asn Pro Lys Val Leu Glu Lys Ala Arg Glu Glu Val Tyr Ser Val
                325                 330                 335

GTG GGA AAG GAC AGA CTT GTG GAC GAA GTT GAC ACT CAA AAC CTT CCT      1112
Val Gly Lys Asp Arg Leu Val Asp Glu Val Asp Thr Gln Asn Leu Pro
            340                 345                 350

TAC ATT AGA GCA ATC GTG AAG GAG ACA TTC CGC ATG CAC CCG CCA CTC      1160
Tyr Ile Arg Ala Ile Val Lys Glu Thr Phe Arg Met His Pro Pro Leu
            355                 360                 365

CCA GTG GTC AAA AGA AAG TGC ACA GAA GAG TGT GAG ATT AAT GGA TAT      1208
Pro Val Val Lys Arg Lys Cys Thr Glu Glu Cys Glu Ile Asn Gly Tyr
370             375                 380                 385

GTG ATC CCA GAG GGA GCA TTG ATT CTC TTC AAT GTA TGG CAA GTA GGA      1256
Val Ile Pro Glu Gly Ala Leu Ile Leu Phe Asn Val Trp Gln Val Gly
                390                 395                 400

AGA GAC CCC AAA TAC TGG GAC AGA CCA TCG GAG TTC CGT CCT GAG AGG      1304
Arg Asp Pro Lys Tyr Trp Asp Arg Pro Ser Glu Phe Arg Pro Glu Arg
                405                 410                 415

TTC CTA GAG ACA GGG GCT GAA GGG GAA GCA GGG CCT CTT GAT CTT AGG      1352
Phe Leu Glu Thr Gly Ala Glu Gly Glu Ala Gly Pro Leu Asp Leu Arg
            420                 425                 430

GGA CAA CAT TTT CAA CTT CTC CCA TTT GGG TCT GGG AGG AGA ATG TGC      1400
Gly Gln His Phe Gln Leu Leu Pro Phe Gly Ser Gly Arg Arg Met Cys
            435                 440                 445

CCT GGA GTC AAT CTG GCT ACT TCG GGA ATG GCA ACA CTT CTT GCA TCT      1448
Pro Gly Val Asn Leu Ala Thr Ser Gly Met Ala Thr Leu Leu Ala Ser
450             455                 460                 465

CTT ATT CAG TGC TTC GAC TTG CAA GTG CTG GGT CCA CAA GGA CAG ATA      1496
Leu Ile Gln Cys Phe Asp Leu Gln Val Leu Gly Pro Gln Gly Gln Ile
                470                 475                 480
```

```
TTG AAG GGT GGT GAC GCC AAA GTT AGC ATG GAA GAG AGA GCC GGC CTC         1544
Leu Lys Gly Gly Asp Ala Lys Val Ser Met Glu Glu Arg Ala Gly Leu
            485                 490                 495

ACT GTT CCA AGG GCA CAT AGT CTT GTC TGT GTT CCA CTT GCA AGG ATC         1592
Thr Val Pro Arg Ala His Ser Leu Val Cys Val Pro Leu Ala Arg Ile
        500                 505                 510

GGC GTT GCA TCT AAA CTC CTT TCT TAATTAAGAT CATCATCATA TATAATATTT        1646
Gly Val Ala Ser Lys Leu Leu Ser
        515                 520

ACTTTTTGTG TGTTGATAAT CATCATTTCA ATAAGGTCTC GTTCATCTAC TTTTTATGAA       1706

GTATATAAGC CCTTCCATGC ACATTGTATC ATCTCCCATT TGTCTTCGTT TGCTACCTAA       1766

GGCAATCTTT TTTTTTTTAG AATCACATCA TCCTACTATA AACTATCAAT CCTTATAT         1824

(2) INFORMATION FOR SEQ ID NO:14:

(i) SEQUENCE CHARACTERISTICS:
        (A) LENGTH: 521 amino acids
        (B) TYPE: amino acid
        (D) TOPOLOGY: linear (ii) MOLECULE TYPE: protein (xi) SEQUENCE DESCRIPTION: SEQ ID NO:14:

Met Leu Leu Glu Leu Ala Leu Gly Leu Leu Val Leu Ala Leu Phe Leu
  1               5                  10                  15

His Leu Arg Pro Thr Pro Thr Ala Lys Ser Lys Ala Leu Arg His Leu
             20                  25                  30

Pro Asn Pro Pro Ser Pro Lys Pro Arg Leu Pro Phe Ile Gly His Leu
         35                  40                  45

His Leu Leu Lys Asp Lys Leu Leu His Tyr Ala Leu Ile Asp Leu Ser
     50                  55                  60

Lys Lys His Gly Pro Leu Phe Ser Leu Tyr Phe Gly Ser Met Pro Thr
 65                  70                  75                  80

Val Val Ala Ser Thr Pro Glu Leu Phe Lys Leu Phe Leu Gln Thr His
                 85                  90                  95

Glu Ala Thr Ser Phe Asn Thr Arg Phe Gln Thr Ser Ala Ile Arg Arg
            100                 105                 110

Leu Thr Tyr Asp Ser Ser Val Ala Met Val Pro Phe Gly Pro Tyr Trp
        115                 120                 125

Lys Phe Val Arg Lys Leu Ile Met Asn Asp Leu Pro Asn Ala Thr Thr
    130                 135                 140

Val Asn Lys Leu Arg Pro Leu Arg Thr Gln Gln Thr Arg Lys Phe Leu
145                 150                 155                 160

Arg Val Met Ala Gln Gly Ala Glu Ala Gln Lys Pro Leu Asp Leu Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys His Leu
    210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255
```

```
Arg Arg Lys Asn Gly Glu Val Val Glu Gly Glu Val Ser Gly Val Phe
        260                 265                 270

Leu Asp Thr Leu Leu Glu Phe Ala Glu Asp Glu Thr Met Glu Ile Lys
        275                 280                 285

Ile Thr Lys Asp His Ile Glu Gly Leu Val Val Asp Phe Phe Ser Ala
        290                 295                 300

Gly Thr Asp Ser Thr Ala Val Ala Thr Glu Trp Ala Leu Ala Glu Leu
305                 310                 315                 320

Ile Asn Asn Pro Lys Val Leu Glu Lys Ala Arg Glu Glu Val Tyr Ser
                325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
        355                 360                 365

Leu Pro Val Val Lys Arg Lys Cys Thr Glu Glu Cys Glu Ile Asn Gly
        370                 375                 380

Tyr Val Ile Pro Glu Gly Ala Leu Ile Leu Phe Asn Val Trp Gln Val
385                 390                 395                 400

Gly Arg Asp Pro Lys Tyr Trp Asp Arg Pro Ser Glu Phe Arg Pro Glu
                405                 410                 415

Arg Phe Leu Glu Thr Gly Ala Glu Gly Glu Ala Gly Pro Leu Asp Leu
            420                 425                 430

Arg Gly Gln His Phe Gln Leu Leu Pro Phe Gly Ser Gly Arg Arg Met
        435                 440                 445

Cys Pro Gly Val Asn Leu Ala Thr Ser Gly Met Ala Thr Leu Leu Ala
        450                 455                 460

Ser Leu Ile Gln Cys Phe Asp Leu Gln Val Leu Gly Pro Gln Gly Gln
465                 470                 475                 480

Ile Leu Lys Gly Gly Asp Ala Lys Val Ser Met Glu Glu Arg Ala Gly
                485                 490                 495

Leu Thr Val Pro Arg Ala His Ser Leu Val Cys Val Pro Leu Ala Arg
            500                 505                 510

Ile Gly Val Ala Ser Lys Leu Leu Ser
        515                 520

(2) INFORMATION FOR SEQ ID NO:15:

(i) SEQUENCE CHARACTERISTICS:
        (A) LENGTH: 1831 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 20..1747

(xi) SEQUENCE DESCRIPTION: SEQ ID NO:15:

CAACACTCGC AGTACCGCC ATG AGT GTC GAC ACT TCC TCC ACC CTC TCC ACC        52
                    Met Ser Val Asp Thr Ser Ser Thr Leu Ser Thr
                     1               5                  10

GTC ACC GAT GCC AAT CTT CAC TCC AGA TTT CAT TCT CGT CTT GTT CCA        100
Val Thr Asp Ala Asn Leu His Ser Arg Phe His Ser Arg Leu Val Pro
             15                  20                  25

TTC ACT CAT CAT TTC TCA CTT TCT CAA CCC AAA CGG ATT TCT TCA ATC        148
Phe Thr His His Phe Ser Leu Ser Gln Pro Lys Arg Ile Ser Ser Ile
        30                  35                  40
```

```
AGA TGC CAA TCA ATT AAT ACC GAT AAG AAG AAA TCA AGT AGA AAT CTG       196
Arg Cys Gln Ser Ile Asn Thr Asp Lys Lys Lys Ser Ser Arg Asn Leu
        45                  50                  55

CTG GGC AAT GCA AGT AAC CTC CTC ACG GAC TTA TTA AGT GGT GGA AGT       244
Leu Gly Asn Ala Ser Asn Leu Leu Thr Asp Leu Leu Ser Gly Gly Ser
60                  65                  70                  75

ATA GGG TCT ATG CCC ATA GCT GAA GGT GCA GTC TCA GAT CTG CTT GGT       292
Ile Gly Ser Met Pro Ile Ala Glu Gly Ala Val Ser Asp Leu Leu Gly
                    80                  85                  90

CGA CCT CTC TTT TTC TCA CTG TAT GAT TGG TTC TTG GAG CAT GGT GCG       340
Arg Pro Leu Phe Phe Ser Leu Tyr Asp Trp Phe Leu Glu His Gly Ala
                95                  100                 105

GTG TAT AAA CTT GCC TTT GGA CCA AAA GCA TTT GTT GTT GTA TCA GAT       388
Val Tyr Lys Leu Ala Phe Gly Pro Lys Ala Phe Val Val Val Ser Asp
            110                 115                 120

CCC ATA GTT GCT AGA CAT ATT CTG CGA GAA AAT GCA TTT TCT TAT GAC       436
Pro Ile Val Ala Arg His Ile Leu Arg Glu Asn Ala Phe Ser Tyr Asp
        125                 130                 135

AAG GGA GTA CTT GCT GAT ATC CTT GAA CCA ATA ATG GGC AAA GGA CTC       484
Lys Gly Val Leu Ala Asp Ile Leu Glu Pro Ile Met Gly Lys Gly Leu
140                 145                 150                 155

ATA CCA GCA GAC CTT GAT ACT TGG AAG CAA AGG AGA AGA GTC ATT GCT       532
Ile Pro Ala Asp Leu Asp Thr Trp Lys Gln Arg Arg Arg Val Ile Ala
                    160                 165                 170

CCG GCT TTC CAT AAC TCA TAC TTG GAA GCT ATG GTT AAA ATA TTC ACA       580
Pro Ala Phe His Asn Ser Tyr Leu Glu Ala Met Val Lys Ile Phe Thr
                175                 180                 185

ACT TGT TCA GAA AGA ACA ATA TTG AAG TTT AAT AAG CTT CTT GAA GGA       628
Thr Cys Ser Glu Arg Thr Ile Leu Lys Phe Asn Lys Leu Leu Glu Gly
            190                 195                 200

GAG GGT TAT GAT GGA CCT GAC TCA ATT GAA TTG GAT CTT GAG GCA GAG       676
Glu Gly Tyr Asp Gly Pro Asp Ser Ile Glu Leu Asp Leu Glu Ala Glu
        205                 210                 215

TTT TCT AGT TTG GCT CTT GAT ATT ATT GGG CTT GGT GTG TTC AAC TAT       724
Phe Ser Ser Leu Ala Leu Asp Ile Ile Gly Leu Gly Val Phe Asn Tyr
220                 225                 230                 235

GAC TTT GGT TCT GTC ACC AAA GAA TCT CCA GTT ATT AAG GCA GTC TAT       772
Asp Phe Gly Ser Val Thr Lys Glu Ser Pro Val Ile Lys Ala Val Tyr
                    240                 245                 250

GGC ACT CTT TTT GAA GCT GAA CAC AGA TCC ACT TTC TAC ATT CCA TAT       820
Gly Thr Leu Phe Glu Ala Glu His Arg Ser Thr Phe Tyr Ile Pro Tyr
                255                 260                 265

TGG AAA ATT CCA TTG GCA AGG TGG ATA GTC CCA AGG CAA AGA AAG TTT       868
Trp Lys Ile Pro Leu Ala Arg Trp Ile Val Pro Arg Gln Arg Lys Phe
            270                 275                 280

CAG GAT GAC CTA AAG GTC ATC AAT ACT TGT CTT GAT GGA CTT ATC AGA       916
Gln Asp Asp Leu Lys Val Ile Asn Thr Cys Leu Asp Gly Leu Ile Arg
        285                 290                 295

AAT GCA AAA GAG AGC AGA CAG GAA ACA GAT GTT GAG AAA TTG CAG CAG       964
Asn Ala Lys Glu Ser Arg Gln Glu Thr Asp Val Glu Lys Leu Gln Gln
300                 305                 310                 315

AGG GAT TAC TTA AAT TTG AAG GAT GCA AGT CTT CTG CGT TTC CTG GTT      1012
Arg Asp Tyr Leu Asn Leu Lys Asp Ala Ser Leu Leu Arg Phe Leu Val
                    320                 325                 330

GAT ATG CGG GGA GCT GAT GTT GAT GAT CGT CAG TTG AGG GAT GAT TTA      1060
Asp Met Arg Gly Ala Asp Val Asp Asp Arg Gln Leu Arg Asp Asp Leu
                335                 340                 345
```

```
ATG ACA ATG CTT ATT GCC GGT CAT GAA ACA ACG GCT GCA GTT CTT ACT       1108
Met Thr Met Leu Ile Ala Gly His Glu Thr Thr Ala Ala Val Leu Thr
            350                 355                 360

TGG GCA GTT TTC CTC CTA GCT CAA AAT CCT AGC AAA ATG AAG AAG GCT       1156
Trp Ala Val Phe Leu Leu Ala Gln Asn Pro Ser Lys Met Lys Lys Ala
    365                 370                 375

CAA GCA GAG GTA GAT TTG GTG CTG GGT ACG GGG AGG CCA ACT TTT GAA       1204
Gln Ala Glu Val Asp Leu Val Leu Gly Thr Gly Arg Pro Thr Phe Glu
380                 385                 390                 395

TCA CTT AAG GAA TTG CAG TAC ATT AGA TTG ATT GTT GTG GAG GCT CTT       1252
Ser Leu Lys Glu Leu Gln Tyr Ile Arg Leu Ile Val Val Glu Ala Leu
                400                 405                 410

CGT TTA TAC CCC CAA CCA CCT TTG CTG ATT AGA CGT TCA CTC AAA TCT       1300
Arg Leu Tyr Pro Gln Pro Pro Leu Leu Ile Arg Arg Ser Leu Lys Ser
            415                 420                 425

GAT GTT TTA CCA GGT GGG CAC AAA GGT GAA AAA GAT GGT TAT GCA ATT       1348
Asp Val Leu Pro Gly Gly His Lys Gly Glu Lys Asp Gly Tyr Ala Ile
        430                 435                 440

CCT GCT GGG ACT GAT GTC TTC ATT TCT GTA TAT AAT CTC CAT AGA TCT       1396
Pro Ala Gly Thr Asp Val Phe Ile Ser Val Tyr Asn Leu His Arg Ser
    445                 450                 455

CCA TAT TTT TGG GAC CGC CCT GAT GAC TTC GAA CCA GAG AGA TTT CTT       1444
Pro Tyr Phe Trp Asp Arg Pro Asp Asp Phe Glu Pro Glu Arg Phe Leu
460                 465                 470                 475

GTG CAA AAC AAG AAT GAA GAA ATT GAA GGA TGG GCT GGT CTT GAT CCA       1492
Val Gln Asn Lys Asn Glu Glu Ile Glu Gly Trp Ala Gly Leu Asp Pro
                480                 485                 490

TCT CGA AGT CCC GGA GCC TTG TAT CCG AAC GAG GTT ATA TCG GAT TTT       1540
Ser Arg Ser Pro Gly Ala Leu Tyr Pro Asn Glu Val Ile Ser Asp Phe
            495                 500                 505

GCA TTC TTA CCT TTT GGT GGC GGA CCA CGA AAA TGT GTT GGG GAC CAA       1588
Ala Phe Leu Pro Phe Gly Gly Gly Pro Arg Lys Cys Val Gly Asp Gln
        510                 515                 520

TTT GCT CTG ATG GAG TCC ACT GTA GCG TTG ACT ATG CTG CTC CAG AAT       1636
Phe Ala Leu Met Glu Ser Thr Val Ala Leu Thr Met Leu Leu Gln Asn
    525                 530                 535

TTT GAC GTG GAA CTA AAA GGG ACC CCT GAA TCG GTG GAA CTA GTT ACT       1684
Phe Asp Val Glu Leu Lys Gly Thr Pro Glu Ser Val Glu Leu Val Thr
540                 545                 550                 555

GGG GCA ACT ATT CAT ACC AAA AAT GGA ATG TGG TGC AGA TTG AAG AAG       1732
Gly Ala Thr Ile His Thr Lys Asn Gly Met Trp Cys Arg Leu Lys Lys
                560                 565                 570

AGA TCT AAT TTA CGT TGACATATGT ACTGTGGCCA TTTTTCTTAT ACAGAATAAT       1787
Arg Ser Asn Leu Arg
            575

GTATATTATT ATTCTTTGAG AATAATATGA ATAAATTCCT AGAC                      1831
```

(2) INFORMATION FOR SEQ ID NO:16:

(i) SEQUENCE CHARACTERISTICS:
        (A) LENGTH: 576 amino acids
        (B) TYPE: amino acid
        (D) TOPOLOGY: linear (ii) MOLECULE TYPE: protein (xi) SEQUENCE DESCRIPTION: SEQ ID NO:16:

```
Met Ser Val Asp Thr Ser Ser Thr Leu Ser Thr Val Thr Asp Ala Asn
 1               5                  10                  15

Leu His Ser Arg Phe His Ser Arg Leu Val Pro Phe Thr His His Phe
            20                  25                  30
```

-continued

```
Ser Leu Ser Gln Pro Lys Arg Ile Ser Ser Ile Arg Cys Gln Ser Ile
         35                  40                  45

Asn Thr Asp Lys Lys Ser Ser Arg Asn Leu Leu Gly Asn Ala Ser
 50                  55                  60

Asn Leu Leu Thr Asp Leu Leu Ser Gly Gly Ser Ile Gly Ser Met Pro
 65                  70                  75                  80

Ile Ala Glu Gly Ala Val Ser Asp Leu Leu Gly Arg Pro Leu Phe Phe
                 85                  90                  95

Ser Leu Tyr Asp Trp Phe Leu Glu His Gly Ala Val Tyr Lys Leu Ala
             100                 105                 110

Phe Gly Pro Lys Ala Phe Val Val Ser Asp Pro Ile Val Ala Arg
         115                 120                 125

His Ile Leu Arg Glu Asn Ala Phe Ser Tyr Asp Lys Gly Val Leu Ala
 130                 135                 140

Asp Ile Leu Glu Pro Ile Met Gly Lys Gly Leu Ile Pro Ala Asp Leu
145                 150                 155                 160

Asp Thr Trp Lys Gln Arg Arg Val Ile Ala Pro Ala Phe His Asn
             165                 170                 175

Ser Tyr Leu Glu Ala Met Val Lys Ile Phe Thr Thr Cys Ser Glu Arg
         180                 185                 190

Thr Ile Leu Lys Phe Asn Lys Leu Leu Glu Gly Gly Tyr Asp Gly
         195                 200                 205

Pro Asp Ser Ile Glu Leu Asp Leu Glu Ala Glu Phe Ser Ser Leu Ala
 210                 215                 220

Leu Asp Ile Ile Gly Leu Gly Val Phe Asn Tyr Asp Phe Gly Ser Val
225                 230                 235                 240

Thr Lys Glu Ser Pro Val Ile Lys Ala Val Tyr Gly Thr Leu Phe Glu
             245                 250                 255

Ala Glu His Arg Ser Thr Phe Tyr Ile Pro Tyr Trp Lys Ile Pro Leu
         260                 265                 270

Ala Arg Trp Ile Val Pro Arg Gln Arg Lys Phe Gln Asp Asp Leu Lys
         275                 280                 285

Val Ile Asn Thr Cys Leu Asp Gly Leu Ile Arg Asn Ala Lys Glu Ser
 290                 295                 300

Arg Gln Glu Thr Asp Val Glu Lys Leu Gln Gln Arg Asp Tyr Leu Asn
305                 310                 315                 320

Leu Lys Asp Ala Ser Leu Leu Arg Phe Leu Val Asp Met Arg Gly Ala
             325                 330                 335

Asp Val Asp Asp Arg Gln Leu Arg Asp Asp Leu Met Thr Met Leu Ile
             340                 345                 350

Ala Gly His Glu Thr Thr Ala Ala Val Leu Thr Trp Ala Val Phe Leu
         355                 360                 365

Leu Ala Gln Asn Pro Ser Lys Met Lys Lys Ala Gln Ala Glu Val Asp
 370                 375                 380

Leu Val Leu Gly Thr Gly Arg Pro Thr Phe Glu Ser Leu Lys Glu Leu
385                 390                 395                 400

Gln Tyr Ile Arg Leu Ile Val Val Glu Ala Leu Arg Leu Tyr Pro Gln
             405                 410                 415

Pro Pro Leu Leu Ile Arg Arg Ser Leu Lys Ser Asp Val Leu Pro Gly
         420                 425                 430

Gly His Lys Gly Glu Lys Asp Gly Tyr Ala Ile Pro Ala Gly Thr Asp
         435                 440                 445
```

```
Val Phe Ile Ser Val Tyr Asn Leu His Arg Ser Pro Tyr Phe Trp Asp
    450                 455                 460

Arg Pro Asp Asp Phe Glu Pro Glu Arg Phe Leu Val Gln Asn Lys Asn
465                 470                 475                 480

Glu Glu Ile Glu Gly Trp Ala Gly Leu Asp Pro Ser Arg Ser Pro Gly
                485                 490                 495

Ala Leu Tyr Pro Asn Glu Val Ile Ser Asp Phe Ala Phe Leu Pro Phe
            500                 505                 510

Gly Gly Gly Pro Arg Lys Cys Val Gly Asp Gln Phe Ala Leu Met Glu
        515                 520                 525

Ser Thr Val Ala Leu Thr Met Leu Leu Gln Asn Phe Asp Val Glu Leu
    530                 535                 540

Lys Gly Thr Pro Glu Ser Val Glu Leu Val Thr Gly Ala Thr Ile His
545                 550                 555                 560

Thr Lys Asn Gly Met Trp Cys Arg Leu Lys Lys Arg Ser Asn Leu Arg
                565                 570                 575
```

(2) INFORMATION FOR SEQ ID NO:17:

(i) SEQUENCE CHARACTERISTICS:
        (A) LENGTH: 1704 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 38..1564

(xi) SEQUENCE DESCRIPTION: SEQ ID NO:17:

```
CAGGCTCCAC AAAACATCTC ATCATTCACC CAACAAA ATG GCG CTG CTT CTG ATA        55
                                         Met Ala Leu Leu Leu Ile
                                           1               5

ATT CCC ATC TCA CTG GTC ACC CTC TGG CTC GGT TAC ACC CTA TAC CAG        103
Ile Pro Ile Ser Leu Val Thr Leu Trp Leu Gly Tyr Thr Leu Tyr Gln
             10                  15                  20

CGA TTA AGA TTC AAG CTC CCT CCG GGT CCA CGG CCC TGG CCG GTA GTC        151
Arg Leu Arg Phe Lys Leu Pro Pro Gly Pro Arg Pro Trp Pro Val Val
         25                  30                  35

GGT AAC CTC TAC GAC ATA AAA CCC GTC CGC TTC CGG TGC TTC GCG GAG        199
Gly Asn Leu Tyr Asp Ile Lys Pro Val Arg Phe Arg Cys Phe Ala Glu
     40                  45                  50

TGG GCG CAG TCT TAC GGC CCC ATA ATA TCG GTT TGG TTC GGT TCG ACC        247
Trp Ala Gln Ser Tyr Gly Pro Ile Ile Ser Val Trp Phe Gly Ser Thr
 55                  60                  65                  70

CTA AAC GTC ATC GTT TCG AAC TCG GAG CTG GCG AAG GAG GTG CTG AAG        295
Leu Asn Val Ile Val Ser Asn Ser Glu Leu Ala Lys Glu Val Leu Lys
                 75                  80                  85

GAG CAC GAT CAG CTG CTG GCG GAC CGC CAC CGG AGC CGG TCG GCG GCG        343
Glu His Asp Gln Leu Leu Ala Asp Arg His Arg Ser Arg Ser Ala Ala
             90                  95                 100

AAG TTC AGC CGC GAC GGG AAG GAT CTA ATT TGG GCC GAT TAT GGG CCG        391
Lys Phe Ser Arg Asp Gly Lys Asp Leu Ile Trp Ala Asp Tyr Gly Pro
         105                 110                 115

CAC TAC GTG AAG GTG AGG AAG GTT TGC ACG CTC GAG CTT TTC TCG CCG        439
His Tyr Val Lys Val Arg Lys Val Cys Thr Leu Glu Leu Phe Ser Pro
     120                 125                 130
```

```
AAG CGC CTC GAG GCC CTG AGG CCC ATT AGG GAG GAC GAG GTC ACC TCC       487
Lys Arg Leu Glu Ala Leu Arg Pro Ile Arg Glu Asp Glu Val Thr Ser
135                 140                 145                 150

ATG GTT GAC TCC GTT TAC AAT CAC TGC ACC AGC ACT GAA AAT TTG GGG       535
Met Val Asp Ser Val Tyr Asn His Cys Thr Ser Thr Glu Asn Leu Gly
                    155                 160                 165

AAA GGA ATA TTG TTG AGG AAG CAC TTG GGG GTT GTG GCA TTC AAC AAC       583
Lys Gly Ile Leu Leu Arg Lys His Leu Gly Val Val Ala Phe Asn Asn
                170                 175                 180

ATA ACC AGG TTG GCA TTT GGG AAA AGA TTT GTG AAC TCA GAA GGT GTG       631
Ile Thr Arg Leu Ala Phe Gly Lys Arg Phe Val Asn Ser Glu Gly Val
            185                 190                 195

ATG GAT GAG CAA GGA GTA GAA TTC AAG GCC ATT GTG GAA AAT GGG TTA       679
Met Asp Glu Gln Gly Val Glu Phe Lys Ala Ile Val Glu Asn Gly Leu
200                 205                 210

AAG CTA GGA GCA TCT CTA GCC ATG GCA GAA CAC ATC CCT TGG CTT CGC       727
Lys Leu Gly Ala Ser Leu Ala Met Ala Glu His Ile Pro Trp Leu Arg
215                 220                 225                 230

TGG ATG TTC CCA CTG GAA GAA GGA GCT TTT GCC AAG CAT GGA GCC CGC       775
Trp Met Phe Pro Leu Glu Glu Gly Ala Phe Ala Lys His Gly Ala Arg
                235                 240                 245

CGC GAC CGA CTC ACC AGA GCC ATC ATG GCA GAG CAC ACT GAA GCA CGC       823
Arg Asp Arg Leu Thr Arg Ala Ile Met Ala Glu His Thr Glu Ala Arg
            250                 255                 260

AAG AAA TCT GGT GGT GCC AAG CAA CAT TTT GTT GAT GCC CTC CTC ACA       871
Lys Lys Ser Gly Gly Ala Lys Gln His Phe Val Asp Ala Leu Leu Thr
265                 270                 275

TTG CAA GAC AAA TAT GAC CTT AGT GAA GAC ACC ATC ATT GGT CTC CTT       919
Leu Gln Asp Lys Tyr Asp Leu Ser Glu Asp Thr Ile Ile Gly Leu Leu
280                 285                 290

TGG GAT ATG ATC ACA GCA GGG ATG GAC ACA ACT GCA ATT TCA GTT GAG       967
Trp Asp Met Ile Thr Ala Gly Met Asp Thr Thr Ala Ile Ser Val Glu
295                 300                 305                 310

TGG GCC ATG GCT GAG TTG ATA AGA AAC CCA AGG GTG CAA CAA AAG GTC      1015
Trp Ala Met Ala Glu Leu Ile Arg Asn Pro Arg Val Gln Gln Lys Val
                315                 320                 325

CAA GAG GAG CTA GAC AGG GTA ATT GGG CTT GAA AGG GTG ATG ACT GAA      1063
Gln Glu Glu Leu Asp Arg Val Ile Gly Leu Glu Arg Val Met Thr Glu
            330                 335                 340

GCA GAC TTC TCA AAT CTC CCT TAC CTA CAA TGT GTG ACC AAA GAA GCA      1111
Ala Asp Phe Ser Asn Leu Pro Tyr Leu Gln Cys Val Thr Lys Glu Ala
            345                 350                 355

ATG AGG CTT CAC CCA CCA ACC CCA CTA ATG CTC CCA CAC CGT GCC AAT      1159
Met Arg Leu His Pro Pro Thr Pro Leu Met Leu Pro His Arg Ala Asn
360                 365                 370

GCC AAT GTC AAA GTT GGA GGC TAT GAC ATT CCC AAA GGG TCC AAT GTG      1207
Ala Asn Val Lys Val Gly Gly Tyr Asp Ile Pro Lys Gly Ser Asn Val
375                 380                 385                 390

CAT GTG AAT GTG TGG GCG GTG GCC CGC GAC CCG GCC GTG TGG AAG GAT      1255
His Val Asn Val Trp Ala Val Ala Arg Asp Pro Ala Val Trp Lys Asp
                395                 400                 405

CCA TTG GAG TTC CGA CCC GAA AGG TTC CTT GAG GAG GAT GTA GAC ATG      1303
Pro Leu Glu Phe Arg Pro Glu Arg Phe Leu Glu Glu Asp Val Asp Met
            410                 415                 420

AAG GGC CAT GAC TTT AGG CTA CTT CCA TTC GGG TCG GGT CGA CGA GTA      1351
Lys Gly His Asp Phe Arg Leu Leu Pro Phe Gly Ser Gly Arg Arg Val
            425                 430                 435

TGC CCG GGT GCC CAA CTT GGT ATC AAC TTG GCA GCA TCC ATG TTG GGC      1399
Cys Pro Gly Ala Gln Leu Gly Ile Asn Leu Ala Ala Ser Met Leu Gly
440                 445                 450
```

```
CAC CTC TTG CAC CAT TTC TGT TGG ACC CCA CCT GAA GGA ATG AAG CCT    1447
His Leu Leu His His Phe Cys Trp Thr Pro Pro Glu Gly Met Lys Pro
455                 460                 465                 470

GAG GAA ATT GAC ATG GGA GAG AAT CCA GGG CTA GTC ACA TAC ATG AGG    1495
Glu Glu Ile Asp Met Gly Glu Asn Pro Gly Leu Val Thr Tyr Met Arg
                475                 480                 485

ACT CCA ATA CAA GCT GTG GTT TCT CCT AGG CTC CCC TCA CAT TTA TAC    1543
Thr Pro Ile Gln Ala Val Val Ser Pro Arg Leu Pro Ser His Leu Tyr
            490                 495                 500

AAA CGT GTG CCT GCT GAG ATC TAATCTTTCT TTTCTTTCCC TTGGACTACT       1594
Lys Arg Val Pro Ala Glu Ile
            505

CTTTGTTGCA TTAAGAAAAA TGCCTTGTGG CACTACTTTT ATCTTTGTGT TTATGTAACT  1654

ACATATGAAA TCACAATTTA AGGAACTAAG GAAAAACTCA TTGCGAGGGT             1704

(2) INFORMATION FOR SEQ ID NO:18:

(i) SEQUENCE CHARACTERISTICS:
        (A) LENGTH: 509 amino acids
        (B) TYPE: amino acid
        (D) TOPOLOGY: linear (ii) MOLECULE TYPE: protein (xi) SEQUENCE DESCRIPTION: SEQ ID NO:18:

Met Ala Leu Leu Leu Ile Ile Pro Ile Ser Leu Val Thr Leu Trp Leu
1               5                   10                  15

Gly Tyr Thr Leu Tyr Gln Arg Leu Arg Phe Lys Leu Pro Pro Gly Pro
            20                  25                  30

Arg Pro Trp Pro Val Val Gly Asn Leu Tyr Asp Ile Lys Pro Val Arg
        35                  40                  45

Phe Arg Cys Phe Ala Glu Trp Ala Gln Ser Tyr Gly Pro Ile Ile Ser
    50                  55                  60

Val Trp Phe Gly Ser Thr Leu Asn Val Ile Val Ser Asn Ser Glu Leu
65                  70                  75                  80

Ala Lys Glu Val Leu Lys Glu His Asp Gln Leu Leu Ala Asp Arg His
                85                  90                  95

Arg Ser Arg Ser Ala Ala Lys Phe Ser Arg Asp Gly Lys Asp Leu Ile
            100                 105                 110

Trp Ala Asp Tyr Gly Pro His Tyr Val Lys Val Arg Lys Val Cys Thr
        115                 120                 125

Leu Glu Leu Phe Ser Pro Lys Arg Leu Glu Ala Leu Arg Pro Ile Arg
    130                 135                 140

Glu Asp Glu Val Thr Ser Met Val Asp Ser Val Tyr Asn His Cys Thr
145                 150                 155                 160

Ser Thr Glu Asn Leu Gly Lys Gly Ile Leu Leu Arg Lys His Leu Gly
                165                 170                 175

Val Val Ala Phe Asn Asn Ile Thr Arg Leu Ala Phe Gly Lys Arg Phe
            180                 185                 190

Val Asn Ser Glu Gly Val Met Asp Glu Gln Gly Val Glu Phe Lys Ala
        195                 200                 205

Ile Val Glu Asn Gly Leu Lys Leu Gly Ala Ser Leu Ala Met Ala Glu
    210                 215                 220

His Ile Pro Trp Leu Arg Trp Met Phe Pro Leu Glu Glu Gly Ala Phe
225                 230                 235                 240
```

```
Ala Lys His Gly Ala Arg Arg Asp Arg Leu Thr Arg Ala Ile Met Ala
                245                 250                 255

Glu His Thr Glu Ala Arg Lys Lys Ser Gly Gly Ala Lys Gln His Phe
            260                 265                 270

Val Asp Ala Leu Leu Thr Leu Gln Asp Lys Tyr Asp Leu Ser Glu Asp
            275                 280                 285

Thr Ile Ile Gly Leu Leu Trp Asp Met Ile Thr Ala Gly Met Asp Thr
290                 295                 300

Thr Ala Ile Ser Val Glu Trp Ala Met Ala Glu Leu Ile Arg Asn Pro
305                 310                 315                 320

Arg Val Gln Gln Lys Val Gln Glu Glu Leu Asp Arg Val Ile Gly Leu
                325                 330                 335

Glu Arg Val Met Thr Glu Ala Asp Phe Ser Asn Leu Pro Tyr Leu Gln
                340                 345                 350

Cys Val Thr Lys Glu Ala Met Arg Leu His Pro Pro Thr Pro Leu Met
            355                 360                 365

Leu Pro His Arg Ala Asn Ala Asn Val Lys Val Gly Gly Tyr Asp Ile
370                 375                 380

Pro Lys Gly Ser Asn Val His Val Asn Val Trp Ala Val Ala Arg Asp
385                 390                 395                 400

Pro Ala Val Trp Lys Asp Pro Leu Glu Phe Arg Pro Glu Arg Phe Leu
                405                 410                 415

Glu Glu Asp Val Asp Met Lys Gly His Asp Phe Arg Leu Leu Pro Phe
                420                 425                 430

Gly Ser Gly Arg Arg Val Cys Pro Gly Ala Gln Leu Gly Ile Asn Leu
                435                 440                 445

Ala Ala Ser Met Leu Gly His Leu Leu His His Phe Cys Trp Thr Pro
450                 455                 460

Pro Glu Gly Met Lys Pro Glu Glu Ile Asp Met Gly Glu Asn Pro Gly
465                 470                 475                 480

Leu Val Thr Tyr Met Arg Thr Pro Ile Gln Ala Val Val Ser Pro Arg
                485                 490                 495

Leu Pro Ser His Leu Tyr Lys Arg Val Pro Ala Glu Ile
                500                 505
```

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

TGTCTAACTC CTTCCTTTTC    20

(2) INFORMATION FOR SEQ ID NO:20:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Phe Leu Pro Phe Gly Xaa Gly Xaa Arg Xaa Cys Xaa Gly
1               5                   10
```

(2) INFORMATION FOR SEQ ID NO:21:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Phe Xaa Xaa Gly Xaa Xaa Xaa Cys Xaa Gly
1               5                   10
```

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Xaa Cys Xaa Gly
1
```

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Pro Glu Glu Phe Xaa Pro Glu Arg Phe
1               5
```